US009494591B2

(12) United States Patent
Jabado et al.

(10) Patent No.: US 9,494,591 B2
(45) Date of Patent: Nov. 15, 2016

(54) MUTATIONS OF HISTONE PROTEINS ASSOCIATED WITH PROLIFERATIVE DISORDERS

(71) Applicants: The Royal Institution for the Advancement of Learning/McGill University, Montreal (CA); German Cancer Research Center (DKFZ), Heidelberg (DE); Universitatsklinikum Heidelberg, Heidelberg (DE)

(72) Inventors: Nada Jabado, Montreal (CA); Stefan M. Pfister, Heidelberg (DE); Christoph Plass, Schriesheim-Altenbach (DE); Andrey Korshunov, Heidelberg (DE); Hendrik Witt, Heidelberg (DE); Dominik Sturm, Heidelberg (DE); David Jones, Heidelberg (DE); Peter Lichter, Gaiberg (DE); Elke Pfaff, Heidelberg (DE)

(73) Assignees: THE ROYAL INSTITUTION FOR THE ADVANCEMENT OF LEARNING/MCGILL UNIVERSITY, Montreal (CA); UNIVERSITÄTSKLINIKUM HEIDELBERG, Heidelberg (DE); GERMAN CANCER RESEARCH CENTER (DKFZ), Heidelberg (DE)

( * ) Notice: Subject to any disclaimer, the term of this patent is extended or adjusted under 35 U.S.C. 154(b) by 20 days.

(21) Appl. No.: 14/359,900

(22) PCT Filed: Nov. 21, 2012

(86) PCT No.: PCT/CA2012/050834
§ 371 (c)(1),
(2) Date: May 21, 2014

(87) PCT Pub. No.: WO2013/075237
PCT Pub. Date: May 30, 2013

(65) Prior Publication Data
US 2014/0309292 A1    Oct. 16, 2014

Related U.S. Application Data

(60) Provisional application No. 61/562,204, filed on Nov. 21, 2011, provisional application No. 61/564,390, filed on Nov. 29, 2011.

(51) Int. Cl.
C07K 16/18       (2006.01)
G01N 33/574      (2006.01)
C07K 14/47       (2006.01)
G01N 33/68       (2006.01)
C12Q 1/68        (2006.01)
A61K 38/00       (2006.01)

(52) U.S. Cl.
CPC ......... *G01N 33/57496* (2013.01); *C07K 14/47* (2013.01); *C07K 16/18* (2013.01); *C12Q 1/6886* (2013.01); *G01N 33/57407* (2013.01); *G01N 33/6875* (2013.01); *A61K 38/00* (2013.01); *C07K 2317/34* (2013.01); *G01N 2500/00* (2013.01); *G01N 2800/50* (2013.01); *G01N 2800/56* (2013.01)

(58) Field of Classification Search
None
See application file for complete search history.

(56) References Cited

U.S. PATENT DOCUMENTS

2007/0015145 A1* 1/2007 Woolf .................... C07K 16/22
                                                      435/6.16

FOREIGN PATENT DOCUMENTS

EP           0967288        12/1999
WO      WO 2012/051622      4/2012

OTHER PUBLICATIONS

Estéve et al., "Functional analysis of the N- and C-terminus of mammalian G9a histone H2 methyltransferase", Nucleic Acids Research, 2005, pp. 3211-3223.*
Gurel et al., "Nuclear MYC Protein Overexpression is an Early Alteration in Human Prostate Carcinogenesis", Mod. Pathol., 2008, pp. 1156-1167.*
Angéle Santenard et al., "Heterochromatin formation in the mouse embryo requires critical residues of the histone variant H3.3", Nature Cell Biology, 12(9):853-862 and Supp. Information 1-9, 2010.
Extended European Search Report and Opinion for EP 12851407.2, mailed Apr. 24, 2015.
GenBank accession No. EU934390.1,Anopheles darlingi AD-281 H3 histone family 3A mRNA, complete cds, mRNA sequence, Database GenBank Nucleotide [Online], Oct. 11, 2008.
Heaphy et al., Altered telomeres in tumors with ATRX and DAXX mutations, Science 333 (6041), 425 (2011).
Iwase, S. et al. ATRX ADD domain links an atypical histone methylation recognition mechanism to human mental-retardation syndrome. Nat Struct Mol Biol 18, 769-776, 2011.
Khuong-Quang, et al., K27M mutation in histone H3.3 defines clinically and biologically distinct subgroups of pediatric diffuse intrinsic pontine gliomas. Acta Neuropathol. 124:439-447, 2012.
(Continued)

*Primary Examiner* — Lianko Garyu
(74) *Attorney, Agent, or Firm* — Norton Rose Fulbright US LLP

(57) ABSTRACT

The present application shows the relationship between variations in the amino acid sequence of histone proteins, more specifically the H3.3 protein, and proliferation-associated disorders. Herewith provided are predictive methods, commercial packages, therapeutic methods and screening methods based on this relationship.

5 Claims, 19 Drawing Sheets

(56) References Cited

OTHER PUBLICATIONS

Maher, E. A. et al. Marked genomic differences characterize primary and secondary glioblastoma subtypes and identify two distinct molecular and clinical secondary glioblastoma entities. Cancer Res 66, 11502-11513 (2006).

Narayan et al., Ultrasensitive measurement of hotspot mutations in tumor DNA in blood using error suppressed multiplexed deep sequencing, Cancer Res 72, 3492 (Jul. 15, 2012).

Parsons et al., An integrated genomic analysis of human glioblastoma multiforme. Science 321, 1807-1812, doi:1164382, 2008.

Paugh, B. S. et al. Integrated molecular genetic profiling of pediatric high-grade gliomas reveals key differences with the adult disease. J Clin Oncol 28, 3061-3068, 2010.

Peiffer et al., High-resolution genomic profiling of chromosomal aberrations using Infinium whole genome genotyping. Genome Res 16(9), 1136-1148 (2006).

Schwartzentruber, J. et al., Driver mutations in histone H3.3 and chromatin remodelling genes in paediatric glioblastoma, published online Jan. 29, 2012, Nature 482(7384):226-31, ISSN: 0028-0836.

Sturm, et al., Hotspot Mutations in H3F3A and IDH1 Define Destinct Epigenetic and Biological Subgroups of Glioblastoma. Cancer Cell. 22:425-37, 2012.

Verhaak et al. Integrated genomic analysis identifies clinically relevant subtypes of glioblastoma characterized by abnormalities in PDGFRA, IDH1, EGFR, and NF1. Cancer Cell 17, 98-110, 2010.

\* cited by examiner

Figure 1A

| Sample ID | H3F3A | ATRX/DAXX | TP53 | IDH1 | NF1 | PDGFRα |
|---|---|---|---|---|---|---|
| PGBM1 | K27M | C1122fs | P152fs;R306X | WT | WT | WT |
| PGBM2 | K27M | WT | R213X* | WT | WT | K385I |
| PGBM3 | K27M | WT | N131del | WT | WT | WT |
| PGBM4 | K27M | K1057fs* | G262fs* | WT | WT | WT |
| PGBM5 | K27M | WT | WT | WT | Y2264fs | WT |
| PGBM6 | K27M | M1800T* | WT | WT | F1247fs;V2230del | WT |
| PGBM8 | K27M | WT | R273C | WT | WT | WT |
| PGBM9 | K27M | WT | R273P* | WT | WT | WT |
| PGBM10 | K27M | WT | WT | WT | T990fs | WT |
| PGBM11 | G34R | S1394fs* | Y163C* | WT | WT | WT |
| PGBM12 | G34R | E1727fs | R342X;R175H | WT | WT | Y849D* |
| PGBM13 | G34R | R1739X* | T256fs* | WT | WT | WT |
| PGBM14 | G34R | E1757X* | R273C;R248Q | WT | WT | WT |
| PGBM15 | G34R | H2254R* | S51delins | WT | WT | WT |
| PGBM16 | G34V | R2111X* | R342X* | WT | WT | K385M |
| PGBM17 | WT | G1589V* | Y220C | R132H | WT | WT |
| PGBM18 | WT | R1426X* | R273C;R196X | R132H | C622X;L1489fs | WT |
| PGBM19 | WT | K1584fs¶ | R267Q;T230I | WT | R440X | WT |
| PGBM20 | WT | N2443D* | R248W* | WT | WT | WT |
| PGBM21 | WT | R238X (DAXX) | R267W;P152L | WT | R1947X | WT |
| PGBM22 | WT | R1302fs;K1584fs‡ | R337C;R175H | WT | R2616X;R461X‡ | WT |
| PGBM23 | WT | WT | I254S | R132H | WT | WT |
| PGBM24 | WT | WT | R196X* | WT | WT | WT |
| PGBM25 | WT | WT | R342X* | WT | G1526fs* | WT |
| PGBM26 | WT | WT | R175H* | WT | Y2264fs* | WT |
| PGBM27 | WT | WT | I251L* | WT | WT | WT |
| PGBM28 | WT | WT | R273H | WT | T676fs | WT |
| PGBM29 | WT | WT | V10G | R132H | WT | WT |
| PGBM30 | WT | WT | G245S* | WT | WT | WT |
| PGBM31 | WT | WT | WT | WT | WT | WT |
| PGBM32 | WT | WT | WT | WT | T1627S | WT |
| PGBM33 | WT | WT | WT | WT | splicing | WT |
| PGBM34 | WT | WT | WT | WT | WT | D842_I853delinsV |
| PGBM35 | WT | WT | WT | WT | WT | WT |
| ... | ... | ... | ... | ... | ... | ... |
| PGBM49 | WT | WT | WT | WT | WT | WT |

Figure 2

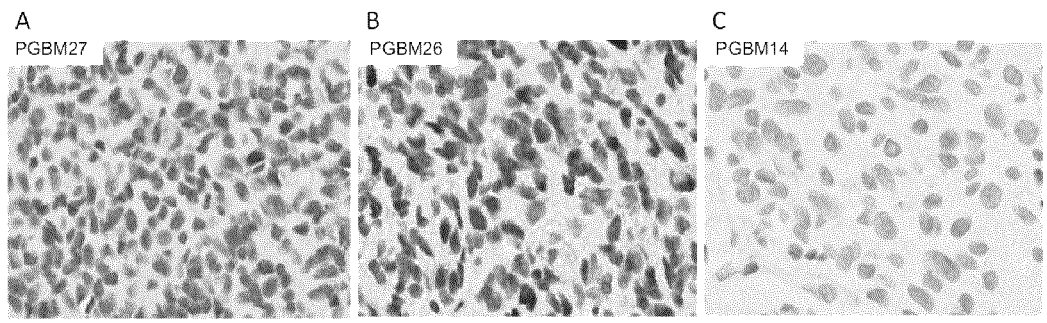

Figure 3A

| Grade | | Diagnosis | Total no. of cases | No. H3F3A mut. | P-value |
|---|---|---|---|---|---|
| High grade | Grade IV | Adult GBM<br>Paediatric GBM | 318<br>90 | 11 (3.4%)<br>32 (35.6%) | <0.0001* |
| | Grade III | Adult AA<br>Paediatric AA | 108<br>11 | 0 (0%)<br>2 (18.2%) | 0.0078* |
| | | Adult AO<br>Paediatric AO | 34<br>5 | 0 (0%)<br>0 (0%) | NA |
| | | Adult AOA<br>Paediatric AOA | 37<br>2 | 0 (0%)<br>0 (0%) | NA |
| Low grade | Grade II | Adult A<br>Paediatric A | 57<br>10 | 0 (0%)<br>0 (0%) | NA |
| | | Adult O<br>Paediatric O | 41<br>2 | 0 (0%)<br>0 (0%) | NA |
| | | Adult OA<br>Paediatric OA | 23<br>5 | 0 (0%)<br>0 (0%) | NA |
| | Grade I | Adult PA<br>Paediatric PA | 7<br>34 | 0 (0%)<br>0 (0%) | NA |
| | | Total GBM<br>Total non-GBM | 408<br>376 | 43 (10.5%)<br>2 (0.5%) | <0.0001† |

*Fisher's two-tailed exact test between paediatric and adult groups.
†Fisher's two-tailed exact test between GBM group (including paediatric and adult) and lower grade astrocytomas (including grade I, II and III).

|  | No. scored | No. negative | % negative |
|---|---|---|---|
| ATRX | 113 | 40 | 35% |
| DAXX | 124 | 7 | 6% |
| ATRX and/or DAXX | 110 | 41* | 37% |

*Six samples have negative staining for both ATRX and DAXX.

Figure 3E

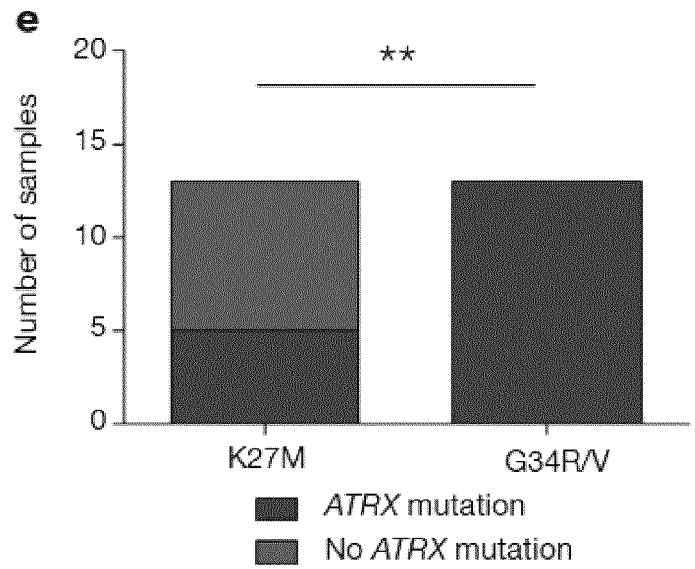

Figure 4A

| Pathway | Gene | pediatric GBM | | adult GBM | | p-value[¶] |
|---|---|---|---|---|---|---|
| | | No.of tumors | % of tumors | No.of tumors | % of tumors | |
| Chromatin Remodelling | H3F3A | 32/90 | 36 | 11/318 | 3 | <0.0001 |
| | ATRX | 59/190 | 31 | 23/161 | 14 | 0.0002 |
| | DAXX | 2/69 | 3 | 0/217* | 0* | 0.0576 |
| | IDH1 | 8/83 | 10 | 24/221 | 11 | 0.8367 |
| Cell Signalling | EGFR | 2/48 | 4 | 35/221 | 16 | 0.0362 |
| | PDGFRA | 4/48 | 8 | 4/116 | 3 | 0.234 |
| | NF1 | 13/48 | 27 | 36/221 | 16 | 0.0979 |
| | PIK3CA | 3/48 | 6 | 16/221 | 7 | 1 |
| | PIK3R1 | 5/48 | 10 | 18/221 | 8 | 0.575 |
| | PTEN | 3/48 | 6 | 54/221 | 24 | 0.0034 |
| Cell Cycle | TP53 | 26/48 | 54 | 73/221 | 33 | 0.008 |
| | CDKN2A | 3/48 | 6 | 0/22 | 0 | 0.5467 |
| | RB1 | 5/48 | 10 | 15/221 | 7 | 0.3694 |

[¶]Fisher's two-tailed comparison test for pediatric and adult GBM.
*105 of 217 samples were sequenced without DAXX mutation reported, 112 of 217 samples don't have DAXX mutation Figure 5E
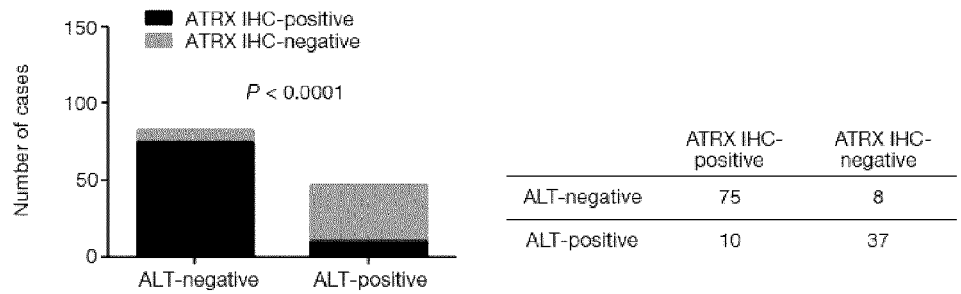
Figure 6A
Figure 6B
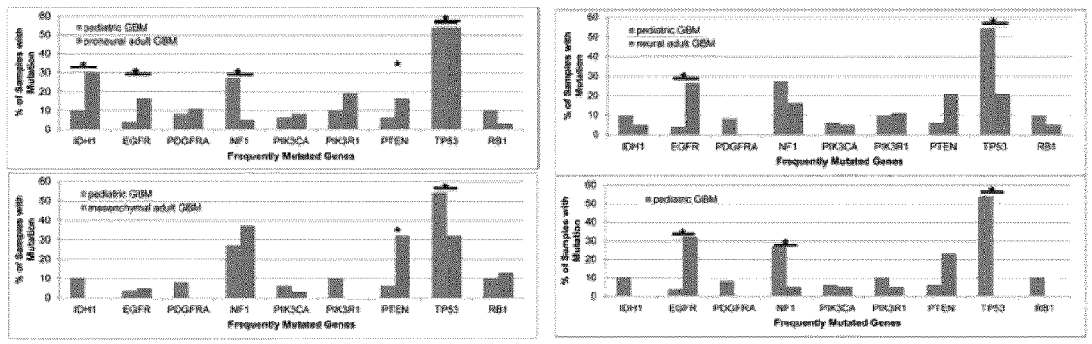

| | CDKN2A | MDM2 | TP53 | CDK4 | CDK6 | RB1 | EGFR | PDGFRA | NF1 | PIK3CA | PIK3R1 | PTEN |
|---|---|---|---|---|---|---|---|---|---|---|---|---|
| Type | DEL | AMP | DEL | AMP | AMP | DEL | AMP | AMP | DEL | AMP | DEL | DEL |
| # aGBM[14]/n | 114/206 | 22/206 | 2/206 | 29/206 | 3/206 | 6/206 | 88/206 | 22/206 | 4/206 | 4/206 | 0/206 | 16/206 |
| % aGBM[14] | 55 | 11 | 1 | 14 | 1 | 3 | 43 | 11 | 2 | 2 | 0 | 8 |
| # pGBM/n | 4/31 | 0/31 | 0/31 | 0/31 | 2/31 | 0/31 | 2/31 | 3/31 | 0/31 | 1/31 | 0/31 | 1/31 |
| % pGBM | 13 | 0 | 0 | 0 | 6 | 0 | 6 | 10 | 0 | 3 | 0 | 3 |
| p-value | <0.0001 | NS | NS | 0.0185 | NS | NS | <0.0001 | NS | NS | NS | NS | NS |

US 9,494,591 B2

MUTATIONS OF HISTONE PROTEINS ASSOCIATED WITH PROLIFERATIVE DISORDERS

CROSS-REFERENCE TO RELATED APPLICATIONS AND DOCUMENTS

This application claims priority on U.S. provisional application 61/562,204 filed on Nov. 21, 2011 as well as on U.S. provisional application 61/564,390 fled on Nov. 29, 2011. The content of these priority applications is herewith incorporated in their entirety.

This application contains a sequence listing submitted herewith electronically. The content of this electronic submission is incorporated by reference in this application.

FIELD OF THE INVENTION

The present application shows that non-conservative substitutions in histone proteins (such as the H3.3 encoded by the H3F3a gene) are associated with proliferation-associated disorders, such as cancer. This novel class of non-conservative histone proteins can be used for diagnostic and prognostic applications, provide a basis for therapeutic applications and enable the screening of the usefulness of agents for the prevention, treatment and/or alleviation of symptoms associated to the disorder.

BACKGROUND

Brain tumors are currently the leading cause of cancer-related mortality and morbidity in children. Glioblastoma multiforme (GBM) is a highly aggressive brain tumor and the first cancer to be comprehensively profiled by The Cancer Genome Atlas (TCGA) consortium. While GBM is less common in a pediatric setting than in adults, affected children show dismal outcomes similar to adult patients, and the vast majority will die within a few years of diagnosis despite aggressive therapeutic approaches. Tumors arise de novo (primary GBM) and are morphologically indistinguishable from their adult counterparts. A number of comprehensive studies have identified transcriptome-based subgroups and indicator mutations in adult GBM, and have thus enabled its molecular sub-classification. In contrast, while it has been demonstrated the presence of distinct molecular subsets of childhood GBM and described different genetic alterations compared to adult cases, the pediatric disease remains understudied. There is currently insufficient information to improve disease management, and since conventional treatments universally fail, there is a crucial need to identify relevant targets for the design of novel therapeutic agents.

It would be highly desirable to be provided with a biological marker for the prognostic and diagnostic of proliferation-associated disorders such as cancer. It would also be highly desirable to be provided with a potential candidate target for evaluating the usefulness of agents in the prevention, treatment and/or alleviation of symptoms associated with a proliferation-associated disorder. It would further be desirable to be provided with a novel therapy for the prevention, treatment and/or alleviation of symptoms associated with a proliferation-associated disorder.

BRIEF SUMMARY

The present application concerns the relationship between the presence of variations in amino acid sequence of histone proteins in subjects afflicted with a proliferation-associated disorder. This relationship provides a rationale for supporting diagnostic, prognostic and theranostic applications in which those variations are used as predictive markers. This relationship further provides a rationale for supporting therapeutic applications for the prevention and/or treatment of the proliferation-associated disorders. This relationship also provides a rationale for the screening of therapeutic agents for the treatment and/or prevention of proliferation-associated disorders.

In accordance with a first aspect, the present application provides a polypeptide having the amino acid sequence of SEQ ID NO: 6, SEQ ID NO: 7 or SEQ ID NO: 8. In an embodiment, the polypeptide has or consists of the amino acid sequence of SEQ ID NO: 1, SEQ ID NO: 2, SEQ ID NO: 3 or SEQ ID NO: 4. There is also provided a fragment of the polypeptide of claim 1 or 2, wherein the fragment is recognized by an antibody (i) specific for the H3.3 polypeptide having the SEQ ID NO: 1, SEQ ID NO: 2, SEQ ID NO: 3, SEQ ID NO: 4, SEQ ID NO: 6. SEQ ID NO: 7 and/or SEQ ID NO: 8 and (ii) lacking specificity towards SEQ ID NO: 5. There is further provided a polynucleotide encoding the polypeptide or the fragment described herein. There is also provided an antibody (in an embodiment a monoclonal antibody) which specifically recognized the H3.3 polypeptides described herein.

In accordance with a second aspect, the present application provides a method of assessing the disease status of a proliferation-associated disorder in a subject. Broadly, the method comprises: (a) providing a biological sample from the subject containing a H3.3 polypeptide or a H3.3-encoding polynucleotide; (b) determining the sequence identity of the H3.3 polypeptide or the encoded H3.3 polypeptide at a residue corresponding to position 27 and/or 34 of SEQ ID NO: 5; and (c) characterizing the subject based on such determination. The subject is characterized has having a poor disease status if the sequence identity of the H3.3 polypeptide or the encoded H3.3 polypeptide at the residue corresponding to position 27 is different from a lysine and/or at the residue corresponding to position 34 is different from a glycine. In an embodiment, the disease status is a predisposition to the proliferation-associated disorder and the poor disease status is associated with an increased likelihood of the proliferation-associated disorder in the subject. In another embodiment, the disease status is a diagnosis of the proliferation-associated disorder and the poor disease status is associated with the presence of the proliferation-associated disorder in the subject. In yet another embodiment, the disease status is a sub-classification of the proliferation-associated disorder and the poor disease status is associated with the association of the subject with a more aggressive class of the proliferation-associated disease. In still another embodiment, the disease status is a re-occurrence of the proliferation-associated disorder and the poor disease status is associated with the re-occurrence of the proliferation-associated disorder in the subject. In yet another embodiment, the subject has received at least one dose of an adjuvant therapy. In still another embodiment, the method further comprises determining the presence of a methionine residue corresponding to position 27. In yet another embodiment, the method further comprises determining the presence of an arginine residue corresponding position 34. In still another embodiment, the method further comprises determining the presence of a valine residue corresponding to position 34. In an embodiment, the proliferation-associated disorder is cancer, and in still another embodiment the cancer is a glioma (such as, for example, a glioblastoma multiforme and/or a diffuse intrinsic pontine glioma). In still another embodiment, the subject is less than 20, lees than 18, less than 16, less than 14 or less than 12 years of age.

In a third aspect, there is provided a kit for the assessment of a disease status of cancer in a subject. The kit can comprise a reagent capable of specifically recognizing a H3.3 polypeptide having an amino acid different from a lysine at a location corresponding to position 27 of SEQ ID NO: 5 and/or the H3.3 polypeptide having an amino acid residue different from a glycine at a location corresponding to position 34 of SEQ ID NO: 5. Alternatively (or in combination), the kit can comprise a H3.3-encoding polynucleotide encoding H3.3 polypeptide having an amino acid different from a lysine at a location corresponding to position 27 of SEQ ID NO: 5 and/or the H3.3 polypeptide having an amino acid residue different from a glycine at a location corresponding to position 34 of SEQ ID NO: 5. In one embodiment, the reagent comprises a first antibody or a fragment thereof capable of specifically recognizing the H3.3 protein having the amino acid different from a lysine at a location corresponding to position 27 of SEQ ID NO: 5, for example, the H3.3 polypeptide having a methionine residue at a location corresponding position 27 of SEQ ID NO: 5. In another embodiment, the reagent comprises a second antibody or fragment thereof capable of specifically recognizing the H3.3 polypeptide having the amino acid residue different from a glycine at a location corresponding to position 34 of SEQ ID NO: 5, for example, the H3.3, polypeptide having an arginine and/or a valine residue at a location corresponding to position 34 of SEQ ID NO: 5. In an embodiment, the reagent comprises a first probe capable of hybridizing to a first polynucleotide encoding the H3.3 polypeptide having the amino acid different from a lysine at a location corresponding to position 27 of SEQ ID NO: 5, for example, a first polynucleotide encoding the H3.3 polypeptide having a methionine residue at a location corresponding position 27 of SEQ ID NO: 5. In still another embodiment, the reagent comprises a second probe capable of hybridizing to a second polynucleotide encoding the H3.3 polypeptide having the amino acid residue different from a glycine at a location corresponding to position 34 of SEQ ID NO: 5, for example, a second polynucleotide encoding the H3.3, protein having an arginine and/or a valine residue at a location corresponding to position 34 of SEQ ID NO: 5.

In a fourth aspect, the present application provides a method of preventing, treating and/or alleviating the symptoms associated with a proliferation-associated disorder in a subject in need thereof. Broadly, the method comprises increasing the proportion of a wild-type H3.3 with respect to a non-conservative H3.3 variant in a tumor so as to prevent, treat and/or alleviate the symptoms associated with the proliferation-associated disorder in the subject. In an embodiment, the method further comprises administering to the subject a polynucleotide encoding the polypeptide of SEQ ID NO: 5 and/or the polypeptide of SEQ ID NO: 5. Various embodiments of the proliferation-associated disorder have been described above and do apply herein.

In a fifth aspect, the present application provides an H3.3-based agent for the prevention, treatment and/or alleviation of symptoms associated with a proliferation-associated disorder in a subject, wherein the agent increases the proportion of a wild-type H3.3 with respect to a non-conservative H3.3 variant in a tumor. In an embodiment, the H3.3-based agent is a polypeptide of SEQ ID NO: 5 and/or a H3.3-encoding polynucleotide encoding the polypeptide of SEQ ID NO: 5. Various embodiments of the proliferation-associated disorder have been described above and do apply herein.

In a sixth aspect, the present application provides a method for the screening of agents useful in the prevention, treatment and/or alleviation of symptoms of a proliferation-associated disorder. Broadly, the method comprises combining the agent with an H3.3-based reagent; measuring a parameter of the H3.3-based reagent in the presence of the agent to provide a test value; comparing the test value with a control value to determine if the test value is higher than, equal to or lower than the control value, wherein the control value is associated with a lack of prevention, treatment and/or alleviation of symptoms of the proliferation-associated disorder characterizing the usefulness of the agent based on the comparison. In an embodiment, the H3.3-based reagent is a wild-type H3.3-based reagent. In yet another embodiment, the agent is considered useful in the treatment, prevention and/or alleviation of symptoms of the proliferation-associated disorder when the test value is higher than the control value. In still another embodiment, the H3.3-based reagent is a non-conservative H3.3 variant-based reagent. In another embodiment, the agent is considered useful in the treatment, prevention and/or alleviation of symptoms of the proliferation-associated disorder when the test value is lower than the control value. In still a further embodiment, the H3.3-based reagent is an H3.3 polypeptide. In another embodiment, the parameter of the H3.3-based reagent is the level of expression of the H3.3 polypeptide. In yet another embodiment, the H3.3-based reagent is a polynucleotide encoding an H3.3 polypeptide. In still another embodiment, the parameter of the H3.3-based reagent is the level of expression of the polynucleotide encoding the H3.3 polypeptide. In an embodiment, the H3.3-based reagent is in a cell, such as, for example, a glial cell. Various embodiments of the proliferation-associated disorder have been described above and do apply herein.

BRIEF DESCRIPTION OF THE DRAWINGS

Having thus generally described the nature of the invention, reference will now be made to the accompanying drawings, showing by way of illustration, a preferred embodiment thereof, and in which:

FIGS. 1A, 1B, 1C and 1D show the most frequently identified mutations in pediatric GBM. (A) Most frequent somatic mutations in 48 pediatric glioblastoma tumors. * Mutations in bold and marked with * appear to be homozygous. ⁌ Sample PGBM19 additionally has a DAXX mutation C629Sfs, while PGBM21 has no ATRX mutation but has the DAXX mutation shown. ‡ Sample PGBM22 has a third ATRX mutation, p.D2136N, and a third NF1 mutation, p.A887T. Mutations identified in genes listed in this table were confirmed by Sanger sequencing, and were not present in dbSNP nor in the 1000 genomes dataset (October 2011), except for the TP53 SNP at R273, which has been previously associated with cancer. Detailed description of the mutations in affected samples is provided in Table 5. (B) Three recurrent non-synonymous single nucleotide variants (SNVs) were observed in H3F3A. A schematic representation of the K27M, G34R and G34V mutations is shown in the context of the common post-translational modifications of the H3.3 N-terminal fail (amino acids 1-40 of SEQ ID NO: 5), which regulates the histone code and histone functions. Mammalian cells express three major three of non-centromeric histone H3 variants, H3.1, H3.2, and H3.3. H3.3 has 136 amino acids, and is highly conserved across all eukaryotes. The amino acid sequence shows high conservation across species and from mammals to plants, including the residues subject to mutation in pediatric GBM (see multiple alignment of amino acids 11 to 60, SEQ ID NO: 14 for *H. sapiens* H3F3A, *H. sapiens* H3F3B, *M. musculus* H3F3c and *D. melanogaster* His3.3B; SEQ ID NO: 15 for *H. sapiens* HIST1H3A, SEQ ID NO: 16 for *S. pombe* Hht3; SEQ ID NO: 17 for *A. thaliana* AT1G13370). (C) Schematic representation of the missense mutations, frameshift deletions and stopgain SNVs observed in ATRX in the 48 whole exome sequencing WES samples. (D) Schematic of the overlap between mutations affecting ATRX-DAXX (observed in 15 samples). H3F3A (observed in 15 samples) and TP53 (observed in 26 samples). Eight samples had mutations in the three genes.

FIGS. 2A, 2B and 2C provide a correlation of ATRX mutation and tack of protein expression in pediatric GBM samples. Immunohistochemical staining of ATRX in samples analyzed by whole exome sequencing shows correlation between ATRX negative staining in tumor cells and presence of an ATRX mutation. ATRX is expressed in two samples with wild-type ATRX following whole exome sequencing (A for sample PGBM27 and B for PGBM26). ATRX is not expressed in PGBM14 (C) where mutations in ATRX were identified following whole exome sequencing.

FIGS. 3A, 3B, 3C, 3D and 3E. (A) H3F3A mutations in a set of 784 gliomas from all ages and grades. Sanger sequencing was performed on DNA obtained from patients with low grade (I and II) and high grade (III and IV) gliomas from several countries in Europe and from Canada and shows that H3F3A mutations are exclusive to high grade tumors and the vast majority occur in glioblastoma (GBM) and in the pediatric setting. O: oligodendroglioma, AO: anaplastic oligodendroglioma. OA: oligoastrocytoma, AOA: anaplastic oligoastrocytoma, A: diffuse astrocytoma grade II. AA: anaplastic astrocytoma, PA; pilocytic astrocytoma. (B) H3.3 mutations are specific to pediatric and young adult glioblastoma (GBM). Schematic representation of the occurrence of H3.3 mutations across age groups shows that K27M mutations occur mainly in younger patients (median age 11 years) and G34R/V mutations occur in older children and young adults (median age 20 years). No mutations were identified in older patients with GBM. (C) Comparison of the most frequently mutated genes in pediatric and adult GBM shows that H3F3A, ATRX and DAXX mutations are largely specific to pediatric disease. Except for similarities in the mutation rate for TP53 and PDGFRα with the previously identified proneural adult GBM subgroup, the rate and type of genes mutated were distinct between pediatric and adult GBM whatever the molecular subgroup (FIG. 4). (D) ATRX and DAXX immunohistochemical staining of a pediatric GBM tissue microarray (TMA) comprising 124 samples. View of the TMA slide and an example of a negative and of a positive core at high magnification to show specific nuclear staining (or lack thereof) for DAXX and ATRX. No gender bias for ATRX loss was observed. Overall survival and progression-free survival were similar in patients with and without loss of ATRX and/or DAXX (data not shown). (E) Differential association of K27M and G34R/V H3F3A mutations with ATRX mutations. G34R/V-H3.3 mutations were always associated with ATRX mutations, while a non significant overlap was observed for K27M (two-sided Fisher's exact test, p=0.0016).

FIGS. 4A and 4B show that pediatric GBM is molecularly distinct from the four molecular subgroups previously identified in adult GBM. (A) Comparison of the mutation rate of the previously identified most frequently mutated genes in adult glioblastoma to pediatric glioblastoma shows that pediatric GBM mutational profile does not overlap with any of the previously described four molecular adult GBM molecular subgroups. Similarities to the pro-neural subgroup include TP53 and PDGFRα mutations, however clear differences exist for IDH mutations and NF1 mutations that occur at respectively a much lower frequency and higher frequency in children. (B) Bar graph showing percentage of sample with mutations in function of genes. For each gene, pediatric GBM tumors (bar on the right side) are compared to adult GBM tumors (bar on the left side). *indicates statistical significance.

FIGS. 5A, 5B, 5C, 5D, and 5E. (A) Lysine 36 is methylated in a G34V mutant (GBM 14). Cell lysates from GBM14 (which harbours G34V mutation) and from GBM24, a pediatric GBM cell line (SF188) and normal human astrocytes (NHA; all wild type for H3.3) were analyzed, with a Western blot, with antibodies recognizing the three methylated forms of K36 and the methylated form of K27. Even though we cannot differentiate H3.3K36me3 from global H3K36me3 levels, results indicate increased methylation of K36 me1, me2 and me3 in the sample carrying the G34V mutation. (B) Unsupervised hierarchical clustering of 27 of the GBM samples analyzed by whole exome sequencing shows that K27M and G34R/V H3.3 mutants have specific gene expression profiles. Gene expression profiles were generated on Affymetrix U133PLUS2.0™ arrays. Clustering was based on the top 100 genes by standard deviation from autosomal genes detected as present in >10% of samples, and showed a clear distinction between K27M and G34R/V mutant cases. (C) Genes involved in development and differentiation show H3.3 mutation-specific expression patterns. Analysis for enrichment of Gene Ontology (GO) terms amongst the top differentially-expressed genes revealed 'Multicellular Organismal Development' (GO:0007275) to be the most highly enriched category (17/99 recognised gene IDs, p=0.01). Several of these show H3.3 mutation-specific expression patterns. Results ($\log_2$ expression in function of K27 mutants, G34 mutants and H3.3 wild-type) are shown for the MYT1 gene (top left panel), SFRP2 gene (top right panel), FZD7 (lower left panel) and DLX2 (lower right panel), * and ** indicates statistical significance. (D) Alternate lengthening of telomere is associated with the presence of mutant H3F3A/ATRX/P53 in pediatric GBM. We assessed ALT using two surrogate markers: Telomere-specific fluorescence in situ hybridization (normal glia, left panel; ALT negative, middle panel and ALT positive, right panel as well as in FIG. 6) and telomere-specific Southern blotting of high molecular weight genomic DNA (FIG. 7). Both methods show ALT to be associated with mutant H3F3A, ATRX and TP53. Representative images of ALT positive and negative staining of a pediatric GBM tissue microarray and a control brain are provided (upper panel). (E) Histogram and corresponding table comparing the number of ATRX IHC-positive (black) and ATRX IHC-negative (grey) in ALT-negative and ALT-positive individuals.

FIGS. 6A and 6B. Comparison of frequently mutated genes indicates that pediatric GBM is distinct from the four previously identified molecular subgroups in adult GBM. (A) Comparison of gene expression (associated with various pathways) in pediatric GBM as well as in four subgroups of adult GBM (proneural, neural, classical and mesenchymal). Dark blue indicates mutations in H3F3A. ATRX and DAXX we identified in this study and show to be specific to pediatric GBM. IDH1 (light blue) mutations have already been previously shown to be representative of a subgroup of adult GBM (proneural) and not pediatric GBM. Mutations in PDGFRA and TP53 had similar rates to adult proneural GBM while NF1 and RB1 mutations were more similar to mesenchymal subgroup (colored in green). (B) Bar graphs representative of the rate of mutations for specific genes (IDH1, EGFR, DGFRA, NF1, PIK3CA, PIK3R1, PTEN, TP53, RB1) between pediatric GBM and the proneural (top left graph), mesenchymal (lower left graph), neural (top right graph) and classical (lower right graph) adult GBM. For each gene in each graph, mutation rate of pediatric GBM is shown as the left bar while the mutation rate for the adult GBM is shown as the right bar. * indicates statistically significance as measured by the Fisher t-test (p<0.05).

Figure 16:
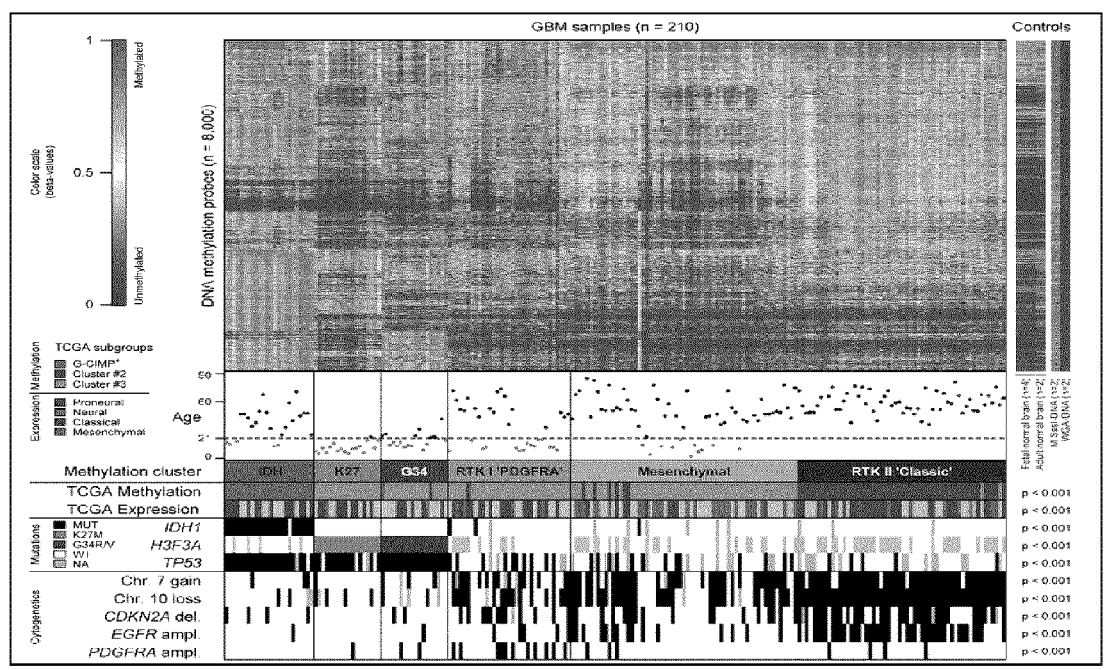

FIG. 16. Methylation profiling reveals the existence of six epigenetic GBM subgroups. Heatmap of methylation levels in six GBM subgroups identified by unsupervised k-means consensus clustering, and control samples as indicated.

Figure 17:
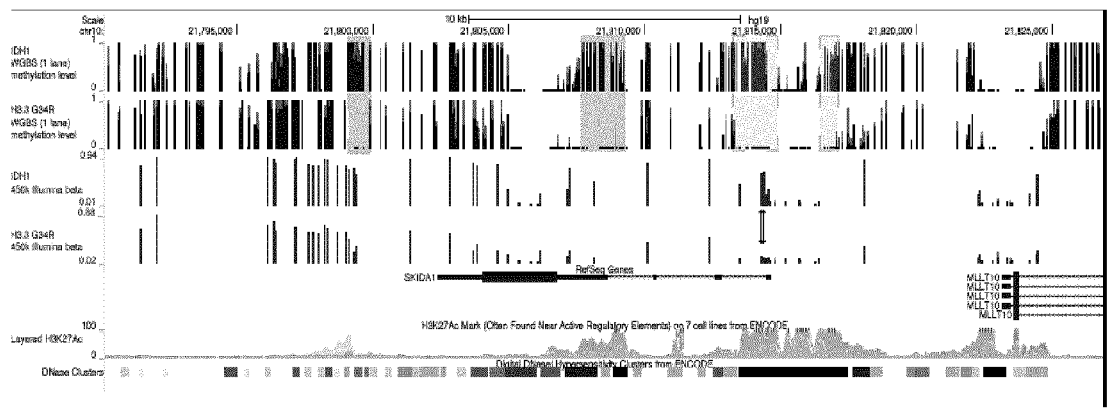

FIG. 17. Whole genome bisulphite sequencing (WGBS) compared to Illumina 450K Human Methylation array data. A region in chromosome 10 showing classifying difference in methylation (from 450K unsupervised clustering analyses) between major mutation types is highlighted. We carried out methylation quantitation from WGBS in IDH1 (top track) and H3.3 G34R (second track from top) mutation carrying tumors in parallel with 450K assay (3rd and 4th track). Despite low coverage (3-4× genome-wide in this pilot experiment) the correlation between 450K and WGBS IS HIGH at identical CpGs. Advantages offered by WGBS are highlighted at four putative regulatory elements (in blue for promoter distal elements, and in pink for promoter associated elements) for SKID1 gene. A highly significant difference between tumor types was observed for only 2 CpG sites in 450K analyses (promoter associated region, highlighted by arrows), whereas WGBS shows complete hypo vs. hypomethylation between H3.3 G34R and IDH1 harboring tumors at multiple regulatory regions showing active enhancer/promoter mark (H3K27ac) and DNaseI hypersensitivity in ENCODE cell lines. The high resolution and coverage of WGBS allows "indexing" of putative regulatory elements differing between tumors supporting integrative analyses of regulatory differences and gene networks perturbed by pediatric HGA associated mutations.

Figure 18:
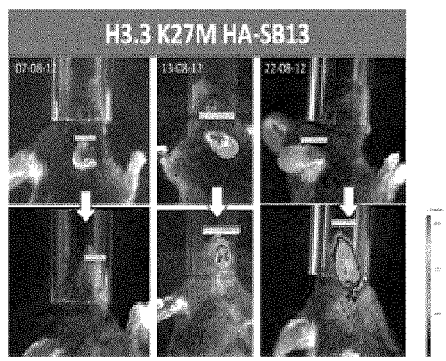

FIG. 18. Tumors arising in the brain of K27MH3.3 Injected mice (SB model) monitored using the built in luciferase (green indicative of increased cellular activity, color scale provided) indicative that K27MH3.3 is oncogenic by itself and promotes tumor formation.

DETAILED DESCRIPTION

Definitions

Throughout this application, various terms are used and some of them are more precisely defined herein.

Agonist. This term, as used herein, refers to an agent that mimics or upregulates (e.g., increases, potentiates or supplements) the expression and/or activity of a wild-type H3.3 protein (having the amino acid sequence as set forth in SEQ ID NO: 5). An agonist can be the wild-type protein itself and/or a nucleic acid molecule encoding the wild-type protein. An agonist can also be a compound that upregulates expression of a wild-type h3.3 gene or which increases at least one activity of a wild-type H3.3 protein. An agonist can also be a compound which increases the biological activity of the wild-type H3.3 protein via direct interaction, e.g. a binding partner.

Biological sample. A biological sample is a sample of an individual's bodily fluid, cells or tissues. The biological sample comprises either a H3.3 polypeptide and/or a polynucleotide encoding the H3.3 polypeptide. In this present application, the biological sample can be derived from a tumor tissue and may even comprise tumor cells. Alternatively or in combination, the biological sample can be derived from the individual's bodily fluid (such as blood, for example plasma or cerebrospinal fluid). In an embodiment, the biological sample comprises a cell having a H3.3 polypeptide and/or a polynucleotide encoding the H3.3 polypeptide. In another embodiment, the biological sample is a cell-free DNA/RNA sample having a H3.3 a polynucleotide encoding the H3.3 polypeptide. The biological sample can be used without prior modification in the various methods described herein. Optionally, the biological sample can be treated (mechanically, enzymatically, etc.) prior to the assays described herein. In one embodiment, the microvesicles from the biological sample are obtained and used in the assays described herein. Exemplary methods for obtaining microvesicles are described in WO 2012/051622.

H3.3. The H3.3 polypeptide (also referred to Histone 3) is a regulator of chromatin configuration and is encoded by the H3F3A gene. The GenBank accession number of the human mRNA sequence of this polypeptide is NM_002107. The GenBank accession number of the human polypeptide sequence of this protein is NP_002098 It is worth noting that the protein is post-translationally modified to remove the first methionine residue presented in the GenBank listing. There are at least two copies of the H3F3A gene in the human genome, which differ in their nucleotide sequence but produce proteins with the identical amino acid sequence. As known in the art, histone H3 is one of the five main histone proteins involved in the structure of chromatin in eukaryotic cells. Featuring a main globular domain and a long N-terminal tail, H3 is involved with the structure of the nucleosomes of the "beads on a string" structure. Histone H3 is the most extensively modified of the five known histones. The N-terminal tail of histone H3 protrudes from the globular nucleosome core and can undergo several different types of post-translational modification that influence cellular processes. These modifications include the covalent attachment of methyl or acetyl groups to lysine and arginine amino acids and the phosphorylation of serine or threonine.

Pharmaceutically effective amount or therapeutically effective amount. These expressions refer to an amount (dose) effective in mediating a therapeutic benefit to a patient (for example prevention, treatment and/or alleviation of symptoms of a proliferation associated disorder). It is also to be understood herein that a "pharmaceutically effective amount" may be interpreted as an amount giving a desired therapeutic effect, either taken in one dose or in any dosage or route, taken alone or in combination with other therapeutic agents.

Pharmaceutically acceptable salt. This expression refers to conventional acid-addition salts or base-addition salts that retain the biological effectiveness and properties of the therapeutic agent described herein. They are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as e.g., tetramethylammonium hydroxide. The chemical modification of an agent into a salt is a well known technique which is used in attempting to improve properties involving physical or chemical stability, e.g., hygroscopicity, flowability or solubility of compounds.

Prevention, treatment and alleviation of symptoms. These expressions refer to the ability of a method or an agent to limit the development, progression and/or symptomology of a proliferation-associated disorders. Broadly, the prevention, treatment and/or alleviation of symptoms can encompass the reduction of proliferation of the cells (e.g. by reducing the total number of cells in an hyperproliferative state and/or by reducing the pace of proliferation of cells). Symptoms associated with proliferation-associated disorder include, but are not limited to: local symptoms which are associated with the site of the primary cancer (such as lumps or swelling (tumor), hemorrhage, ulceration and pain), metastatic symptoms which are associated to the spread of cancer to other locations in the body (such as enlarged lymph nodes, hepatomegaly, splenomegaly, pain, fracture of affected bones, and neurological symptoms), and systemic symptoms (such as weight loss, fatigue, excessive sweating, anemia and paraneoplastic phenomena).

Proliferation-associated disorders. These disorders form a class of diseases where cells proliferate more rapidly, and usually not in an ordered fashion. The proliferation of cells cause an hyperproliferative state that may lead to biological dysfunctions, such as the formation of tumors (malignant or benign). One of the proliferation-associated disorder is cancer. Also known medically as a malignant neoplasm, cancer is a term for a large group of different diseases, all involving unregulated cell growth. In cancer, cells divide and grow uncontrollably, forming malignant tumors, and invade nearby parts of the body. The cancer may also spread to more distant parts of the body through the lymphatic system or bloodstream. In an embodiment, the cancer is a glioma (e.g. a cancer of the gial cells located in the brain or spine). In another embodiment the cancer is associated with the involvement of isocitrate dehydrogenase or IDH (such as, for example, breast cancer, acute myeloid leukemia, chronic myeloid leukemia). IDH mutations occur in a variety of cancers of the central nervous system: adult low grade gliomas, secondary glioblastoma as well as oligodendrogliomas. IDH mutations also occur in acute myeloid leukemia, myelodysplastic syndroms and myeloproliferative neoplasms, gliomas and, at lower frequencies, in prostate cancer, acute lymphoblastic leukemia and breast cancer.

Reaction vessel. The reaction vessel is a discrete unit where a biological sample comprising a H3.3-based reagent (H3.3 polypeptide or polynucleotide encoding same) is placed. The reaction vessel also includes the discrete unit where the agent is combined with the H3.3-based reagent, and it can be an in vitro or in vivo environment. Suitable in vitro environments can include, for example, a cell-free environment where a H3.3-based reagent is combined in a reaction media comprising the appropriate reagents to enable the assessment of the parameter associated with H3.3 to be monitored.

Whole exome sequencing. This sequencing technique refers to the determination of nucleotide sequences of exons in individuals. As shown below, this technique was successfully used to identify variations in the H3.3 amino acid sequence that were associated with a proliferation-associated disorder.

H3.3 Non-Conservative Variants

The present application provides novel non-conservative variants of H3.3 whose expression is associated with proliferative disorder. More specifically, the non-conservative H3.3 variants are expressed in cells and tissues afflicted by the proliferative disorder. The non-conservative variants are distinct in at least one of two positions when compared to the wild-type H3.3 protein (whose sequence is presented in SEQ ID NO: 5). Some of specific non-conservative variants presented herewith are encoded at the following chromosomic regions: chr1:226252135, chr1:226252155 and chr1:226252156.

A first non-conservative H3.3 variant (e.g. SEQ ID NO: 6) concerns a polypeptide having a residue different from lysine at a location corresponding to position 27 of the wild-type H3.3. It is known that the lysine at position 27 of the wild-type H3.3 protein is capable of being methylated. This first non-conservative H3.3 variant is preferably not being capable of being methylated at position 27. Consequently, the non-conservative H3.3 variant preferably does not bear a lysine or an arginine residue at position 27. Such non-conservative H3.3 variant can bear any other naturally occurring amino acid, and preferably a methionine residue (SEQ ID NO: 1) at position 27. In an embodiment, the first non-conservative H3.3 variant has or comprise the amino acid sequence of SEQ ID NO: 6 or SEQ ID NO: 1. In another embodiment, the first non-conservative H3.3 variant consists of the amino acid sequence of SEQ ID NO: 6 or SEQ ID NO: 1.

A second non-conservative H3.3 variant (e.g. SEQ ID NO: 7) concerns a polypeptide having a residue different from glycine at a location corresponding to position 34 of the wild-type H3.3. It is thought that the glycine at position 34 of the wild-type H3.3 protein does not interfere with the methylation of the lysine residue located at position 38. This second non-conservative H3.3 variant is preferably capable of interfering with the methylation of the lysine residue at position 34. Such non-conservative H3.3 variant can bear any naturally occurring amino acid other than a glycine, and, preferably, an arginine or valine residue (SEQ ID NO: 2 or SEQ ID NO: 3). In an embodiment, the second non-conservative H3.3 variant has or comprise the amino acid sequence of SEQ ID NO: 7, SEQ ID NO: 2 or SEQ ID NO: 3. In another embodiment, the second non-conservative H3.3 variant consists of the amino acid sequence of SEQ ID NO: 7, SEQ ID NO: 2 or SEQ ID NO: 3.

A third non-conservative H3.3 variant (e.g. SEQ ID NO: 8) concerns a polypeptide having a residue different from lysine at a location corresponding to position 27 of the wild-type H3.3 and a residue different from glycine at a location corresponding to position 34 of the wild-type H3.3. This third non-conservative variant preferably does not bear an arginine residue at position 26. An exemplary sequence of the third non-conservative variants bears a methionine residue at position 27 and an arginine or a valine residue at position 34 (as shown in SEQ ID NO: 4). In an embodiment, the third non-conservative H3.3 variant has or comprise the amino acid sequence of SEQ ID NO: 8 or SEQ ID NO: 4. In another embodiment, the third non-conservative H3.3 variant consists of the amino acid sequence of SEQ ID NO: 8 or SEQ ID NO: 4.

The present application also provides fragments of the non-conservative H3.3 variants described herein. These fragments contain less amino acids than the wild-type H3.3 but are recognized specifically by antibodies which fail to recognize the wild-type H3.3. In an embodiment, these fragments bear epitopes corresponding to positions 27 and/or 34 that are specifically recognized by antibodies which fail to recognize wild-type H3.3. These fragments encompass at least amino acid residues corresponding to positions 27 to 34. In an embodiment, the fragments are recognized by antibodies specific for SEQ ID NO: 6, SEQ ID NO: 7 or SEQ ID NO: 8 and that fail to specifically recognize the polypeptide presented in SEQ ID NO: 5. In another embodiment, the fragments are recognized by antibodies specific for SEQ ID NO: 1, SEQ ID NO: 2, SEQ ID NO: 3 or SEQ ID NO: 4 and that fail to specifically recognize the polypeptide presented in SEQ ID NO: 5.

Nucleic acid polynucleotide molecules are also contemplated herein and encodes the H3.3 non-conservative variants may be derived from a variety of sources including DNA, cDNA, synthetic DNA, synthetic RNA, derivatives, mimetics or combinations thereof. Such sequences may comprise genomic DNA, which may or may not include naturally occurring introns, genic regions, nongenic regions, and regulatory regions. Moreover, such genomic DNA may be obtained in association with promoter regions or poly (A) sequences. The sequences, genomic DNA, or cDNA may be obtained in any of several ways. Genomic DNA can be extracted and purified from suitable cells by means well known in the art. Alternatively, mRNA can be isolated from a cell and used to produce cDNA by reverse transcription or other means. The nucleic acids described herein are used in certain embodiments of the methods of the present invention for production of RNA, proteins or polypeptides, through incorporation into host cells, tissues, or organisms. In one embodiment, DNA containing all or part of the coding sequence for the H3.3 variant polypeptides are incorporated into vectors for expression of the encoded polypeptide in suitable host cells.

Antibodies (as well as antigen-binging fragment thereof) specific for the H3.3 non-conservative variants are also contemplated.

Predictive Methods and Associated Commercial Packages

The diagnostic and prognostic methods described herein are designed to capture the relationship between H3.3's amino acid identity (at specific positions) and proliferation-associated disorders to generate valuable information about the individual that is being tested. Once an individual has been diagnosed by one of the methods described herein, this individual can be treated according to the therapeutic regimen that is considered useful depending on its disease status.

In the diagnostic and prognostic applications, a biological sample is first provided from the subject that is being tested. In an embodiment, the biological sample comprises a subject's own cell. In another embodiment, the biological sample is cell-free DNA (cfDNA), which is thought to be released from dying cells, as DNA fragments or nucleosomes. CfDNA often maintains sequence and methylation characteristics of the parental cancer cells. Alternatively, oncogenic DNA, mRNA, miRNA and proteins may become a cargo of extracellular vesicles (EVs), which originate from viable cells as a product of exosome biogenesis or membrane blebbing. It was previously reported that oncogene containing EVs (oncosomes) are released at a high rate from glioma cells in vivo. These oncosomes may contain intact oncogenic EGFRvIII, and we showed it can exert biological effects upon intercellular transfer and similar observations were reported for other transforming protein, mRNA and DNA species. It is possible that what is known as cfDNA is also, at least in part, contained in oncosomes, as suggested by detection of c-MYC and G12V-H-Ras sequences in this material. EVs protect this material from degradation and preserve it in blood, thereby allowing remote access to the mutational status, functional state and identity of the cells of origin. Enrichment of this material in the EV compartment, as compared to total plasma, can offer an opportunity to increase the sensitivity of detection and multiplexing capacity.

In diagnostic and prognostic applications, a biological sample of an individual is placed in a reaction vessel. The biological sample comprises an H3.3 polypeptide (e.g. either an H3.3-encoding nucleic acid molecule and/or an H3.3 polypeptide). In the assays, the reaction vessel can be any type of container that can accommodate the determination of the nucleic/amino acid identity of the H3.3 polypeptide.

Once the biological sample has been placed in the reaction vessel, the amino acid sequence identity of the H3.3 polypeptide and/or the nucleic acid sequence identity of the H3.3-encoding nucleic acid molecule is determined. This assessment may be made directly in the reaction vessel (by using a probe) or on a sample of such reaction vessel. The determination of the sequence identity of the H3.3 polypeptide (either directly or via the H3.3-encoding molecule nucleic acid molecule) can be made either at the DNA level, the RNA level and/or the polypeptide level.

It is not necessary to determine the sequence identity of the complete H3.3 polypeptide and/or H3.3-encoding nucleic acid molecule. In the methods presented herein, it is important to determine the sequence identity of the H3.3 polypeptide and/or H3.3-encoding nucleic acid molecule in at least one of two positions. The first position corresponds to the amino acid residue 27 of the wild-type H3.3 protein (e.g. SEQ ID NO: 5). At this first position, the wild-type H3.3 protein presents a lysine residue. The second position corresponds to the amino acid residue 34 of the wild-type H3.3 protein (e.g. SEQ ID NO: 5). At this second position, the wild-type H3.3 protein presents a glycine residue. In an embodiment, the sequence identity is determined at one of the two positions (e.g. residue 27 or 34). In another embodiment, the sequence identity is determined at both positions (e.g. residue 27 and 34). In yet a further embodiment, the sequence identity can be first determined at one of the two positions (e.g. residues 27 or 34) and then determined at the other position (e.g. residues 27 or 34). As it will be appreciated by those skilled in the art, the determination of sequence identity can be made at the nucleic acid level and/or at the polypeptide level.

The determination step can rely on the addition of a qualifier specific to the sequence to be determined. The qualifier can, for example, specifically bind to a sequence or subsequence of amino acids of the H3.3 protein. In those instances, the association between the qualifier and the H3.3 protein can be used to provide the sequence identity of the H3.3 protein. For example, the qualifier can be an antibody or a fragment thereof capable of specifically recognizing a methionine at a position corresponding to residue 27 of the H3.3 protein. If a methionine residue is present at position corresponding to residue 27, the antibody will specifically bind to the H3.3 polypeptide in the reaction vessel and this association will indicate the presence of a methionine at a position corresponding to residue 27 in the H3.3 protein. In another embodiment, the qualifier can be an antibody or a fragment thereof that can specifically recognize a lysine residue at a position corresponding to residue 27 of the H3.3 protein. In such embodiment, specific binding between the antibody and the H3.3-based reagent indicates that the polypeptide bears a lysine residue at a position corresponding to residue 27. However, the absence of binding between this lysine-specific antibody and the H3.3 protein (in conditions where binding between the anti-lysine antibody and its cognate ligand would otherwise be observed), indicates that the H3.3 protein does not bear, at position 27, a lysine residue.

If the measurement of the parameter is performed at the nucleotide level, then the nucleic acid sequence of the H3.3 gene, transcript (e.g. mRNA) or corresponding cDNA can be assessed. Various methods of determining the nucleic acid sequence of a nucleic acid molecule are known to those skilled in the art and include, but are not limited to, chemical sequencing (e.g. Maxam-Gilbert sequencing), chain termination methods (e.g. Sanger sequencing, and dye-terminator sequencing), restriction digestion-based sequencing (e.g. RFLP), hybridization-based sequencing (e.g. DNA microarray, RNA micro array, Molecular Beacon probes, TaqMan probes), mass spectrometry-based sequencing, next generation sequencing (e.g. Whole exome sequencing. Massively Parallel Signature Sequencing or MPSS, Polony sequencing, pyrosequencing. Illumina (Solexa) sequencing, SOLID™ sequencing, ion semiconductor sequencing. DNA nanoball sequencing, HELIOSCOPE™ single molecule sequencing, SINGLE MOLECULE SMRT™ sequencing, Single Molecule real time (RNAP) sequencing, and Nanopore DNA sequencing). As indicated above, it is not necessary to sequence the complete nucleic acid molecule encoding the H3.3 protein, only the nucleic acid identity of the bases encoding the amino acid at a position corresponding to residues 27 and/or 34 is required.

If the measurement of the parameter is performed at the polypeptide level, an assessment of the amino acid identity of the H3.3 level of expression can be performed. In an embodiment, this determination can be done through an antibody-based technique (such as an Western Blot, FACS or an ELISA), a micro-array, mass spectrometry, protein sequencing, etc.

In addition, an assessment of H3.3 biological activity can be performed as an indirect indicator of amino acid sequence identity at positions corresponding to residues 27 and/or 34. H3.3 is a histone protein and its post-translational modifications influences its biological activity (e.g. regulation of gene expression). For example, in native wild-type H3.3 polypeptide, the lysine at position 27 can be methylated and, in return, this methylation modifies the biological activity of H3.3 (e.g. favors a closed chromatin configuration) and ultimately limits and/or lowers gene expression. In an H3.3 polypeptide bearing, at position 27 a residue different from a lysine (for example a methionine), methylation may be limited or reduced and as such H3.3 is not able of mediating its activity of limiting or shutting off gene expression. In another example, in native wild-type H3.3 polypeptide, the relatively small and uncharged glycine residue at position 34 does not prevent the recognition of the modified lysine at position 36 and, as such, favors a closed chromatin configuration. However, the presence of a relatively bulky arginine or a charged valine residue at position 34 probably prevents the recognition of the modified lysine at position 36 and limits the ability of H3.3 to mediate its biological activity. As such, it is also possible to determine the amino acid identity of the H3.3 protein by either measuring or determining the presence or absence of post-transcriptional modifications (such as methylation, citrullination, acetylation, phosphorylation, SUMOylation, ubiquitination, and/or ADP-ribosylation) at specific residues. It is also possible to determine the amino acid identity of the H3.3 protein by measuring the ability of the H3.3-based reagent to limit or suppress gene expression.

As known in the art, H3.3 forms a complex with the ATRX and DAXX proteins and such complex localizes H3.3 in the pericentric heterochromatin and telomeres regions. As shown herein, the mutations associated with H3.3 are associated with a lower expression of ATRX and DAXX as well as the absence of the complex when measured by histochemistry. Consequently, in a further assay format, H3.3's biological activity can be indirectly measured by quantifying the expression of ATRX and/or DAXX or by determining the presence or absence of the ATRX-DAXX-H3.3 complex in tumor tissues.

The interaction between more than one molecule can also be detected, e.g., using a fluorescence assay in which at least one molecule is fluorescently labeled. One example of such an assay includes fluorescence energy transfer (FET or FRET for fluorescence resonance energy transfer). A fluorophore label on the first "donor" molecule is selected such that its emitted fluorescent energy will be absorbed by a fluorescent label on a second "acceptor" molecule, which in turn is able to fluoresce due to the absorbed energy. Alternately, the "donor" protein molecule may simply utilize the natural fluorescent energy of tryptophan residues. Labels are chosen that emit different wavelengths of light, such that the "acceptor" molecule label may be differentiated from that of the "donor". Since the efficiency of energy transfer between the labels is related to the distance separating the molecules, the spatial relationship between the molecules can be assessed. In a situation in which binding occurs between the molecules, the fluorescent emission of the "acceptor" molecule label in the assay should be maximal. A FET binding event can be conveniently measured through standard fluorometric detection means well known in the art (e.g., using a fluorimeter).

Another example of a fluorescence assay is fluorescence polarization (FP). For FP, only one component needs to be labeled. A binding interaction is detected by a change in molecular size of the labeled component. The size change alters the tumbling rate of the component in solution and is detected as a change in FP.

In another embodiment, the measuring stop can rely on the use of real-time Biomolecular Interaction Analysis (BIA) "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In another assay format, H3.3's biological activity can be indirectly measured by quantifying the expression levels of its target genes whose expression is modulated by the presence and activity of the variant H3.3. Such genes can be, for example, those listed in Table 7.

Once the sequence identity has been determined, the information is extracted from the reaction vessel is compared to residues at corresponding positions in a control sequence (e.g. wild-type H3.3 or SEQ ID NO: 5). In diagnostic and prognostic application, it must be determined if the sequence of the H3.3 protein is identical or different from the wild-type sequence (e.g. SEQ ID NO: 5) at positions corresponding to residues 27 and/or 34. The presence of a discrepancy between the sequenced H3.3 protein and the wild-type sequence at positions corresponding to residues 27 and/or 34 is associated with a poor disease status. For example, if in the sample, it is determined that the residue corresponding to position 27 of the wild-type H3.3 is a methionine, then the comparison indicates that the tested H3.3 is different from the wild-type H3.3 (e.g. that the residue is not a lysine) and the individual is characterized as being associated with a poor disease status. In another example, if in the sample, it is determined that the residue corresponding to position 34 of the wild-type H3.3 is a an arginine or a valine, then the comparison indicates that the tested H3.3 is different from the wild-type H3.3 (e.g. that the residue is not a glycine) and the individual is characterized as being associated with a poor disease status.

In an embodiment, the comparison can be made by an individual. In another embodiment, the comparison can be made in a comparison module. Such comparison module may comprise a processor and a memory card to perform an application. The processor may access the memory to retrieve data.

The processor may be any device that can perform operations on data. Examples are a central processing unit (CPU), a front-end processor, a microprocessor, a graphics processing unit (PPU/VPU), a physics processing unit (PPU), a digital signal processor and a network processor. The application is coupled to the processor and configured to determine the presence or absence of a discrepancy between the sequence of tested H3.3 with respect to sequence of the wild-type H3.3. An output of this comparison may be transmitted to a display device. The memory, accessible by the processor, receives and stores data, such as sequence identity of the H3.3 protein (either directly or the encoded H3.3 from the nucleic acid molecule) or any other information generated or used. The memory may be a main memory (such as a high speed Random Access Memory or RAM) or an auxiliary storage unit (such as a hard disk, a floppy disk or a magnetic tape drive). The memory may be any other type of memory (such as a Read-Only Memory or ROM) or optical storage media (such as a videodisc or a compact disc).

Once the comparison between the sequence of the tested H3.3 protein and the wild-type H3.3 is made, then it is possible to characterize the Individual. This characterization is possible because, as shown herein, mutations of H3.3 at positions corresponding to residues 27 and/or 34 are associated with a poor disease status.

In an embodiment, the characterization can be made by an individual. In another embodiment, the characterization can be made with a processor and a memory card to perform an application. The processor may access the memory to retrieve data. The processor may be any device that can perform operations on data. Examples are a central processing unit (CPU), a front-end processor, a microprocessor, a graphics processing unit (PPU/VPU), a physics processing unit (PPU), a digital signal processor and a network processor. The application is coupled to the processor and configured to characterize the individual being tested. An output of this characterization may be transmitted to a display device. The memory, accessible by the processor receives and stores data, such as sequences of the tested H3.3 or any other information generated or used (such as the sequence identity of the wild-type H3.3). The memory may be a main memory (such as a high speed Random Access Memory or RAM) or an auxiliary storage unit (such as a hard disk, a floppy disk or a magnetic tape drive). The memory may be any other type of memory (such as a Read-Only Memory or ROM) or optical storage media (such as a videodisc or a compact disc).

The methods described herein are useful for determine the predisposition of an individual to a proliferation-associated disorder. As shown herein, the presence of variations at positions 27 and/or 34 of the H3.3 protein are associated with a population of individuals afflicted with a proliferation-associated disorder (e.g. cancer). As such, the determination of amino acid variations at positions 27 and/or 34 can be useful in predicting the likelihood of disease in tested individuals.

The methods presented herein can also be useful for diagnosing a proliferation-associated disorder in an individual. As shown herein, the presence of variations at positions 27 and/or 34 are associated with disease tissue of a population of individuals afflicted with a proliferation-associated disorder (e.g. cancer).

As further shown herein, even the variation occur within the afflicted tissue, it is possible to detect it in the blood stream of afflicted individuals. As such, the presence of amino acid residues variations at a location corresponding to positions 27 and/or 34 of the wild-type H3.3 can be useful in determining the presence or absence of the proliferation-associated disease in tested individuals.

The methods presented herein can also be useful in classifying individuals already diagnosed with a proliferation-associated disorder. As shown herein, the presence of variations at positions 27 and/or 34 are associated with the most aggressive forms of diseases (e.g. Grade III and Grade IV cancers). As such, the determination of amino acid variations at positions 27 and/or 34 can be useful in determining the grade of the disease and, optionally, this information can be used to optimize the therapeutic regimen.

The methods presented herein can also be useful in determining the re-occurrence of a proliferation-associated disorder in individuals previously diagnosed (and, optionally treated) with the disorder. As shown herein, the presence of variations at positions 27 and/or 34 are associated with the presence of an hyperproliferative tissue. As such, determination of the presence of amino acid variations at positions 27 and/or 34 can be useful in determining the presence or absence of the proliferation-associated disease in tested individuals and, optionally, this information can be used to optimize the appropriate therapeutic regimen. For example, if an individual has been treated up until the point where the variants of the H3.3 proteins could no longer be detected in its biological fluids, the methods described herein can be used to monitor the re-occurrence of the disease and this information can be further used to determine the necessity of treating the individual with, for example, an adjuvant therapy.

Optionally, the methods described herein can also include the determination of variations in other proliferation-associated disorder associated polypeptides. As shown herein, variations in sequence identity and/or expression of proteins associated with chromatin remodeling (such as, for example, ATRX, DAXX and IDH1) have been shown to be associated with poor disease status and as such can be used as complementary variations to confirm poor disease status. In an embodiment, the present methods are performed after the determination in variations in the IDH1 polypeptide has been performed. In another embodiment, variations in the H3.3 protein are first performed and then variations in the IDH1 polypeptide are characterized. Some of these variations are presented in Tables 3 and 5. In addition, variations in sequence identity of proteins associated with cell signaling (such as, for example, PDGFR1, EFGR, NF1, PIK3CA, PIK3R1 and PTEN) have also been shown to be associated with poor disease status (Table 6) and can be optionally used in the methods described herein. Some of these variations are presented in Table 5. Further, variations in sequence identity of proteins associated with cell cycle (such as, for example, P53, CDKN2A and RB1) have also been shown to be associated with poor disease status (Table 6) and can be optionally used in the methods described herein. Some of these variations are presented in Table 5.

The present application also provides diagnostic and prognostic systems for performing the characterizations and methods described herein. These systems comprise a reaction vessel for placing the biological sample, a processor in a computer system, a memory accessible by the processor and an application coupled to the processor. The application or group of applications is(are) configured for receiving a sequence identity of the H3.3 polypeptide (either directly or encoded by a H3.3-encoding nucleic acid); comparing the sequence identity to the sequence of a wild-type H3.3 (at positions 27 and/or 34) and/or characterizing the individual in function of this comparison.

The present application also provides a software product embodied on a computer readable medium. This software product comprises instructions for characterizing the individual according to the methods described herein. The software product comprises a receiving module for receiving a sequence identity of a H3.3 polypeptide (either directly or from a H3.3-encoding nucleic acid molecule) from a biological sample; a comparison module receiving input from the measuring module for determining if the sequence identity is identical to the sequence of a wild-type H3.3 protein; a characterization module receiving input from the comparison module for performing the characterization based on the comparison.

In an embodiment, an application found in the computer system of the system is used in the comparison module. A measuring module extracts/receives information from the reaction vessel with respect to the sequence identity of the H3.3 protein. The receiving module is coupled to a comparison module which receives the value(s) of the sequence identity of the H3.3 protein and determines if this value is identical or different from the sequence of a wild-type H3.3 protein. The comparison module can be coupled to a characterization module.

In another embodiment, an application found in the computer system of the system is used in the characterization module. The comparison module is coupled to the characterization module which receives the comparison and performs the characterization based on this comparison.

In a further embodiment, the receiving module, comparison module and characterization module are organized into a single discrete system. In another embodiment, each module is organized into different discrete system. In still a further embodiment, at least two modules are organized into a single discrete system.

Commercial packages. The present application also provides commercial packages or kits for assessing disease status of a proliferation associated disorder. The commercial package comprises reagents for detecting the sequence identity in at least one position corresponding to amino acid residues 27 and/or 34 of the wild-type H3.3 protein (SEQ ID NO: 5), in some embodiment, the reagent is an antibody or a combination of antibodies specific for either the wilt-type H3.3 polypeptide or the non-conservative H3.3, polypeptide. In another embodiment, the reagent is a probe or a combination of probes specific for a polynucleotide encoding either the wilt-type H3.3 polypeptide or the non-conservative H3.3, polypeptide.

Nucleic scid probes. The nucleic acid probes that can be used in the present methods and commercial packages are that can specifically detect a modification at the nucleic acid level which will result in a variation at positions corresponding to residues 27 and/or 34 of the wild-type H3.3 protein (SEQ ID NO: 5). In an embodiment, the probes can specifically hybridize to a nucleic acid sequence encoding the residues at positions 27 and/34 and binding provides information with respect to the sequence identity. Nucleic acid hybridization involves contacting a probe and target nucleic acid under conditions where the probe and its complementary target can form stable hybrid duplexes through complementary base paring. It is generally recognized that nucleic acids are denatured by increasing the temperature or decreasing the salt concentration of the buffer containing the nucleic acids. Under low stringency conditions (e.g., low temperature and/or high salt) hybrid duplexes (e.g., DNA: DNA, RNA:RNA, or RNA:DNA) will form even where the annealed sequences are not perfectly complementary. Thus, specificity of hybridization is reduced at lower stringency. Conversely, at higher stringency (e.g., higher temperature or lower salt) successful hybridization tolerates fewer mismatches. One of skill in the art will appreciate that hybridization conditions may be selected to provide any degree of stringency as described in Sambrook et al. (1989, Molecular Cloning: A Laboratory Manual, 2d Ed., Cold Spring Harbor Laboratory Press. Cold Spring Harbor, N.Y.). In some embodiments, high stringency hybridizations conditions can be observed when, once the nucleic acid probe and its target have been incubated, the complex is washed in a 0.1×SSC solution at 65° C.

Alternatively or in combination, the probes that are complementary to the H3.3-encoding polynucleotide or fragments thereof refer to oligonucleotides that are capable of hybridizing under stringent conditions to at least part of the nucleotide sequences of the H3.3-encoding polynucleotide. Such hybridizable oligonucleotides will typically exhibit at least about 75% sequence identity at the nucleotide level to said genes, preferably about 80% or 85% sequence identity or more preferably about 90%, 95%, 98% or more sequence identity to the H3.3-encoding polynucleotide.

In another embodiment, the probes can serve to amplify a fragment of the nucleic acid encoding the residues H3.3 protein at corresponding position 27 and/or 34. Such amplified fragment can then either be submitted to sequence or to hybridization to provide sequence identity.

Antibodies. The antibodies that can be used in the present methods and commercial packages are those that specifically recognize the epitopes created with the variations in amino acid identity at positions corresponding to residues 27 and/or 34 of the H3.3 protein. The antibodies can recognize either one or both epitopes. In an embodiment, the antibodies specifically recognize a methionine residue at a position corresponding to residue 27. In yet another embodiment, the antibodies specifically recognize an arginine or a valine residue at a position corresponding to residue 34. The antibodies can be polyclonal or monoclonal.

In an embodiment, the antibody does not specifically recognized the wild-type H3.3 polypeptide. In still another embodiment, the antibody specifically recognizes at least one of the non-conservative H3.3 variant polypeptides described herein. For example, the antibody specifically can recognize the non-conservative H3.3 variant having a residue different from lysine at a residue corresponding to position 27 of SEQ ID NO: 5. In such example, the antibody can specifically recognizes the non-conservative H3.3 variant having a methionine at a residue corresponding to position 27 of SEQ ID NO: 5. In another example, the antibody specifically can recognize the non-conservative H3.3 variant having a residue different from glycine at a residue corresponding to position 34 of SEQ ID NO: 5. In such example, the antibody can specifically recognizes the non-conservative H3.3 variant having an arginine or a valine at a residue corresponding to position 34 of SEQ ID NO: 5.

Naturally occurring immunoglobulins have a common core structure in which two identical light chains (about 24 kD) and two identical heavy chains (about 55 or 70 kD) form a tetramer. The amino-terminal portion of each chain is known as the variable (V) region and can be distinguished from the more conserved constant (C) regions of the remainder of each chain. Within the variable region of the light chain is a C-terminal portion known as the J region. Within the variable region of the heavy chain, there is a D region in addition to the J region. Most of the amino acid sequence variation in immunoglobulins is confined to three separate locations in the V regions known as hypervariable regions or complementarity determining regions (CDRs) which are directly involved in antigen binding. Proceeding from the amino-terminus, these regions are designated CDR1, CDR2 and CDR3, respectively. The CDRs are held in place by more conserved framework regions (FRs). Proceeding from the amino-terminus, these regions are designated FR1, FR2, FR3, and FR4, respectively.

As used herein, the term antibody also includes antibody derivatives. Antibody derivatives include, but are not limited to, humanized antibodies. As used herein, the term "humanized antibody" refers to an immunoglobulin that comprises both a region derived from a human antibody or immunoglobulin and a region derived from a non-human antibody or immunoglobulin. The action of humanizing an antibody consists in substituting a portion of a non-human antibody with a corresponding portion of a human antibody. For example, a humanized antibody as used herein could comprise a non-human region variable region (such as a region derived from a murine antibody) capable of specifically recognizing the variant H3.3 protein and a human constant region derived from a human antibody. In another example, the humanized immunoglobulin can comprise a heavy chain and a light chain, wherein the light chain comprises a complementarity determining region derived from an antibody of non-human origin which specifically bind to a variant H3.3 protein and a framework region derived from a light chain of human origin, and the heavy chain comprises a complementarity determining region derived from an antibody of non-human origin which specifically binds the a variant H3.3 protein and a framework region derived from a heavy chain of human origin.

As used herein, the present application also relates to fragments of the antibodies described herein. As used herein, a "fragment" of an antibody (e.g. a monoclonal antibody) is a portion of an antibody that is capable of specifically recognizing the same epitope as the full version of the antibody. In the present patent application, antibody fragments are capable of specifically recognizing the variant H3.3 protein. Antibody fragments include, but are not limited to, the antibody light chain, single chain antibodies, Fv, Fab, Fab' and F(ab')2 fragments. Such fragments can be produced by enzymatic cleavage or by recombinant techniques. For instance, papain or pepsin cleavage can be used to generate Fab or F(ab')2 fragments, respectively. Antibodies can also be produced in a variety of truncated forms using antibody genes in which one or more stop codons have been introduced upstream of the natural stop site. For example, a chimeric gene encoding the heavy chain of an F(ab')2 fragment can be designed to include DNA sequences encoding the CH1 domain and hinge region of the heavy chain. Antibody fragments can also be humanized. For example, a humanized light chain comprising a light chain CDR (i.e. one or more CDRs) of non-human origin and a human light chain framework region. In another example, a humanized immunoglobulin heavy chain can comprise a heavy chain CDR (i.e., one or more CDRs) of non-human origin and a human heavy chain framework region. The CDRs can be derived from a non-human immunoglobulin.

The polyclonal antibody composition obtained by this method can be used for other purposes. The polyclonal antibody composition can be used directly as it is generated by the method, or can be further processed prior to its use. For example, the polyclonal antibody composition can be further fragmented, humanized, inked to another agent, etc.

The antibody composition can be coupled (i.e., physically linked) to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol: examples of bioluminescent materials include luciferase, luciferin, and aequorin, and examples of suitable radioactive materials include $^{125}I$, $^{131}I$, $^{35}S$ or $^{3}H$. Alternatively, the antibody composition can be coupled to a chemotherapeutic agent; a toxin (e.g., an enzymatically active toxin of bacterial, fungal, plant, or animal origin, or fragments thereof); a radioactive isotope (i.e., a radioconjugate). Exemplary toxins include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (e.g. PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes.

Therapeutic Methods

The present application does hereby provide that non-conservative substitutions in H3.3 variants most likely gain a novel biological function. As shown in the Experimental section below, the K27M and the G34R variants of H3.3 remain most likely unmethylated at residues 27 and 36, respectively. This lack of methylation limits the ability of the H3.3 variants to keep the chromatin in a closed configuration and, ultimately leads to the expression of various genes (some of which are listed in Table 7) as well as the elongation of telomeres. As also shown herein, the presence of the non-conservative H3.3 variants are limited to the afflicted cells or tissues (e.g. tumor). Consequently, it is expected that the increased expression of wild-type H3.3 in the tumor or the decrease of the expression of the non-conservative H3.3 variants would shift the balance of chromatin configuration towards a closed one and would limit gene expression associated with the presence of the non-conservative H3.3 variants. It is also expected that the increased expression of wild-type H3.3 in the tumor or the decrease of the expression of the non-conservative H3.3 variants would limit the lengthening of the telomeres and may even shorten the telomeres. In return, this shift in chromatin configuration and telomere lengthening is thought to be useful for the prevention, treatment and/or alleviation of symptoms associated with a proliferation-associated disorder, such as cancer.

The agents that can be administered for this purpose include, but are not limited to, small molecules, peptides, antibodies, nucleic acids, analogs thereof, multimers thereof, fragments thereof, derivatives thereof and combinations thereof.

In an embodiment, nucleic acid molecules encoding the wild-type H3.3 (SEQ ID NO: 5) could be administered to an Individual. Their expression in the individual, preferably in the vicinity of the tumor or directly in the tumor can lead to an increase presence of the wild-type H3.3 polypeptide in the tumor to provide therapeutic benefits. These nucleic acid molecules can be inserted into any of a number of well-known vectors for their introduction in target cells and subjects as described below. The nucleic acids can be introduced into cells, ex vivo or in vivo, through the interaction of the vector and the target cell. The nucleic acid molecules encoding the H3.3 polypeptide, under the control of a promoter, then express the encoded protein, thereby mitigating the effects of the non-conservative H3.3 variants present in the tumor. In an embodiment, the nucleic acid molecule are targeted for expression in a glial cell.

In another embodiment, it is possible to administer directly the wild-type H3.3 protein to the afflicted individual. Preferably, the wild-type H3.3 protein is administered intra-tumorally and is formulated to reach the nucleus of the cells (preferably the glial cells).

In still another embodiment, peptide mimetics can mimic the three-dimensional structure of the wild-type H3.3 polypeptide and can be used in the present methods. Such peptide mimetics may have significant advantages over naturally occurring peptides, including, for example: more economical production, greater chemical stability, enhanced pharmacological properties (half-life, absorption, potency, efficacy, etc.), altered specificity (e.g. a broad-spectrum of biological activities), reduced antigenicity and others. In one form, mimetics are peptide-containing molecules that mimic elements of protein secondary structure. The underlying rationale behind the use of peptide mimetics s that the peptide backbone of proteins exists chiefly to orient amino acid side chains in such a way as to facilitate molecular interactions, such as those of antibody and antigen. A peptide mimetic is expected to permit molecular interactions similar to the natural molecule. In another form, peptide analogs are commonly used in the pharmaceutical industry as non-peptide drugs with properties analogous to those of the template peptide. Peptide mimetics that are structurally similar to therapeutically useful peptides may be used to produce an equivalent therapeutic or prophylactic effect.

Optionally or in combination, it is possible to limit and even shut down the expression of the non-conservative H3.3 variants in the present methods. As an example, an antisense nucleic acid or oligonucleotide is wholly or partially complementary to, and can hybridize with, a target nucleic acids encoding the non-conservative H3.3 variant polypeptide (either DNA or RNA) is administered to the individual. For example, an antisense nucleic acid or oligonucleotide can be complementary to 5' or 3' untranslated regions, or can overlap the translation initiation codon (5' untranslated and translated regions) of at least one nucleic acid molecule encoding for a non-conservative H3.3 variant. As non-limiting examples, antisense oligonucleotides may be targeted to hybridize to the following regions: mRNA cap region, translation initiation site; translational termination site; transcription initiation site; transcription termination site; polyadenylation signal; 3' untranslated region; 5' untranslated region; 5' coding region, mid coding region; 3 coding region: DNA replication initiation and elongation sites. Preferably, the complementary oligonucleotide is designed to hybridize to the most unique 5' sequence of a nucleic acid molecule encoding for a non-conservative H3.3 variant, including any of about 15-35 nucleotides spanning the 5' coding sequence.

In another embodiment, oligonucleotides can be constructed which will bind to duplex nucleic acid (i.e., DNA: DNA or DNA:RNA), to form a stable triple helix containing or triplex nucleic acid. Such triplex oligonucleotides can inhibit transcription and/or expression of a nucleic acid encoding a non-conservative H3.3 variant. Triplex oligonucleotides are constructed using the base-pairing rules of triple helix formation.

In yet a further embodiment, oligonucleotides can be used in the present method. In the context of this application, the term "oligonucleotide" refers to naturally-occurring species or synthetic species formed from naturally-occurring subunits or their close homologs. The term may also refer to moieties that function similarly to oligonucleotides, but have non-naturally-occurring portions. Thus oligonucleotides may have altered sugar moieties or inter-sugar linkages. Exemplary among these are phosphorothioate and other sulfur containing species which are known in the art. In preferred embodiments, at least one of the phosphodiester bonds of the oligonucleotide has been substituted with a structure that functions to enhance the ability of the compositions to penetrate into the region of cells where the RNA whose activity is to be modulated is located. It is preferred that such substitutions comprise phosphorothioate bonds, methyl phosphonate bonds, or short chain alkyl or cycloalkyl structures. In accordance with other preferred embodiments, the phosphodiester bonds are substituted with structures which are, at once, substantially non-ionic and non-chiral, or with structures which are chiral and enantiomerically specific. Persons of ordinary skill in the art will be able to select other linkages for use in the practice of the invention. Oligonucleotides may also include species that include at least some modified base forms. Thus, purines and pyrimidines other than those normally found in nature may be so employed. Similarly, modifications on the furanosyl portions of the nucleotide subunits may also be affected, as long as the essential tenets of this invention are adhered to. Examples of such modifications are 2'-O-alkyl- and 2'-halogen-substituted nucleotides. Some non-limiting examples of modifications at the 2' position of sugar moieties which are useful in the present invention include OH, SH, $SCH_3$, F, $OCH_3$, OCN, $O(CH_2)$, $NH_2$ and $O(CH_2)_n CH_3$, where n is from 1 to about 10. Such oligonucleotides are functionally interchangeable with natural oligonucleotides or synthesized oligonucleotides, which have one or more differences from the natural structure. All such analogs are comprehended herewith so long as they function effectively to hybridize with at least one nucleic acid molecule encoding a non-conservative H3.3 variant to inhibit the function thereof.

Alternatively, expression vectors derived from retroviruses, adenovirus, herpes or vaccinia viruses or from various bacterial plasmids may be used for delivery of nucleotide sequences to the targeted organ, tissue or cell population. Methods which are well known to those skilled in the art can be used to construct recombinant vectors which will express nucleic acid sequence that is complementary to the nucleic acid sequence encoding a non-conservative H3.3 polypeptide.

RNA interference (RNAi) is a post-transcriptional gene silencing process that is induced by a miRNA or a dsRNA (a small interfering RNA; siRNA), and has been used to modulate gene expression. RNAi can be used in the therapeutic method describe herewith. Generally, RNAi is being performed by contacting cells with a double stranded siRNA ou a small hairpin RNA (shRNA). However, manipulation of RNA outside of cells is tedious due to the sensitivity of RNA to degradation. It is thus also encompassed herein a deoxyribonucleic acid (DNA) compositions encoding small interfering RNA (siRNA) molecules, or intermediate siRNA molecules (such as shRNA), comprising one strand of an siRNA be used. Accordingly, the present application provides an isolated DNA molecule, which includes an expressible template nucleotide sequence of at least about 16 nucleotides encoding an Intermediate siRNA, which, when a component of an siRNA, mediates RNA interference (RNAi) of a target RNA. The present application further concerns the use of RNA interference (RNAi) to modulate the expression of nucleic acid molecules encoding the non-conservative H3.3 variants in target cells. While the therapeutic applications are not limited to a particular mode of action, RNAi may involve degradation of messenger RNA (e.g., mRNA of genes of non-conservative H3.3 variants) by an RNA induced silencing complex (RISC), preventing translation of the transcribed targeted mRNA. Alternatively, it may also involve methylation of genomic DNA, which shuts down transcription of a targeted gene. The suppression of gene expression caused by RNAi may be transient or it may be more stable, even permanent.

"Small interfering RNA" or siRNA can also be used in the present methods. It o refers to any nucleic acid molecule capable of mediating RNA interference "RNAi" or gene silencing. For example, siRNA can be double stranded RNA molecules from about 10 to about 30 nucleotides long that are named for their ability to specifically interfere with protein expression (e.g. the non-conservative H3.3 variant protein expression). In one embodiment, siRNAs of the present invention are 12-28 nucleotides long, more preferably 15-25 nucleotides long, even more preferably 19-23 nucleotides long and most preferably 21-23 nucleotides long. Therefore preferred siRNA are 12, 13, 14, 15, 16, 17, 18, 19, 20, 21, 22, 23, 24, 25, 26, 27, 28 nucleotides in length. As used herein, siRNA molecules need not to be limited to those molecules containing only RNA, but further encompass chemically modified nucleotides and non-nucleotides, siRNA can be designed to decrease expression of non-conservative H3.3 variants in a target cell by RNA interference, siRNAs can comprise a sense region and an antisense region wherein the antisense region comprises a sequence complementary to an mRNA sequence for a nucleic aced molecule encoding non-conservative H3.3 variants and the sense region comprises a sequence complementary to the antisense sequence of the gene's mRNA. An siRNA molecule can be assembled from two nucleic acid fragments wherein one fragment comprises the sense region and the second fragment comprises the antisense region of siRNA molecule. The sense region and antisense region can also be covalently connected via a linker molecule. The linker molecule can be a polynucleotide linker or a non-polynucleotide linker.

A ribozyme (from ribonucleic acid enzyme, also called RNA enzyme or catalytic RNA) is an RNA molecule that catalyzes a chemical reaction. Some ribozymes may play an important role as therapeutic agents, as enzymes which target defined RNA sequences, as biosensors, and for applications in functional genomics and gene discovery. Ribozymes can be genetically engineered to specifically cleave a transcript of a gene from a nucleic acid molecule encoding non-conservative H3.3 variant whose expression is upregulated with the disease.

The delivery of the gene or genetic material into the cell (encoding partly or wholly the wild-type H3.3 or a sequence that will lower the expression of a non-conservative H3.3 variant) is the first step in gene therapy treatment of any disorder. A large number of delivery methods are well known to those of skill in the art. Preferably, the nucleic acids are administered for in vivo or ex vivo gene therapy uses. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell.

The use of RNA or DNA based viral systems for the delivery of nucleic acids take advantage of highly evolved processes for targeting a virus to specific cells in the body and trafficking the viral payload to the nucleus. Viral vectors can be administered directly to patients (in vivo) or they can be used to treat cells in vitro and the modified cells then administered to patients (ex vivo). Conventional viral based systems for the delivery of nucleic acids could include retroviral, lentiviral, adenoviral, adeno-associated and herpes simplex virus vectors for gene transfer. Viral vectors are currently the most efficient and versatile method of gene transfer in target cells and tissues. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

In applications where transient expression of the nucleic acid is preferred, adenoviral based systems are typically used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures.

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system.

Replication-deficient recombinant adenoviral vectors (Ad) are predominantly used in transient expression gene therapy; because they can be produced at high titer and they readily infect a number of different cell types. Most adenovirus vectors are engineered such that a transgene replaces the Ad E1a, E1b, and E3 genes; subsequently the replication defective vector is propagated in human 293 cells that supply the deleted gene function in trans. Ad vectors can transduce multiple types of tissues in vivo, including non-dividing, differentiated cells such as those found in the liver, kidney and muscle tissues. Conventional Ad vectors have a large carrying capacity.

In many gene therapy applications, it is desirable that the gene therapy vector be delivered with a high degree of specificity to a particular tissue type, such as for example, the glial cells. A viral vector is typically modified to have specificity for a given cell type by expressing a ligand as a fusion protein with a viral coat protein on the viruses outer surface. The ligand is chosen to have affinity for a receptor known to be present on the cell type of interest.

Gene therapy vectors can be delivered in vivo by administration to an individual subject, typically by systemic administration (e.g., intravenous, intratumoral, intrapentoneal, intramuscular, subdermal, or intracranial infusion) or topical application. Alternatively, vectors can be delivered to cells ex vivo, such as cells explanted from an Individual patient (e.g., lymphocytes, bone marrow aspirates, and tissue biopsy) or universal donor hematopoietic stem cells, followed by re-implantation of the cells into the subject, usually after selection for cells which have incorporated the vector.

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft at an appropriate location (such as in the bone marrow). Methods for differentiating CD34+ cells in vitro into clinically important immune cell types using cytokines such as for example GM-CSF, IFN-γ and TNF-α are known.

Stem cells are isolated for transduction and differentiation using known methods. For example, stem cells can be isolated from bone marrow cells by panning the bone marrow cells with antibodies which bind unwanted cells, such as CD4+ and CD8+ (T cells), CD45+ (panB cells), GR-1 (granulocytes), and Iad (differentiated antigen presenting cells).

Administration is by any of the routes normally used for introducing a molecule into ultimate contact with blood or tissue cells. The nucleic acids molecules described herein can be administered in any suitable manner, preferably with the pharmaceutically acceptable carriers or excipients. The terms "pharmaceutically acceptable carrier", "excipients" and "adjuvant" and "physiologically acceptable vehicle" and the like are to be understood as referring to an acceptable carrier or adjuvant that may be administered to a patient, together with a compound of this invention, and which does not destroy the pharmacological activity thereof. Further, as used herein "pharmaceutically acceptable carrier" or "pharmaceutical carrier" are known in the art and include, but are not limited to, 0.01-0.1 M and preferably 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

As used herein, "pharmaceutical composition" means therapeutically effective amounts (dose) of the agent together with pharmaceutically acceptable diluents, preservatives, solubilizers, emulsifiers, adjuvants and/or carriers. A "therapeutically effective amount" as used herein refers to that amount which provides a therapeutic effect for a given condition and administration regimen. Such compositions are liquids or lyophilized or otherwise dried formulations and include diluents of various buffer content (e.g., Tris-HCl, acetate, phosphate), pH and ionic strength, additives such as albumin or gelatin to prevent absorption to surfaces, and detergents (e.g., TWEEN 20™, TWEEN 80™, PLURONIC F68™, bile acid salts). The pharmaceutical composition can comprise pharmaceutically acceptable solubilizing agents (e.g., glycerol, polyethylene glycerol), anti-oxidants (e.g., ascorbic acid, sodium metabisulfite), preservatives (e.g., thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc, or onto liposomes, microemulsions, micelles, unilamellar or multilamellar vesicles, erythrocyte ghosts, or spheroplast. Such compositions will influence the physical state, solubility, stability, rate of in vivo release, and rate of in vivo clearance. Controlled or sustained release compositions include formulation in lipophilic depots (e.g., fatty acids, waxes, oils). Also comprehended by the invention are particulate compositions coated with polymers (e.g., poloxamers or poloxamines).

Suitable methods of administering such nucleic acids are available and well known to those of skill in the art, and, although more than one route can be used to administer a particular composition, a particular route can often provide a more immediate and more effective reaction than another route. The preventive or therapeutic agents of the present invention may be administered, either orally or parenterally, systemically or locally. For example, intravenous injection such as drip infusion, intramuscular injection, intraperitoneal injection, subcutaneous injection, suppositories, intestinal lavage, oral enteric coated tablets, and the like can be selected, and the method of administration may be chosen, as appropriate, depending on the age and the conditions of the patient. The effective dosage is chosen from the range of 0.01 mg to 100 mg per kg of body weight per administration. Alternatively, the dosage in the range of 1 to 1000 mg, preferably 5 to 50 mg per patient may be chosen. The preventive or therapeutic agents are preferably administered locally to the tumor (e.g. intrathecally, intratumorally).

Screening Methods

As shown herein, in a tumor, there is an imbalance between the levels of wild-type H3.3 and the non-conservative H3.3 variants. More specifically, the tumor expresses higher levels of the non-conservative H3.3 variants that the wild-type H3.3 proteins. This has been shown to cause an increase in telomeric length. This is also thought to cause an increase in gene expression. As such, the present application provides screening applications to determine the usefulness of an agent in the treatment, prevention and/or alleviation of symptoms of a proliferation-associated disorder. The agent can be considered useful if they increase the expression of the wild-type H3.3 protein, particularly at the level of the cells of the tumor. The agent can also be considered useful if they decrease the expression of the non-conservative H3.3 variants, particularly at the level of the cells of the tumor. The agent can further be considered useful if they increase the expression of the wild-type H3.3 protein and decrease the expression of the non-conservative H3.3 variants, particularly at the level of the cells of the tumor.

In screening applications, an agent to be screened is placed in a reaction vessel and is supplemented with an H3.3-based reagent. In the assays, the reaction vessel can be any type of container that can accommodate the measurement of an H3.3-based reagent's parameter. As used herein, the H3.3-based reagent is either a polynucleotide encoding the H3.3 protein, a H3.3 polypeptide and/or a the promoter or regulator region of the H3.3 gene.

For screening applications, a suitable in vitro environment for the screening assay described herewith can be a cultured cell. Such cell should be able to maintain viability in culture. Consequently, the cultured cell(s) should (i) express a polynucleotide encoding H3.3 (ii) express a H3.3-encoding polynucleotide and/or (ii) comprise the H3.3 promoter region. The cell is preferably derived from a brain tissue (primary cell culture or cell line) and even more preferably is a glial cell. If a primary cell culture is used, the cell may be isolated or in a tissue-like structure. A further suitable environment is a non-human model, such as an animal model. If the characterization of the agent occurs in a non-human model, then the model (such as a rodent or a worm) is administered with the agent. Various dosage and modes of administration may be used to fully characterize the agent's ability to prevent, treat and/or alleviate the symptoms of a proliferation-associated disorder.

Once the biological sample or the agent has been placed in the reaction vessel with the H3.3-based reagent, a measurement or value of a parameter of the H3.3-based reagent is made. This assessment may be made directly in the reaction vessel (by using a probe) or on a sample of such reaction vessel. The measurement of the parameter of the H3.3-based reagent can be made either at the DNA level, the RNA level and/or the polypeptide level.

The measuring step can rely on the addition of a quantifier specific to the parameter to be assessed to the reaction vessel or a sample thereof. The quantifier can specifically bind to a parameter of a H3.3-based reagent that is being assessed, such as, for example, a nucleotide product encoding H3.3 or a H3.3 polypeptide. In those instances, the amount of the quantifier that specifically bound (or that did not bind) to the H3.3-based reagent can be determined to provide a measurement of the parameter of the H3.3-based reagent. In another embodiment, the quantifier can be modified by a parameter of the H3.3-based reagent, such as, for example, H3.3's biological activity. In this specific instance, the amount of modified (or unmodified) quantifier will be determine to provide a measurement of the parameter of the H3.3-based reagent. In an embodiment, the signal of the quantifier can be provided by a label that is either directly or indirectly linked to the quantifier.

Various parameters of the H3.3-based reagent can be measured. For example, when the H3.3-based reagent is a H3.3 polypeptide or fragment thereof, the parameter that is measured can be the polypeptide's biological activity, the polypeptide quantity and/or stability. When the H3.3-based reagent is a nucleotide encoding a H3.3 polypeptide or fragment thereof, the parameter can be the level of expression and/or stability of the H3.3-encoding nucleotide. Even though a single parameter is required to enable the characterization of the agent, it is also provided that more than one parameter of the H3.3-based reagent may be measured and even that more than one H3.3-based reagents may be used in the characterization.

If the measurement of the parameter is performed at the nucleotide level, then the transcription activity of the promoter or regulator associated with the H3.3 gene can be assessed. This assessment can be made, for example, by using a reporter vector (such as a luciferase reporter based assay). Such reporter vectors can include, but are not limited to, the promoter region of the H3.3 gene (or fragments thereof) operably linked to a nucleotide encoding a reporter polypeptide (such as, for example, H3.3, β-galactosidase, green-fluorescent protein, yellow-fluorescent protein, etc.). Upon the addition of the agent in the reaction vessel, the promotion of transcription from the promoter of the H3.3 gene is measured indirectly by measuring the transcription of the reporter polypeptide. In this particular embodiment, the quantifier is the reporter polypeptide and the signal associated to this quantifier that is being measured will vary upon the reporter polypeptide used. Alternatively or complementarily, the stability and/or the expression level of the H3.3-encoding nucleotide can be assessed by quantifying the amount of a H3.3-encoding nucleotide (for example using qPCR or real-time PCR) or the stability of such nucleotide.

In another assay format, the expression of a nucleic acid encoding H3.3 in a cell or tissue sample is monitored directly by hybridization to the nucleic acids specific for H3.3. In another assay format, cell lines or tissues can be exposed to the agent to be tested under appropriate conditions and time, and total RNA or mRNA isolated, optionally amplified, and quantified.

In another assay format, H3.3's biological activity can be indirectly measured by quantifying the expression levels of its target genes whose expression is modulated by the presence and activity of H3.3. Some of the target genes associated with H3.3's biological activity are presented in Table 7. In another embodiment, H3.3's activity is measured indirectly by measuring the expression of at least one gene presented in Table 7. In another embodiment, H3.3's activity is measured indirectly by measuring the expression of at least five genes presented in Table 7. In a further embodiment, H3.3's activity is measured indirectly by measuring the expression of at least ten genes presented in Table 7.

If the measurement of the parameter is performed at the polypeptide level, an assessment of the H3.3 level of expression can be performed. In an embodiment, specifically the level of expression of the H3.3 polypeptide is measured for example, through an antibody-based technique (such as a Western blot, an ELISA or a FACS), a micro-array, spectrometry, etc. In one embodiment, this assay is performed utilizing antibodies specific to H3.3 or target molecules but which do not interfere with binding of the H3.3 to its target molecule (such as, for example, ATRX or DAXX). Such antibodies can be directed to the surface, and unbound target or the H3.3-based reagent trapped on the surface by antibody conjugation. Methods for detecting such complexes, in addition to those described above for the GST-immobilized complexes, include immunodetection of complexes using antibodies reactive with the H3.3-based reagent or target molecule, as well as enzyme-linked assays which rely on detecting an enzymatic activity associated with the H3.3-based reagent or target molecule.

In addition, an assessment of H3.3's biological activity can be performed. H3.3 is a chromatin regulator that modulates gene expression in general. One of H3.3's biological activity is to bind to other partners as well as to associate with DNA.

The evaluation of H3.3's biological activity can be made in vitro. The reaction mixture can include, e.g. a cofactor, a substrate (such as DNA) or other binding partner or potentially interacting fragment thereof. Exemplary binding partners include ATRX, DAXX, or interacting fragments thereof. Preferably, the binding partner is a direct binding partner. This type of assay can be accomplished, for example, by coupling one of the components, with a label such that binding of the labeled component to the other can be determined by detecting the labeled compound in a complex. A component can be labeled with $^{125}I$, $^{35}S$, $^{14}C$, or $^{3}H$, either directly or indirectly, and the radioisotope detected by direct counting of radioemmision or by scintillation counting. Alternatively, a component can be enzymatically labeled with, for example, horseradish peroxidase, alkaline phosphatase, or luciferase, and the enzymatic label detected by determination of conversion of an appropriate substrate to product. Competition assays can also be used to evaluate a physical interaction between a test compound and a target.

Cell-free screening assays usually involve preparing a reaction mixture of the target protein and the test compound under conditions and for a time sufficient to allow the two components to interact and bind, thus forming a complex that can be removed and/or detected.

The interaction between two molecules can also be detected, e.g., using a fluorescence assay in which at least one molecule is fluorescently labeled. One example of such an assay includes fluorescence energy transfer (FET or FRET for fluorescence resonance energy transfer). A fluorophore label on the first "donor" molecule is selected such that its emitted fluorescent energy will be absorbed by a fluorescent label on a second "acceptor" molecule, which in turn is able to fluoresce due to the absorbed energy. Alternately, the "donor" protein molecule may simply utilize the natural fluorescent energy of tryptophan residues. Labels are chosen that emit different wavelengths of light, such that the "acceptor" molecule label may be differentiated from that of the "donor". Since the efficiency of energy transfer between the labels is related to the distance separating the molecules, the spatial relationship between the molecules can be assessed. In a situation in which binding occurs between the molecules, the fluorescent emission of the "acceptor" molecule label in the assay should be maximal. A FET binding event can be conveniently measured through standard fluorometric detection means well known in the art (e. g., using a fluorimeter).

Another example of a fluorescence assay is fluorescence polarization (FP). For FP, only one component needs to be labeled. A binding interaction is detected by a change in molecular size of the labeled component. The size change alters the tumbling rate of the component in solution and is detected as a change in FP.

In another embodiment, the measuring step can rely on the use of real-time Biomolecular Interaction Analysis (BIA). "Surface plasmon resonance" or "BIA" detects biospecific interactions in real time, without labeling any of the interactants (e.g. BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, the H3.3-based reagent is anchored onto a solid phase. The H3.3-based reagent-related complexes anchored on the solid phase can be detected at the end of the reaction, e. g., the binding reaction. For example, the H3.3-based reagent can be anchored onto a solid surface, and the test compound, (which is not anchored), can be labeled, either directly or indirectly, with detectable labels discussed herein. Examples of such solid phase include microtiter plates, test tubes, array slides, beads and microcentrifuge tubes. In one embodiment, a H3.3 chimeric protein can be provided which adds a domain that allows one or both of the proteins to be bound to a matrix. Following incubation, the vessels are washed to remove any unbound components, the matrix immobilized in the case of beads, complex determined either directly or indirectly, for example, as described above. Alternatively, the complexes can be dissociated from the matrix, and the level of H3.3 binding or activity determined using standard techniques.

In order to conduct the assay, the non-immobilized component (agent or biological agent) is added to the coated surface containing the anchored component. After the reaction is complete, unreacted components are removed (e.g. by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface, e.g., using a labeled antibody specific for the immobilized component (the antibody, in turn, can be directly labeled or indirectly labeled with, e.g. a labeled anti-Ig antibody).

Alternatively, cell free assays can be conducted in a liquid phase. In such an assay, the reaction products are separated from unreacted components, by any of a number of standard techniques, including but not limited to: differential centrifugation; chromatography (gel filtration chromatography, ion-exchange chromatography) and/or electrophoresis. Such resins and chromatographic techniques are known to one skilled in the art. Further, fluorescence energy transfer may also be conveniently utilized, as described herein, to detect binding without further purification of the complex from solution.

To identify agents that modulate the interaction between H3.3 and its binding partner(s), for example, a reaction mixture containing the H3.3-based reagent and the binding partner is prepared, under conditions and for a time sufficient, to allow the two products to form complex. In order to test if an agent which facilitates the interaction between H3.3 and its binding partner, the reaction mixture can be provided in the presence and absence of the test agent. The test agent can be initially included in the reaction mixture, or can be added at a time subsequent to the addition of the target and its cellular or extracellular binding partner. Control reaction mixtures are incubated without the test agent or with vehicle. The formation of any complexes between the target product and the cellular or extracellular binding partner is then detected. The formation of a complex in the reaction mixture containing the test compound, but not in the control reaction, indicates that the test agent facilitates the interaction of the H3.3-based reagent and the interactive binding partner. In an embodiment, it is possible to detect the formation of the H3.3-based complex indirectly by measuring the level of expression of a reporter gene whose expression is modulated by the presence (or absence) of the complex.

These assays can be conducted in a heterogeneous or homogeneous format Heterogeneous assays involve anchoring either the H3.3-based reagent or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the agents being tested. For example, test agents that interfere with the interaction between the H3.3-based reagent and the binding partners, e.g., by competition, can be identified by conducting the reaction in the presence of the test substance. Alternatively, test agents that facilitates preformed complexes, can be tested by adding the test compound to the reaction mixture prior to complexes have been formed. The various formats are briefly described below.

In a heterogeneous assay system, either the H3.3-based reagent or the binding partner, is anchored onto a solid surface (e.g. a microtiter plate), while the non-anchored species is labeled, either directly or indirectly. The anchored species can be immobilized by non-covalent or covalent attachments. Alternatively, an Immobilized antibody specific for the species to be anchored can be used to anchor the species to the solid surface.

In order to conduct the assay, the partner of the immobilized species is exposed to the coated surface with or without the agent. After the reaction is complete, unreacted components are removed (e.g. by washing) and any complexes formed will remain immobilized on the solid surface. Where the non-immobilized species is pro-labeled, the detection of label immobilized on the surface indicates that complexes were formed. Where the non-immobilized species is not pre-labeled, an Indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, agents that enable complex formation or that promote the stability of preformed complexes can be detected.

Alternatively, the reaction can be conducted in a liquid phase in the presence or absence of the agent, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that enable complex or that promote the stability of preformed complexes can be identified.

In an alternate embodiment, a homogeneous assay can be used. For example, a preformed complex of the H3.3-based reagent and the interactive cellular or extracellular binding partner product is prepared in that either the target products or their binding partners are labeled, but the signal generated by the label is quenched due to complex formation. The addition of agent that favors the formation of the complex will result in the generation of a signal below the control value. In this way, agents that modulate H3.3-binding partner interaction can be identified.

In yet another aspect, the H3.3-based reagent can be used as "bait proteins" in a two-hybrid assay or three-hybrid assay, to identify other proteins, which bind to or interact with H3.3 binding proteins and are involved in H3.3's biological activity. Such binding partners can be activators or inhibitors of signals or transcriptional control.

In another embodiment, the assay for selecting compounds which interact with H3.3 can be a cell-based assay. Useful assays include assays in which a marker of chromatin configuration or telomere length is measured. The cell-based assay can include contacting a cell expressing a H3.3-based reagent with an agent and determining the ability of the test compound to modulate (e.g. stimulate or inhibit) the activity of a H3.3, and/or determine the ability of the agent to modulate expression of a H3.3, e.g. by detecting H3.3-encoding nucleic acids (e.g., mRNA) or related proteins in the cell. Determining the ability of the agent to modulate H3.3 activity can be accomplished, for example, by determining the ability of the H3.3 to bind to or interact with the agent, and by determining the ability of the agent to modulate heart remodeling/heart disease. Cell-based systems can be used to identify compounds that increase the expression and/or activity and/or effect of H3.3. Such cells can be recombinant or non-recombinant, such as cell lines that express the H3.3 gene. In some embodiments, the cells can be recombinant or non-recombinant cells which express a H3.3-binding partner. Exemplary systems include mammalian or yeast cells that express a H3.3 (for example from a recombinant nucleic acid). In utilizing such systems, cells are exposed to agents suspected of increasing expression and/or activity of a H3.3. After exposure, the cells are assayed, for example, for H3.3 expression or activity. A cell can be from a stable cell line or a primary culture obtained from an organism (for example an organism treated with the agent).

In addition to cell-based and in vitro assay systems, non-human organisms, e.g. transgenic non-human organisms or a model organism, can also be used. A transgenic organism is one in which a heterologous DNA sequence is chromosomally integrated into the germ cells of the animal. A transgenic organism will also have the transgene integrated into the chromosomes of its somatic cells. Organisms of any species, including, but not limited to: yeast, worms, flies, fish, reptiles, birds, mammals (e.g. mice, rats, rabbits, guinea pigs, pigs, micro-pigs, and goats), and non-human primates (e.g. baboons, monkeys, chimpanzees) may be used in the methods described herein.

A transgenic cell or animal used in the methods described herein can include a transgene that encodes, e.g. an H3.3 polypeptide, fragment or variant. The transgene can encode a protein that is normally exogenous to the transgenic cell or animal, including a human protein, e.g. a human H3.3 or one of its biding partner. The transgene can be linked to a heterologous or a native promoter. Methods of making transgenic cells and animals are known in the art.

In another assay format, the specific activity of H3.3, normalized to a standard unit, may be assayed in a cell-free system, a cell line, a cell population or animal model that has been exposed to the agent to be tested and compared to an unexposed control cell-free system, cell line, cell population or animal model. The specific activity of an H3.3-activating reagent can also be assessed using H3.3-deficient systems (H3.3 knockout cells or animals) as a control.

Once the measurement has been made, it is extracted from the reaction vessel, and the value of the parameter of the H3.3-based reagent is compared to a control value. In an embodiment the control value is associated with a lack of proliferation-associated disorder.

In an embodiment, when the control value is associated with a lack of a proliferation-associated disorder, the H3.3-based reagent can be derived from a wild-type H3.3. In such assay format, agents useful in the prevention, treatment and/or alleviation of symptoms of a proliferation associated disorder are able to increase the expression and/or stability of nucleic acid molecule encoding the wild-type H3.3 or the expression and/or the activity of the wild-type H3.3 protein. In an embodiment, the agent identified as useful does not increase the expression and/or stability of nucleic acid molecule encoding the non-conservative H3.3 variants nor the expression and/or the activity of the non-conservatives H3.3 variants. In another embodiment, the identified agent is capable of limiting and even reducing the expression and/or stability of nucleic acid molecule encoding the non-conservative H3.3 variants nor the expression and/or the activity of the non-conservatives H3.3 variants. In such assay format, the agent is considered not to be useful if the test value is equal to or lower than the control value.

In an embodiment, when the control value is associated with a lack of a proliferation-associated disorder, the H3.3-based reagent can be derived from a non-conservative H3.3 variant. In such assay format, agents useful in the prevention, treatment and/or alleviation of symptoms of a proliferation associated disorder are able to decrease the expression and/or stability of nucleic acid molecule encoding the non-conservative H3.3 variants or the expression and/or the activity of the non-conservative H3.3 variants. In an embodiment, the agent identified as useful does not decrease the expression and/or stability of nucleic acid molecule encoding the wild-type H3.3 proteins nor the expression and/or the activity of the wild-type H3.3 proteins. In another embodiment, the identified agent is capable of increasing the expression and/or stability of nucleic acid molecule encoding the wild-type H3.3 proteins nor the expression and/or the activity of the wild-type H3.3 proteins. In such assay format the agent is considered not to be useful if the test value is equal to or higher than the control value.

In another embodiment, the control value is associated with a proliferation-associated disorder.

In an embodiment, when the control value is associated with a proliferation-associated disorder, the H3.3-based reagent can be derived from a wild-type H3.3. In such assay format, agents useful in the prevention, treatment and/or alleviation of symptoms of a proliferation associated disorder are able to increase the expression and/or stability of nucleic acid molecule encoding the wild-type H3.3 or the expression and/or the activity of the wild-type H3.3 protein. In an embodiment, the agent identified as useful does not increase the expression and/or stability of nucleic acid molecule encoding the non-conservative H3.3 variants nor the expression and/or the activity of the non-conservatives H3.3 variants. In another embodiment, the identified agent is capable of limiting and even reducing the expression and/or stability of nucleic acid molecule encoding the non-conservative H3.3 variants nor the expression and/or the activity of the non-conservatives H3.3 variants. In such assay format the agent is considered not to be useful if the test value is equal to or lower than the control value.

In an embodiment, when the control value is associated with a proliferation-associated disorder, the H3.3-based reagent can be derived from a non-conservative H3.3 variant. In such assay format, agents useful in the prevention, treatment and/or alleviation of symptoms of a proliferation associated disorder are able to decrease the expression and/or stability of nucleic acid molecule encoding the non-conservative H3.3 variants or the expression and/or the activity of the non-conservative H3.3 variants. In an embodiment, the agent identified as useful does not decrease the expression and/or stability of nucleic acid molecule encoding the wild-type H3.3 proteins nor the expression and/or the activity of the wild-type H3.3 proteins. In another embodiment, the identified agent is capable of increasing the expression and/or stability of nucleic acid molecule encoding the wild-type H3.3 proteins nor the expression and/or the activity of the wild-type H3.3 proteins. In such assay format, the agent is considered not to be useful if the test value is equal to or higher than the control value.

In an embodiment, the comparison can be made by an individual. In another embodiment, the comparison can be made in a comparison module. Such comparison module may comprise a processor and a memory card to perform an application. The processor may access the memory to retrieve data. The processor may be any device that can perform operations on data. Examples are a central processing unit (CPU), a front-end processor, a microprocessor, a graphics processing unit (PPU/VPU), a physics processing unit (PPU), a digital signal processor and a network processor. The application is coupled to the processor and configured to determine the effect of the agent on the parameter of the H3.3-based reagent with respect to the control value. An output of this comparison may be transmitted to a display device. The memory, accessible by the processor, receives and stores data, such as measured parameters of the H3.3-based reagent or any other information generated or used. The memory may be a main memory (such as a high speed Random Access Memory or RAM) or an auxiliary storage unit (such as a hard disk, a floppy disk or a magnetic tape drive). The memory may be any other type of memory (such as a Read-Only Memory or ROM) or optical storage media (such as a videodisc or a compact disc).

Once the comparison between the parameter of the H3.3-based reagent and the control value is made, then it is possible to characterize the agent. This characterization is possible because, as shown herein, (i) wild-type H3.3 is less (or not) present in tumors and (ii) non-conservative H3.3 variants are only expressed in tumors.

In an embodiment, the characterization can be made by an individual. In another embodiment, the characterization can be made with a processor and a memory card to perform an application. The processor may access the memory to retrieve data. The processor may be any device that can perform operations on data. Examples are a central processing unit (CPU), a front-end processor, a microprocessor, a graphics processing unit (PPU/VPU), a physics processing unit (PPU), a digital signal processor and a network processor. The application is coupled to the processor and configured to characterize the agent being screened. An output of this characterization may be transmitted to a display device. The memory, accessible by the processor, receives and stores data, such as measured parameters of the H3.3-based reagent or any other information generated or used. The memory may be a main memory (such as a high speed Random Access Memory or RAM) or an auxiliary storage unit (such as a hard disk, a floppy disk or a magnetic tape drive). The memory may be any other type of memory (such as a Read-Only Memory or ROM) or optical storage media (such as a videodisc or a compact disc).

The screening methods described herein can be used to determine an agent's ability to prevent, treat or alleviate the symptoms of a proliferation-associated disorder. The premise behind this screening method is that non-conservative H3.3 variants's activity or expression is upregulated during disease. As such, by assessing if an downregulation of H3.3's activity or expression made by the agent, it can be linked to its ability to prevent, treat or alleviate the symptoms of a proliferation-associated disorder. In these methods, the control value may be the parameter of the H3.3-based reagent in the absence of the agent. In this particular embodiment, the parameter of the H3.3-reagent can be measured prior to the combination of the agent with the H3.3-based reagent or in two replicates of the same reaction vessel where one of the screening system does not comprise the agent. The control value can also be the parameter of the H3.3-based reagent in the presence of a control agent that is known not to prevent/treat/alleviate the symptoms of a proliferation-associated disease. Such control agent may be, for example, a pharmaceutically inert excipient. The control value can also be the parameter of the H3.3-based reagent obtained from a reaction vessel comprising cells or tissues from a healthy subject that is not afflicted by a proliferation-associated disorder. The ability of the agent is determined based on the comparison of the value of the parameter of the H3.3-based reagent with respect to the control value.

The present application also provides screening systems for performing the characterizations and methods described herein. These systems comprise a reaction vessel for placing the agent (screening system) and the H3.3-based reagent, a processor in a computer system, a memory accessible by the processor and an application coupled to the processor. The application or group of applications is(are) configured for receiving a test value of a level of an H3.3-based reagent in the presence of the agent; comparing the test value to a control value and/or characterizing the agent in function of this comparison.

The present application also provides a software product embodied on a computer readable medium. This software product comprises instructions for characterizing the agent according to the methods described herein. The software product comprises a receiving module for receiving a test value of a level of an H3.3-based reagent in the presence of an agent a comparison module receiving input from the measuring module for determining if the test value is lower than, equal to or higher than a control value; a characterization module receiving input from the comparison module for performing the characterization based on the comparison.

In an embodiment, an application found in the computer system of the system is used in the comparison module. A measuring module extracts/receives information from the reaction vessel with respect to the level of the H3.3-based reagent. The receiving module is coupled to a comparison module which receives the value(s) of the level of the H3.3-based reagent and determines if this value is lower than, equal to or higher than a control value. The comparison module can be coupled to a characterization module.

In another embodiment, an application found in the computer system of the system is used in the characterization module. The comparison module is coupled to the characterization module which receives the comparison and performs the characterization based on this comparison.

In a further embodiment, the receiving module, comparison module and characterization module are organized into a single discrete system. In another embodiment, each module is organized into different discrete system. In still a further embodiment, at least two modules are organized into a single discrete system.

In the screening assay provided herewith, a full length nucleotide sequence encoding the H3.3 polypeptide or a fragment thereof can be used. A "fragment" of a H3.3-encoding nucleotide sequence that encodes a biologically active portion (e.g. for the wild-type H3.3—that retains H3.3's closed chromatin configuration and for the non-conservative variants—that do no retain the H3.3 closed chromatin configuration) of the H3.3 protein and wilt encode at least 5, 10, 12, 25, 30, 50, 75, 100, 125 or 135 contiguous amino adds, or up to the total number of amino acids present in a full-length H3.3 polypeptide. Fragments of the H3.3-encoding nucleotide sequence that are useful as specific hybridization probes and/or as specific PCR primers generally need not encode a biologically active portion of the H3.3 polypeptide.

In the methods provided herewith, it is also possible to use the promoter of the H3.3 gene operably linked to a reporter gene. The reporter gene can encoded a protein that can be detected in the reaction vessel. The reporter gene can be, for example, the H3.3 gene itself or any other gene encoding a protein that can be detected in the reaction vessel (for example the yellow fluorescent protein or the β-galactosidase protein).

The H3.3 polypeptide or a biologically active fragment of the H3.3 polypeptide that retains its characteristic chromatin configuration activity can also be used in the screening assay. "Fragments" or "biologically active portions" of the H3.3 polypeptide include polypeptide fragments comprising amino acid sequences sufficiently identical to or derived from the amino acid sequence of the H3.3 polypeptide and exhibiting at least one activity of the H3.3 polypeptide, but which include fewer amino acids than the full-length H3.3 polypeptide. Typically, biologically active portions comprise a domain or motif with at least one activity of the H3.3 polypeptide. A biologically active portion of the H3.3 polypeptide can be a polypeptide that is, for example, 5, 10, 15, 25, 30, 40, 50, 100, 125 or 135 or more amino acids in length. Such biologically active portions can be prepared by recombinant techniques and evaluated for one or more of the functional activities of a native H3.3 polypeptide.

The methods described herein can also rely on a H3.3 polypeptide chimeric or fusion proteins as an H3.3-based reagent. As used herein, the "chimeric protein" or "fusion protein" comprises the H3.3 polypeptide operably linked to a non-H3.3 polypeptide. A "non-H3.3 polypeptide" is intended to refer to a polypeptide having an amino acid sequence corresponding to a protein that is not substantially identical to the H3.3 polypeptide, e.g., a protein that is different from the H3.3 polypeptide. The non-H3.3 polypeptide can derived from the same or a different organism/species with respect to the H3.3 polypeptide. Within the H3.3 polypeptide fusion protein, the H3.3 polypeptide can correspond to entirety or a portion of the H3.3 polypeptide. The non-H3.3 polypeptide can be fused to the N-terminus or C-terminus of the H3.3 polypeptide. In an embodiment the non-H3.3 polypeptide provides a flag which can facilitates the measurement of the level of expression and/or activity of the H3.3 polypeptide.

The present invention will be more readily understood by referring to the following examples which are given to illustrate the invention rather than to limit its scope.

Example I

Material and Methods

Samples Characteristics and Pathological Review. All samples were obtained with informed consent after approval of the Institutional Review Board of the respective hospitals they were treated in and were independently reviewed by senior pediatric neuropathologists (SA, AK) according to the WHO guidelines. Forty-nine pediatric grade IV astrocytomas (glioblastoma GBM) patients between the age of 1 and 20 years were included in the study. Clinical characteristics of patients are summarized in Table 1. Samples were taken at the time of the first surgery, prior to further treatment as needed. Tissues were obtained from the London/Ontario Tumor Bank the Pediatric Cooperative Health Tissue Network, the Montreal Children's Hospital and from collaborators in Hungary and Germany. Seven hundred and eighty-five glioma samples from all grades and histological diagnoses across the entire age range in this study were obtained from collaborators across Europe and North America.

Alignment and variant valling for whole exome sequencing. We followed standard manufacturer protocols to perform target capture with the Illumina TRUSEQ™ exome enrichment kit and sequencing of 100 bp paired end reads on Illumina HISEQ™. We generated approximately 10 Gb of sequence for each subject such that >90% of the coding bases of the exome defined by the consensus coding sequence (CCDS) project were covered by at least 10 reads. We removed adaptor sequences and quality trimmed reads using the FASTX™ toolkit and then used a custom script to ensure that only read pairs with both mates present were subsequently used. Reads were aligned to hg19 with BWA1, and duplicate reads were marked using Picard and excluded from downstream analyses. Single nucleotide variants (SNVs) and short insertions and deletions (indels) were called using samtools pileup and varFilter2 with the base alignment quality (BAQ) adjustment disabled, and were then quality filtered to require at least 20% of reads supporting the variant call. Variants were annotated using both Annovar3 and custom scripts to identify whether they affected protein coding sequence, and whether they had previously been seen in dbSNP131, the 1000 genomes pilot release (November 2010), or in approximately 160 exomes previously sequenced at our center.

Somatic mutation identification for whole exome sequencing. A variant called in a tumor was considered to be a candidate somatic mutation if the matched normal sample had at least 10 reads covering this position and had zero variant reads, and the variant was not reported in dbSNP131 or the 1000 genomes pilot release (November 2010). For the resulting 117 candidate somatic mutations, we manually examined the alignment of each to check for sequencing artifacts and alignment errors. Fifteen variants were easily identified as sequence-specific error artifacts commonly seen shortly downstream of GGC sequences on Illumina sequencers. Once genes of interest were identified (H3F3A, ATRX, DAXX, TP53, NF1), we examined positions in these genes in the 34 tumor samples where less than 20% of the reads supported the variant. This identified only two additional variants, both in sample GBM-245-SP, where there were low read counts for frameshift insertions in both ATRX (6/32 reads) and DAXX (8/47 reads).

Immunohistochemistry and immunoblotting. Formalin-fixed, paraffin-embedded sections of pediatric GBM and TMA (4 μm) were immunohistochemically stained for ATRX and DAXX proteins. Unstained sections were subjected to antigen retrieval in 10 mM citrate buffer (pH6.0) for 10 minutes at sub-boiling temperatures. Individual slides were incubated overnight at 4° C. with rabbit anti-ATRX (1:750 dilution, Sigma. Cat. #: HPA001906) or rabbit anti-DAXX (1:100 dilution, Sigma, Cat. #: HPA008736) antibodies. Following incubation with the primary antibody, secondary biotin-conjugated donkey anti-rabbit antibodies (Jackson) were applied for 30 minutes. After washing with PBS, slides were developed with diaminobenzidine (Dako, Mississauga, ON, Canada) as the chromogen. All slides were counterstained using Harris haematoxylin. The criterion for positive staining was described previously by Heaphy et al. (Altered telomeres in tumors with ATRX and DAXX mutations. Science 333 (6041), 425 (2011)). IHC staining on TMA was scored by three individuals independently, including a pathologist. To test the level of mono-, di- and tri-methylated HP at position K36, cell lysates from tumor cells were analysed by Western Blot. Antibodies against H3K36me3 (Abcam. Cat. #: ab9050), H3K36me2 (Abcam, Cat. #: ab9049), H3K36me1 (Abcam, Cat. #: ab9048) and H3.3 (Abcam, Cat. #: ab97968) were used, with conditions suggested by the manufacturer.

TABLE 1

Presentation of the characteristics of the 48 samples analyzed by whole exome sequencing.

| Sample ID | Age | Gender | Tumor location | Death | OS (months) | Recurrence | PFS (months) | GEP-Affi | SNP 2.5M Illumina |
|---|---|---|---|---|---|---|---|---|---|
| PGBM1 | 13 | F | thalamic | NA | NA | NA | NA | YES | NO |
| PGBM2 | 5 | M | left temporo-parietal | NO | 55 | NO | 55 | YES | NO |
| PGBM3 | 11 | M | intraventribular (I-II) | YES | 14 | YES | 12 | YES | NO |
| PGBM4 | 10 | M | thalamus + lateral ventricle | YES | 12 | YES | 7 | YES | NO |
| PGBM5 | 9 | F | NA | YES | 13 | YES | 9 | YES | NO |
| PGBM6 | 11 | M | thalamus | YES | 7 | NO | 6 | YES | NO |
| PGBM8 | 6 | F | NA | NO | 117 | NO | 117 | NO | NO |
| PGBM9 | 8 | F | NA | NA | NA | NA | NA | YES | NO |
| PGBM10 | 11 | M | NA | NO | 8 | NA | NA | NO | NO |
| PGBM11 | 13 | M | multiforme | YES | 7 | NO | 6 | YES | NO |
| PGBM12 | 14 | M | left temporal lobe | NA | NA | NA | NA | YES | NO |
| PGBM13 | 14 | M | occipital lobe | NA | NA | NA | NA | YES | NO |
| PGBM14 | 15 | M | right temporo-parietal | NA | NA | NA | NA | YES | NO |
| PGBM15 | 13 | M | NA | NA | NA | NA | NA | YES | NO |
| PGBM16 | 20 | F | parietal occipital | YES | 34 | YES | 22 | NO | YES |
| PGBM17 | 17 | M | left frontal and axial | NO | 27 | NO | 27 | NO | YES |
| PGBM18 | 14 | M | temporal lobe | YES | 13 | YES | 5 | NO | YES |
| PGBM19 | 20 | M | NA | YES | 18 | NO | 11 | YES | YES |
| PGBM20 | 11 | M | NA | YES | 37 | YES | 23 | NO | NO |
| PGBM21 | 14 | F | temporal lobe | YES | 11 | YES | 10 | NO | YES |
| PGBM22 | NA | NA | NA | YES | 12 | YES | 10 | YES | YES |
| PGBM23 | 13 | M | NA | YES | 5 | YES | 5 | YES | YES |
| PGBM24 | 14 | M | NA | YES | 10 | YES | 9 | YES | YES |
| PGBM25 | 12 | M | temporal lobe | YES | 6 | YES | 4 | YES | YES |
| PGBM26 | 14 | M | NA | YES | 10 | YES | 9 | YES | YES |
| PGBM27 | 9 | F | NA | YES | NA | YES | 7 | YES | YES |
| PGBM28 | 14 | M | left temporo-parietal | YES | NA | YES | 7 | NO | YES |
| PGBM29 | 15 | M | NA | NA | NA | NA | NA | YES | YES |
| PGBM30 | 6 | M | thalamic | YES | 12 | YES | 8 | YES | YES |
| PGBM31 | 7 | F | NA | YES | 17 | YES | 15 | NO | YES |
| PGBM32 | 4 | M | NA | NA | NA | NA | NA | YES | NO |
| PGBM33 | 12 | M | NA | NA | NA | YES | NA | NO | YES |
| PGBM34 | 12 | F | NA | YES | 14 | YES | 5 | YES | YES |
| PGBM35 | 7.3 | M | parietal lobe | YES | 8 | YES | 4 | YES | YES |
| PGBM36 | 7 | M | NA | NA | NA | NA | NA | NO | YES |
| PGBM37 | 7 | M | left cerebellar | NO | 27 | NO | 27 | NO | YES |
| PGBM38 | 11 | M | NA | YES | 25 | YES | 15 | NO | YES |
| PGBM39 | 12 | F | parietal lobe | YES | 36 | YES | 18 | NO | YES |
| PGBM40 | 14 | F | thalamus | NO | 14 | NA | NA | NO | YES |
| PGBM41 | 7 | F | left thalamus | YES | NA | YES | 7 | NO | NO |

TABLE 1-continued

Presentation of the characteristics of the 48 samples analyzed by whole exome sequencing.

| Sample ID | Age | Gender | Tumor location | Death | OS (months) | Recurrence | PFS (months) | GEP-Affi | SNP 2.5M Illumina |
|---|---|---|---|---|---|---|---|---|---|
| PGBM42 | 2 | F | NA | YES | 8 | NA | NA | NO | YES |
| PGBM43 | 16 | F | multiforme | YES | 12 | YES | 8 | NO | YES |
| PGBM44 | 6 | F | NA | NO | 24 | NA | NA | YES | YES |
| PGBM45 | 9 | M | right frontal | YES | 8 | NA | NA | NO | YES |
| PGBM46 | 14 | M | NA | YES | 7 | NA | NA | YES | YES |
| PGBM47 | 14 | F | NA | NO | 16 | NA | NA | YES | YES |
| PGBM48 | 2 | M | NA | YES | 5 | NA | NA | YES | YES |
| PGBM49 | 5.4 | M | frontal lobe | NO | 17 | NO | 17 | YES | YES |

OS = overall survival, PFS = progression-free survival.

Gene Expression Profiling. Total RNA from frozen samples were hybridized to the Affymetrix-HG-U133 plus 2.0 genechips (Affymetrix, Santa Clara, Calif.). Array quality assurance was determined using β-actin and GAPDH 3'/5' ratio, as recommended by the manufacturer.

Genome-wide SNP Array. DNA from 31 of the 49 pediatric GBM tumors analyzed by whole exome sequencing was hybridized to Illumina HUMAN OMNI™ 2.5M Single Nucleotide Polymorphism (SNP) arrays, according to the manufacturer's protocol. Copy Number Alterations were analyzed using Illumina GENOMESTUDIO™ Data Analysis Software (Illumina) as previously described by Peiffer et al. (High-resolution genomic profiling of chromosomal aberrations using Infinium whole-genome genotyping. Genome Res 16(9), 1136-1148 (2006)). Statistical analysis of Fisher's exact test was performed using GRAPHPAD PRISM™ software.

Telomere specific fluorescence in situ hybridization (FISH). Telomere specific FISH was done using a standard formalin-fixed parrafin embedded FISH protocol (as described in Heaphy et al. (supra)), using an FITC PNA Telomere probe from Dako.

Analysis of Alternative Lengthening of Telomere length (ALT). ALT was determined by Telomere Restriction Fragment analysis using the non-radioactive chemiluminescent assay kit (TELOTAGGG™ Telomere Length Assay, Roche Diagnostics GmbH, Mannheim, Germany). Briefly, extracted DNA samples (1-2 mg of tumor DNA) were digested with the restriction enzymes RsaI and HinfI at 37° C. for 2 hours and run on 0.8% agarose gels at 10 V for 18 hours. A biotinylated gamma DNA molecular weight marker was used as DNA length standard. High- and low-molecular-weight DNA were run as positive controls. The DNA samples were depurinated in 0.25 M HCl, denatured in 0.4 M NaOH/3 M NaCl, and transferred to a positively charged nylon membrane HYBOND-N™ (Amersham Pharmacia Biotech, Little Chalfont, England, UK) by capillary blotting over 12 hours. The membrane was washed in saline-sodium citrate buffer. The blot was hybridized with a (TTAGGG)$_3$ (SEQ ID NO: 13) telomere probe at 42° C. for 3 hours and washed in 2×SSC/0.1% sodium dodecyl sulfate. Chemiluminescent detection was performed according to the Detection Kit (Roche Diagnostics). Detection was performed on an X-ray HYPERFILM EC™. To address the issue of tissue heterogeneity, mean TRF lengths were calculated as e(ODi)/e(ODi/Li). The final number represents the mean molecular size of 36 equal intervals of telomeric smears in the range of 2 to 20 kb, as defined by DNA length standard. ODi reflects the measured intensity of luminescence in each of the 35 intervals. As reported in the literature, TRF lengths were recorded as telomere lengths.

Example II

Characterization of Histone Protein-Associated Mutations

The material and methods used in this Example are those presented in Example I.

To decipher the molecular pathogenesis of pediatric glioblastoma multiforme (GBM), we undertook a comprehensive mutation analysis in protein-coding genes by performing whole-exome sequencing (WES) on 48 well-characterized pediatric GBMs, including 6 patients for whom we had matched non-tumor (germline) DNA. Samples from the tumor core containing more than 90% neoplastic tissue were collected from patients aged between 3 and 20 years (Table 1). Coding regions of the genome were enriched by capture with the Illumina TRUSEQ™ kit and sequenced with 100 bp paired-end reads on an Illumina HISEQ™ 2000 platform. The median coverage of each base in the targeted regions was 61-fold, and 91% of the bases were represented by at least 10 reads (Table 2). We identified 87 somatic mutations in 80 genes among the 6 tumors for which we had matched constitutive DNA. The mutation count per tumor ranged from 3 to 31, with a mean of 15 (Table 3). This is much lower than the rate observed using Sanger sequencing in other solid tumors including adult GBM17, but somewhat higher than in another pediatric brain tumor, medulloblastoma 22 (Table 4). Relevant mutations (as defined below) were validated by Sanger sequencing.

Figure 1B:
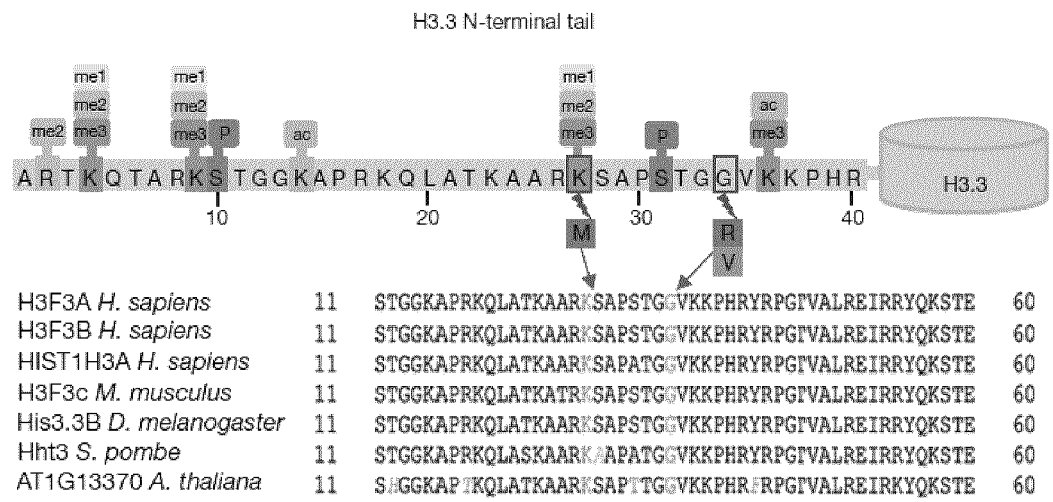
Figure 1C:
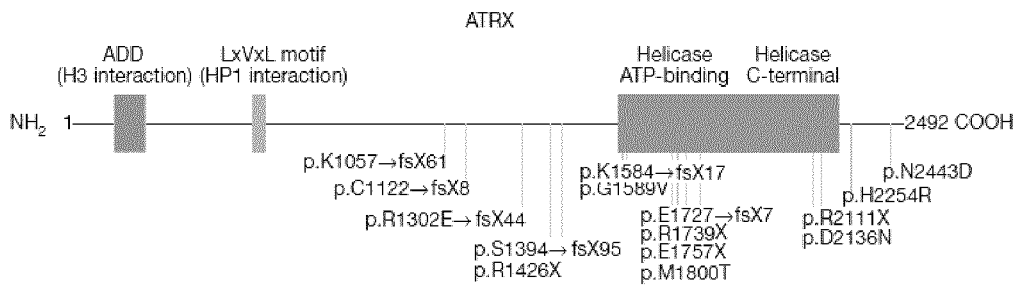
Figure 1D:
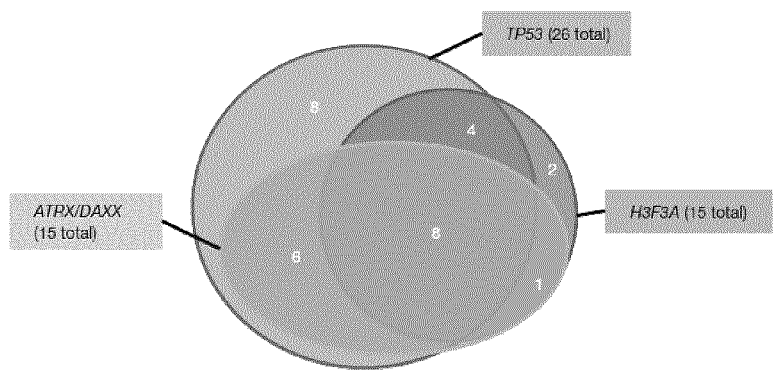

Initially, we focused on the distribution of somatic, non-silent protein-coding mutations in the six tumors with matched germline DNA. Four samples had recurrent heterozygous mutations in H3F3A, which encodes the replication-independent histone variant H3.3. Both mutations were single nucleotide variants (SNVs), in two samples changing lysine 27 to methionine (K27M), and in two samples changing glycine 34 to arginine (G34R) (FIG. 1A, Table 3). These mutations seem particularly interesting since histone genes are highly conserved throughout eukaryotes (FIG. 1B), and to our knowledge no human disorders have specifically been associated with mutations in histones, including H3.3. Both mutations are at or very near positions in the N-terminal tail of the protein that undergo important post-translational modifications associated with either transcriptional repression (K27) or activation (K36) (FIG. 1B). All four samples additionally harboured mutations in ATRX, which encodes a member of a transcription/chromatin remodeling complex required for the incorporation of H3.3 at pericentric heterochromatin and at telomeres, as well as at several transcription factor binding sites. We extended our WES analysis to 42 additional tumor samples and focused on ATRX and H3F3A, as well as DAXX (since the gene product heterodimerizes with ATRX and participates in H3.3 recruitment to DNA). A total of 15 samples had heterozygous H3.3 mutations (9 K27M, 5 G34R, 1 G34V) and 14 samples had a mutation in ATRX, including frameshift insertions/deletions (6 samples), gains of a stop codon (4 samples), and missense SNVs (4 samples). Nearly all of the ATRX mutations occurred either within the carboxy-terminal helicase domain or led to truncation of the protein upstream of this domain (FIG. 1C). Mutations were accompanied by an absence of detectable ATRX protein by immunohistochemistry in samples for which paraffin material was available (FIG. 2). Two samples had heterozygous DAXX mutations, simultaneous with an ATRX mutation in one sample (FIG. 1A, Table 3). Overall, 21 of 48 samples (44%) had a mutation in at least one of these three genes. Notably, we also identified TP53 mutations in 26 samples (25 somatic, 1 germline in PGBM26), which overlapped significantly with samples that had ATRX, DAXX and/or H3F3A mutations (18/21 cases, 86%, FIG. 1D; $p=1.1 \times 10^{-4}$, permutation test). A list of all mutations discovered by WES in selected genes associated with GBM is provided in Table 5.

TABLE 2

Sequencing data and coverage of the samples analyzed.

| Sample | Bases sequenced (after quality filtering) | Median # of reads per base in CCDS | Median # of reads per base in CCDS after duplicate removal | CCDS bases with at least 10 reads (%) |
|---|---|---|---|---|
| PGBM1 | 13 505 091 987 | 94 | 85 | 92.4 |
| PGBM2 | 17 119 601 726 | 109 | 70 | 91.3 |
| PGBM3 | 17 792 909 823 | 111 | 72 | 91.0 |
| PGBM4 | 13 363 577 977 | 64 | 52 | 90.5 |
| PGBM4-blood | 14 066 040 787 | 74 | 59 | 91.9 |
| PGBM5 | 14 504 723 839 | 75 | 43 | 88.9 |
| PGBM6 | 12 287 727 427 | 59 | 46 | 88.1 |
| PGBM6-blood | 13 999 868 369 | 67 | 53 | 88.9 |
| PGBM8 | 12 897 621 735 | 109 | 88 | 93.5 |
| PGBM9 | 12 045 904 509 | 104 | 85 | 93.1 |
| PGBM10 | 11 619 534 201 | 100 | 82 | 93.1 |
| PGBM11 | 16 935 710 296 | 112 | 104 | 93.9 |
| PGBM12 | 18 612 864 498 | 95 | 56 | 91.1 |
| PGBM13 | 10 904 833 155 | 51 | 41 | 87.3 |
| PGBM13-blood | 13 552 900 813 | 73 | 58 | 91.9 |
| PGBM14 | 15 701 377 658 | 86 | 53 | 91.0 |
| PGBM14-blood | 10 213 821 624 | 50 | 30 | 83.4 |
| PGBM15 | 10 582 247 277 | 86 | 67 | 92.1 |
| PGBM16 | 11 521 709 389 | 106 | 80 | 92.3 |
| PGBM17 | 12 870 074 056 | 68 | 57 | 91.9 |
| PGBM18 | 16 596 170 697 | 113 | 104 | 94.3 |
| PGBM19 | 12 687 545 184 | 65 | 53 | 91.3 |
| PGBM20 | 13 400 490 858 | 69 | 56 | 91.5 |

TABLE 2-continued

Sequencing data and coverage of the samples analyzed.

| Sample | Bases sequenced (after quality filtering) | Median # of reads per base in CCDS | Median # of reads per base in CCDS after duplicate removal | CCDS bases with at least 10 reads (%) |
|---|---|---|---|---|
| PGBM21 | 16 068 676 400 | 102 | 95 | 93.8 |
| PGBM22 | 11 061 729 809 | 93 | 74 | 92.8 |
| PGBM23 | 14 088 721 409 | 68 | 44 | 89.1 |
| PGBM24 | 10 190 203 445 | 49 | 41 | 87.9 |
| PGBM25 | 12 094 215 054 | 62 | 52 | 90.5 |
| PGBM26 | 19 718 043 045 | 123 | 81 | 91.7 |
| PGBM27 | 17 672 965 295 | 98 | 62 | 90.5 |
| PGBM28 | 13 235 175 617 | 88 | 65 | 92.0 |
| PGBM29 | 4 376 261 391 | 38 | 22 | 83.9 |
| PGBM30 | 11 331 964 823 | 100 | 78 | 92.5 |
| PGBM31 | 9 457 007 712 | 48 | 29 | 85.4 |
| PGBM32 | 15 996 029 641 | 101 | 94 | 94.1 |
| PGBM33 | 10 601 377 271 | 89 | 72 | 92.7 |
| PGBM34 | 9 753 010 363 | 46 | 27 | 83.7 |
| PGBM35 | 16 828 099 833 | 115 | 68 | 91.3 |
| PGBM36 | 12 731 008 997 | 68 | 38 | 88.2 |
| PGBM37 | 20 336 444 728 | 134 | 78 | 92.9 |
| PGBM38 | 9 929 368 120 | 51 | 29 | 85.5 |
| PGBM39 | 13 628 886 633 | 65 | 52 | 89.7 |
| PGBM40-blood | 13 251 854 585 | 71 | 59 | 91.4 |
| PGBM40 | 11 824 281 050 | 58 | 46 | 87.2 |
| PGBM41-blood | 14 095 936 522 | 68 | 53 | 88.5 |
| PGBM41 | 17 799 081 592 | 120 | 78 | 91.3 |
| PGBM42 | 12 032 711 376 | 64 | 54 | 89.9 |
| PGBM43 | 14 904 682 891 | 88 | 80 | 92.4 |
| PGBM44 | 14 651 870 734 | 102 | 94 | 93.6 |
| PGBM45 | 17 328 188 664 | 90 | 60 | 91.7 |
| PGBM46 | 10 137 136 155 | 82 | 69 | 92.7 |
| PGBM47 | 10 003 457 301 | 80 | 66 | 92.3 |
| PGBM48 | 12 519 238 552 | 111 | 91 | 93.4 |
| PGBM49 | 11 864 031 610 | 103 | 81 | 92.5 |

TABLE 3A

Somatic mutations identified in the 6 paired tumor/normal samples examined by WES. Tumor variants were considered to be somatic when matched normal had more than >=10 reads and 0 variant reads.

| | # Somatic mutations | | |
|---|---|---|---|
| Sample | Normal has >= 0 reads | Normal has >= 5 reads | Normal has >= 10 reads** |
| PGBM6 | 20 | 17 | 13 |
| PGBM13 | 32 | 32 | 31 |
| PGBM4 | 14 | 12 | 12 |
| PGBM39 | 19 | 19 | 16 |
| PGBM14 | 29 | 18 | 14 |
| PGBM40 | 10 | 6 | 3 |

**Variants shown in Table 3B below

TABLE 3B

Characterization of the variants of Table 3A.

| Sample | Gene | Transcript accession | Nucleotide variant | Amino acid change | Mutation type |
|---|---|---|---|---|---|
| PGBM6 | AHNAK | NM_001620.1 | c.10565C > T | p.(Pro3522Leu) | nonsynonymous SNV |
| PGBM39 | AHRR | NM_020731.4 | c.496G > A | p.(Asp166Asn) | nonsynonymous SNV |
| PGBM14 | ATRX | NM_000489.3 | c.5269G > T | p.(Glu1757*) | stopgain SNV |
| PGBM4 | ATRX | NM_000489.3 | c.3168delG | p.(Lys1057Argfs*61) | frameshift deletion |
| PGBM13 | ATRX | NM_000489.3 | c.5215C > T | p.(Arg1739*) | stopgain SNV |
| PGBM6 | ATRX | NM_000489.3 | c.5399T > C | p.(Met1800Thr) | nonsynonymous SNV |

TABLE 3B-continued

Characterization of the variants of Table 3A.

| Sample | Gene | Transcript accession | Nucleotide variant | Amino acid change | Mutation type |
|---|---|---|---|---|---|
| PGBM13 | BMPER | NM_133468.3 | c.1476G > T | p.(Lys492Asn) | nonsynonymous SNV |
| PGBM39 | BRAF | NM_004333.4 | c.1799T > A | p.(Val600Glu) | nonsynonymous SNV |
| PGBM13 | C13orf40 | NM_001146197.1 | c.3703G > C | p.(Glu1235Gln) | nonsynonymous SNV |
| PGBM13 | C20orf195 | NM_024059.2 | c.16G > T | p.(Ala6Ser) | nonsynonymous SNV |
| PGBM13 | C8orf73 | NM_001100878.1 | c.1933G > A | p.(Asp645Asn) | nonsynonymous SNV |
| PGBM13 | CD5L | NM_005894.2 | c.568C > T | p.(Arg190Cys) | nonsynonymous SNV |
| PGBM13 | CHMP7 | NM_152272.3 | c.1012G > T | p.(Asp338Tyr) | nonsynonymous SNV |
| PGBM13 | CMYA5 | NM_153610.3 | c.2674C > T | p.(Arg892*) | stopgain SNV |
| PGBM39 | COL19A1 | NM_001858.4 | c.1969A > T | p.(Thr657Ser) | nonsynonymous SNV |
| PGBM13 | CR2 | NM_001006658.2 | c.1559G > A | p.(Arg520His) | nonsynonymous SNV |
| PGBM14 | CSMD3 | NM_198123.1 | c.1352C > A | p.(Ala451Asp) | nonsynonymous SNV |
| PGBM39 | DSPP | NM_014208.3 | c.3447A > C | p.(Glu1149Asp) | nonsynonymous SNV |
| PGBM6 | DUSP6 | NM_001946.2 | c.848G > A | p.(Arg283Gln) | nonsynonymous SNV |
| PGBM40 | EIF4E1B | NM_001099408.1 | c.140G > A | p.(Gly47Glu) | nonsynonymous SNV |
| PGBM14 | FBXW7 | NM_033632.2 | c.566_567del | p.(Lys189Serfs*66) | frameshift deletion |
| PGBM4 | FCGBP | NM_003890.2 | c.14369G > A | p.(Gly4790Asp) | nonsynonymous SNV |
| PGBM6 | FGFR1 | NM_023110.2 | c.1966A > G | p.(Lys656Glu) | nonsynonymous SNV |
| PGBM39 | GNAS | NM_001077490.1 | c.644C > T | p.(Ser215Phe) | nonsynonymous SNV |
| PGBM39 | GPR172A | NM_024531.3 | c.1052G > A | p.(Gly351Asp) | nonsynonymous SNV |
| PGBM4 | GRIPAP1 | NM_020137.3 | c.2414A > G | p.(Lys805Arg) | nonsynonymous SNV |
| PGBM4 | GYS2 | NM_021957.3 | c.1889C > T | p.(Thr630Met) | nonsynonymous SNV |
| PGBM4 | H3F3A | NM_002107.4 | c.83A > T | p.(Lys28Met) | nonsynonymous SNV |
| PGBM6 | H3F3A | NM_002107.4 | c.83A > T | p.(Lys28Met) | nonsynonymous SNV |
| PGBM13 | H3F3A | NM_002107.4 | c.103G > A | p.(Gly35Arg) | nonsynonymous SNV |
| PGBM14 | H3F3A | NM_002107.4 | c.103G > A | p.(Gly35Arg) | nonsynonymous SNV |
| PGBM13 | HMX3 | NM_001105574.1 | c.622G > T | p.(Gly208Cys) | nonsynonymous SNV |
| PGBM13 | HOOK1 | NM_015888.4 | c.206A > G | p.(Asp69Gly) | nonsynonymous SNV |
| PGBM14 | KCNS2 | NM_020697.2 | c.395_397del | p.(Glu133del) | nonframeshift deletion |
| PGBM13 | KIAA1217 | NM_019590.3 | c.3988G > A | p.(Val1330Met) | nonsynonymous SNV |
| PGBM4 | KIAA1826 | NM_032424.1 | c.904C > T | p.(Arg302*) | stopgain SNV |
| PGBM39 | KRT27 | NM_181537.3 | c.167G > A | p.(Gly56Glu) | nonsynonymous SNV |
| PGBM40 | LOXL4 | NM_032211.6 | c.247G > T | p.(Ala83Ser) | nonsynonymous SNV |
| PGBM6 | LPHN2 | NM_012302.2 | c.3287C > A | p.(Pro1096Gln) | nonsynonymous SNV |
| PGBM39 | LRP1 | NM_002332.2 | c.2218G > T | p.(Pro740Ser) | nonsynonymous SNV |
| PGBM13 | LSP1 | NM_002339.2 | c.970G > A | p.(Gly324Arg) | nonsynonymous SNV |
| PGBM39 | LUM | NM_002345.3 | c.547C > T | p.(Leu183Phe) | nonsynonymous SNV |
| PGBM4 | LYPD5 | NM_001031749.2 | c.695G > A | p.(Arg232Gln) | nonsynonymous SNV |
| PGBM14 | MARK1 | NM_018650.3 | c.1259G > A | p.(Arg420Gln) | nonsynonymous SNV |
| PGBM14 | MFGE8 | NM_005928.2 | c.118_120del | p.(Glu40del) | nonframeshift deletion |
| PGBM40 | MTF1 | NM_005955.2 | c.1532C > A | p.(Ala511Glu) | nonsynonymous SNV |
| PGBM13 | MTUS2 | NM_001033602.2 | c.1472C > T | p.(Thr491Met) | nonsynonymous SNV |
| PGBM13 | MYO5C | NM_018728.3 | c.4626C > A | p.(Asp1542Glu) | nonsynonymous SNV |
| PGBM39 | NCAM2 | NM_004540.3 | c.2230A > G | p.(Ser744Gly) | nonsynonymous SNV |
| PGBM4 | NDST2 | NM_003635.3 | c.329G > A | p.(Arg110His) | nonsynonymous SNV |
| PGBM6 | NF1 | NM_001042492.2 | c.3735_3744del | p.(Phe1247Glyfs*16) | frameshift deletion |
| PGBM6 | NF1 | NM_001042492.2 | c.6746_6748del | p.(Val2251del) | nonframeshift deletion |
| PGBM13 | NLRP2 | NM_017852.3 | c.1379C > T | p.(Ala460Val) | nonsynonymous SNV |
| PGBM6 | OR1E1 | NM_003553.2 | c.437C > T | p.(Ala146Val) | nonsynonymous SNV |
| PGBM13 | OR4C6 | NM_001004704.1 | c.662G > T | p.(Cys221Phe) | nonsynonymous SNV |
| PGBM6 | OR51A7 | NM_001004749.1 | c.136C > T | p.(Leu46Phe) | nonsynonymous SNV |
| PGBM4 | PCDHB14 | NM_018934.2 | c.1966G > A | p.(Ala656Thr) | nonsynonymous SNV |
| PGBM14 | PHF3 | NM_015153.2 | c.310_312del | p.(Glu106del) | nonframeshift deletion |
| PGBM4 | PIK3C2A | NM_002645.2 | c.458C > T | p.(Ala153Val) | nonsynonymous SNV |
| PGBM13 | PRIC285 | NM_001037335.2 | c.4842C > A | p.(Asp1614Glu) | nonsynonymous SNV |
| PGBM6 | PTEN | NM_000314.4 | c.634-2A > C | splicing | splicing |
| PGBM13 | PTGDR | NM_000953.2 | c.146G > T | p.(Cys49Phe) | nonsynonymous SNV |
| PGBM39 | RAB23 | NM_016277.3 | c.551C > T | p.(Thr184Met) | nonsynonymous SNV |
| PGBM13 | RANBP2 | NM_006267.4 | c.7106G > A | p.(Arg2369His) | nonsynonymous SNV |
| PGBM13 | RERE | NM_001042681.1 | c.8C > T | p.(Ala3Val) | nonsynonymous SNV |
| PGBM13 | RGMA | NM_020211.2 | c.1248G > T | p.(Arg416Ser) | nonsynonymous SNV |
| PGBM13 | RHOBTB1 | NM_014836.4 | c.1502C > T | p.(Pro501Leu) | nonsynonymous SNV |
| PGBM13 | RYR2 | NM_001035.2 | c.13130C > T | p.(Ser4377Leu) | nonsynonymous SNV |
| PGBM39 | SDHA | NM_004168.2 | c.772G > C | p.(Gly258Arg) | nonsynonymous SNV |
| PGBM14 | SESN3 | NM_144665.2 | c.649_650del | p.(Asp217Serfs*19) | frameshift deletion |
| PGBM13 | SFXN4 | NM_213649.1 | c.971C > A | p.(Ser324Tyr) | nonsynonymous SNV |
| PGBM14 | TKT | NM_001135055.2 | c.1644C > T | p.(Trp548Cys) | nonsynonymous SNV |
| PGBM6 | TMC2 | NM_080751.2 | c.2173C > A | p.(Pro725Thr) | nonsynonymous SNV |
| PGBM13 | TMEM132D | NM_133448.2 | c.89G > T | p.(Gly30Val) | nonsynonymous SNV |
| PGBM6 | TNP2 | NM_005425.4 | c.62C > T | p.(Pro21Leu) | nonsynonymous SNV |
| PGBM14 | TP53 | NM_000546.4 | c.817C > T | p.(Arg273Cys) | nonsynonymous SNV |
| PGBM14 | TP53 | NM_000546.4 | c.743G > A | p.(Arg248Gln) | nonsynonymous SNV |
| PGBM4 | TP53 | NM_000546.4 | c.785delG | p.(Gly262Valfs*83) | frameshift deletion |
| PGBM13 | TP53 | NM_000546.4 | c.767delC | p.(Thr256Asnfs*89) | frameshift deletion |
| PGBM39 | TRIM28 | NM_005762.2 | c.499G > A | p.(Val167Met) | nonsynonymous SNV |
| PGBM13 | TTN | NM_133378.4 | c.2406C > A | p.(Phe8020Leu) | nonsynonymous SNV |
| PGBM4 | UBE2I | NM_194261.2 | c.28G > A | p.(Ala10Thr) | nonsynonymous SNV |

TABLE 3B-continued

Characterization of the variants of Table 3A.

| Sample | Gene | Transcript accession | Nucleotide variant | Amino acid change | Mutation type |
|---|---|---|---|---|---|
| PGBM13 | UBE3A | NM_000462.3 | c.1619T > G | p.(Leu540Arg) | nonsynonymous SNV |
| PGBM14 | URB2 | NM_014777.2 | c.156G > T | p.(Leu52Phe) | nonsynonymous SNV |
| PGBM39 | USP26 | NM_031907.1 | c.2138T > A | p.(Ile713Asn) | nonsynonymous SNV |
| PGBM13 | ZCCHC4 | NM_024936.2 | c.100G > T | p.(Ala34Ser) | nonsynonymous SNV |
| PGBM14 | ZCCHC5 | NM_152694.2 | c.1085A > T | p.(Gln362Leu) | nonsynonymous SNV |
| PGBM39 | ZNF622 | NM_033414.2 | c.525G > T | p.(Glu175Asp) | nonsynonymous SNV |
| PGBM39 | ZNF622 | NM_033414.2 | c.327G > C | p.(Met109Ile) | nonsynonymous SNV |

TABLE 4

Comparison of somatic mutation rate in pediatric GBM with adult GBM and four other types of cancer.
Summary of somatic mutations in pediatric glioblastoma and 5 cancer types from Parsons et al.

| | Pediatric Glioblastoma | Adult Glioblastoma | Medulloblastoma | Pancreas | Colorectal | Breast |
|---|---|---|---|---|---|---|
| Number of samples analyzed | 6 | 21 | 22 | 24 | 11 | 11 |
| Number of mutated genes | 80 | 685 | 218 | 1007 | 769 | 1026 |
| Number of nonsilent mutations | 87 | 748 | 183 | 1163 | 849 | 1112 |
| Missense | 71 (81.6%) | 622 (83.2%) | 130 (71.0%) | 974 (83.7%) | 722 (85%) | 909 (81.7%) |
| Nonsense | 4 (4.6%) | 43 (5.7%) | 18 (9.8%) | 60 (5.2%) | 48 (5.7%) | 64 (5.8%) |
| Insertion | 0 | 3 (0.4%) | 5 (2.7%) | 4 (0.3%) | 4 (0.5%) | 5 (0.4%) |
| Deletion | 10 (11.5%) | 46 (6.1%) | 14 (7.7%) | 43 (3.7%) | 27 (3.2%) | 78 (7.0%) |
| Duplication | 0 | 7 (0.9%) | 7 (3.8%) | 31 (2.7%) | 18 (2.1%) | 3 (0.3%) |
| Splice site or untranslated region | 2 (2.3%) | 27 (3.6%) | 9 (4.9%) | 51 (4.4%) | 30 (3.5%) | 53 (4.8%) |
| Average number of nonsilent mutations per sample | 15 | 36 | 8 | 48 | 77 | 101 |
| Observed/expected number of nonsense alterations | | 1 | 2.48 | 1.18 | 1.25 | 1.37 |
| Total number of substitutions# | 77 | 937 | 199 | 1486 | 893 | 1157 |
| Substitutions at C:G base pairs | | | | | | |
| C:G to T:A** | 40 (50.6%) | 601 (64.1%) | 109 (54.8%) | 798 (53.8%) | 534 (59.8%) | 422 (36.5%) |
| C:G to G:C** | 3 (3.8%) | 67 (7.2%) | 12 (6.0%) | 142 (9.6%) | 61 (6.8%) | 325 (28.1%) |
| C:G to A:T** | 21 (26.6%) | 114 (12.1%) | 41 (20.6%) | 246 (16.6%) | 130 (14.6%) | 175 (15.1%) |
| Substitutions at T:A base pairs | | | | | | |
| T:A to C:G** | 5 (6.3%) | 87 (9.3%) | 19 (9.5%) | 142 (9.6%) | 69 (7.7%) | 102 (8.8%) |
| T:A to G:C** | 3 3.8%) | 24 (2.6%) | 14 (7.0%) | 79 (5.3%) | 59 (6.6%) | 57 (4.9%) |
| T:A to A:T** | 7 (8.9%) | 44 (4.7%) | 4 (2.0%) | 77 (5.2%) | 40 (4.5%) | 76 (6.6%) |
| Substitutions at specific dinucleotides | | | | | | |
| 5'-CpG-3'** | no data | 404 (43.1%) | 85 (42.7%) | 563 (37.9%) | 427 (47.8%) | 195 (16.9%) |
| 5'-TpC-3'** | no data | 102 (10.9%) | 14 (7.0%) | 218 (14.7%) | 99 (11.1%) | 395 (34.1%) |

TABLE 5

Mutations in selected genes H3F3A, ATRX, DAXX, IDH1, PDGFRA, EGFR, TP53 fof the samples analyzed by whole exome sequencing.

| Sample | Gene | Transcript accession | Nucleotide variant | Amino acid change | Mutation type |
|---|---|---|---|---|---|
| PGBM1 | H3F3A | NM_002107.4 | c.83A > T | p.(Lys27Met) | Missense |
| PGBM2 | H3F3A | NM_002107.4 | c.83A > T | p.(Lys27Met) | Missense |
| PGBM3 | H3F3A | NM_002107.4 | c.83A > T | p.(Lys27Met) | Missense |
| PGBM5 | H3F3A | NM_002107.4 | c.83A > T | p.(Lys27Met) | Missense |
| PGBM6 | H3F3A | NM_002107.4 | c.83A > T | p.(Lys27Met) | Missense |
| PGBM4 | H3F3A | NM_002107.4 | c.83A > T | p.(Lys27Met) | Missense |
| PGBM8 | H3F3A | NM_002107.4 | c.83A > T | p.(Lys27Met) | Missense |
| PGBM9 | H3F3A | NM_002107.4 | c.83A > T | p.(Lys27Met) | Missense |
| PGBM10 | H3F3A | NM_002107.4 | c.83A > T | p.(Lys27Met) | Missense |
| PGBM11 | H3F3A | NM_002107.4 | c.103G > A | p.(Gly34Arg) | Missense |
| PGBM14 | H3F3A | NM_002107.4 | c.103G > A | p.(Gly34Arg) | Missense |
| PGBM12 | H3F3A | NM_002107.4 | c.103G > A | p.(Gly34Arg) | Missense |
| PGBM13 | H3F3A | NM_002107.4 | c.103G > A | p.(Gly34Arg) | Missense |
| PGBM15 | H3F3A | NM_002107.4 | c.103G > A | p.(Gly34Arg) | Missense |
| PGBM16 | H3F3A | NM_002107.4 | c.104G > T | p.(Gly34Val) | Missense |
| PGBM1 | ATRX | NM_000489.3 | c.3364delT | p.(Cys1122Valfs*8) | Frameshift indel |
| PGBM4 | ATRX | NM_000489.3 | c.3168delG | p.(Lys1057Argfs*61) | Frameshift indel |
| PGBM6 | ATRX | NM_000489.3 | c.5399T > C | p.(Met1800Thr) | Missense |
| PGBM11 | ATRX | NM_000489.3 | c.4179_4182del | p.(Ser1394Asnfs*95) | Frameshift indel |
| PGBM12 | ATRX | NM_000489.3 | c.5178_5179insA | p.(Glu1727Argfs*7) | Frameshift indel |
| PGBM13 | ATRX | NM_000489.3 | c.5215C > T | p.(Arg1739*) | Nonsense |
| PGBM14 | ATRX | NM_000489.3 | c.5269G > T | p.(Glu1757*) | Nonsense |
| PGBM15 | ATRX | NM_000489.3 | c.6761A > G | p.(His2254Arg) | Missense |
| PGBM16 | ATRX | NM_000489.3 | c.6331C > T | p.(Arg2111*) | Nonsense |
| PGBM17 | ATRX | NM_000489.3 | c.4766G > T | p.(Gly1589Val) | Missense |
| PGBM18 | ATRX | NM_000489.3 | c.4276C > T | p.(Arg1426*) | Nonsense |
| PGBM19 | ATRX | NM_000489.3 | c.4745_4746insA | p.(Lys1584Glufs*17) | Frameshift indel |
| PGBM20 | ATRX | NM_000489.3 | c.7327A > G | p.(Asn2443Asp) | Missense |
| PGBM22 | ATRX | NM_000489.3 | c.4745_4746insA | p.(Lys1584Glufs*17) | Frameshift indel |
| PGBM22 | ATRX | NM_000489.3 | c.3904delA | p.(Arg1302Glufs*44) | Frameshift indel |
| PGBM22 | ATRX | NM_000489.3 | c.6406G > A | p.(Asp2136Asn) | Missense |
| PGBM19 | DAXX | NM_001350.4 | c.1885_1886insC | p.(Cys629Serfs*29) | Frameshift indel |
| PGBM21 | DAXX | NM_001350.4 | c.712C > T | p.(Arg238*) | Nonsense |
| PGBM17 | IDH1 | NM_005896.2 | c.395G > A | p.(Arg132His) | Missense |
| PGBM18 | IDH1 | NM_005896.2 | c.395G > A | p.(Arg132His) | Missense |
| PGBM23 | IDH1 | NM_005896.2 | c.395G > A | p.(Arg132His) | Missense |
| PGBM29 | IDH1 | NM_005896.2 | c.395G > A | p.(Arg132His) | Missense |

TABLE 5-continued

Mutations in selected genes H3F3A, ATRX, DAXX, IDH1, PDGFRA, EGFR, TP53 fof the samples analyzed by whole exome sequencing.

| Sample | Gene | Transcript accession | Nucleotide variant | Amino acid change | Mutation type |
|---|---|---|---|---|---|
| PGBM2 | PDGFRA | NM_006206.4 | c.1154A > T | p.(Lys385Met) | Missense |
| PGBM16 | PDGFRA | NM_006206.4 | c.1154A > T | p.(Lys385Met) | Missense |
| PGBM34 | PDGFRA | NM_006206.4 | c.2525_2527del | p.(Asp842_Ile843delins-Val) | Nonframeshift indel |
| PGBM12 | PDGFRA | NM_006206.4 | c.2545T > G | p.(Tyr849Asp) | Missense |
| PGBM22 | EGFR | NM_005228.3 | c.2165C > T | p.(Ala722Val) | Missense |
| PGBM27 | EGFR | NM_005228.3 | c.2950G > A | p.(Asp984Asn) | Missense |
| PGBM1 | TP53 | NM_000546.4 | c.916C > T | p.(Arg306*) | Nonsense |
| PGBM1 | TP53 | NM_000546.4 | c.455_459del | p.(Pro152Argfs*27) | Frameshift indel |
| PGBM2 | TP53 | NM_000546.4 | c.637C > T | p.(Arg213*) | Nonsense |
| PGBM3 | TP53 | NM_000546.4 | c.393_395del | p.(Asn131del) | Nonframeshift indel |
| PGBM4 | TP53 | NM_000546.4 | c.785delG | p.(Gly262Valfs*83) | Frameshift indel |
| PGBM8 | TP53 | NM_000546.4 | c.817C > T | p.(Arg273Cys) | Missense |
| PGBM9 | TP53 | NM_000546.4 | c.818G > C | p.(Arg273Pro) | Missense |
| PGBM11 | TP53 | NM_000546.4 | c.488A > G | p.(Tyr163Cys) | Missense |
| PGBM12 | TP53 | NM_000546.4 | c.1024C > T | p.(Arg342*) | Nonsense |
| PGBM12 | TP53 | NM_000546.4 | c.524G > A | p.(Arg175His) | Missense |
| PGBM13 | TP53 | NM_000546.4 | c.767delC | p.(Thr256Asnfs*89) | Frameshift indel |
| PGBM14 | TP53 | NM_000546.4 | c.817C > T | p.(Arg273Cys) | Missense |
| PGBM14 | TP53 | NM_000546.4 | c.743G > A | p.(Arg248Gln) | Missense |
| PGBM15 | TP53 | NM_000546.4 | c.548_549 insGCCCCCACCATGAGCGCTGCT (SEQ ID NO: 9) | p.(Asp184_Asp393delins-ProProPro) | Nonframeshift indel |
| PGBM16 | TP53 | NM_000546.4 | c.1024C > T | p.(Arg342*) | Nonsense |
| PGBM17 | TP53 | NM_000546.4 | c.659A > G | p.(Tyr220Cys) | Missense |
| PGBM18 | TP53 | NM_000546.4 | c.586C > T | p.(Arg196*) | Nonsense |
| PGBM18 | TP53 | NM_000546.4 | c.817C > T | p.(Arg273Cys) | Missense |
| PGBM19 | TP53 | NM_000546.4 | c.800G > A | p.(Arg267Gln) | Missense |
| PGBM19 | TP53 | NM_000546.4 | c.689C > T | p.(Thr230Ile) | Missense |
| PGBM20 | TP53 | NM_000546.4 | c.742C > T | p.(Arg248Trp) | Missense |
| PGBM21 | TP53 | NM_000546.4 | c.799C > T | p.(Arg267Trp) | Missense |
| PGBM21 | TP53 | NM_000546.4 | c.455C > T | p.(Pro152Leu) | Missense |
| PGBM22 | TP53 | NM_000546.4 | c.1009C > T | p.(Arg337Cys) | Missense |
| PGBM22 | TP53 | NM_000546.4 | c.524G > A | p.(Arg175His) | Missense |
| PGBM23 | TP53 | NM_000546.4 | c.761T > G | p.(Ile254Ser) | Missense |
| PGBM24 | TP53 | NM_000546.4 | c.586C > T | p.(Arg196*) | Nonsense |
| PGBM25 | TP53 | NM_000546.4 | c.1024C > T | p.(Arg342*) | Nonsense |
| PGBM26 | TP53 | NM_000546.4 | c.524G > A | p.(Arg175His) | Missense |
| PGBM27 | TP53 | NM_000546.4 | c.751A > C | p.(Ile251Leu) | Missense |

TABLE 5-continued

Mutations in selected genes H3F3A, ATRX, DAXX, IDH1, PDGFRA, EGFR, TP53 fof the samples analyzed by whole exome sequencing.

| Sample | Gene | Transcript accession | Nucleotide variant | Amino acid change | Mutation type |
|---|---|---|---|---|---|
| PGBM28 | TP53 | NM_000546.4 | c.818G > A | p.(Arg273His) | Missense |
| PGBM29 | TP53 | NM_000546.4 | c.29T > G | p.(Val10Gly) | Missense |
| PGBM30 | TP53 | NM_000546.4 | c.733G > A | p.(Gly245Ser) | Missense |
| PGBM5 | NF1 | NM_000267.3 | c.6787_6790del | p.(Tyr2264Thrfs*5) | Frameshift indel |
| PGBM6 | NF1 | NM_000267.3 | c.3735_3744del | p.(Phe1247Glyfs*16) | Frameshift indel |
| PGBM6 | NF1 | NM_000267.3 | c.6683_6685del | p.(Val2230del) | Nonframeshift indel |
| PGBM10 | NF1 | NM_000267.3 | c.2970delA | p.(Met991*) | Nonsense |
| PGBM18 | NF1 | NM_000267.3 | c.1866T > A | p.(Cys622*) | Nonsense |
| PGBM18 | NF1 | NM_000267.3 | c.4466delT | p.(Leu1489Hisfs*64) | Frameshift indel |
| PGBM19 | NF1 | NM_000267.3 | c.1318C > T | p.(Arg440*) | Nonsense |
| PGBM21 | NF1 | NM_000267.3 | c.5839C > T | p.(Arg1947*) | Nonsense |
| PGBM22 | NF1 | NM_000267.3 | c.7846C > T | p.(Arg2616*) | Nonsense |
| PGBM22 | NF1 | NM_000267.3 | c.2659G > A | p.(Ala887Thr) | Missense |
| PGBM22 | NF1 | NM_000267.3 | c.1381C > T | p.(Arg461*) | Nonsense |
| PGBM25 | NF1 | NM_000267.3 | c.4575delG | p.(Gly1526Valfs*27) | Frameshift indel |
| PGBM26 | NF1 | NM_000267.3 | c.6787_6790del | p.(Tyr2264Thrfs*5) | Frameshift indel |
| PGBM28 | NF1 | NM_000267.3 | c.2026_2027insC | p.(Ile679Aspfs*21) | Frameshift indel |
| PGBM32 | NF1 | NM_000267.3 | c.4879A > T | p.(Thr1627Ser) | Missense |
| PGBM33 | NF1 | NM_000267.3 | c.1641 + 1G > T | | Splicing |

Figure 3B:
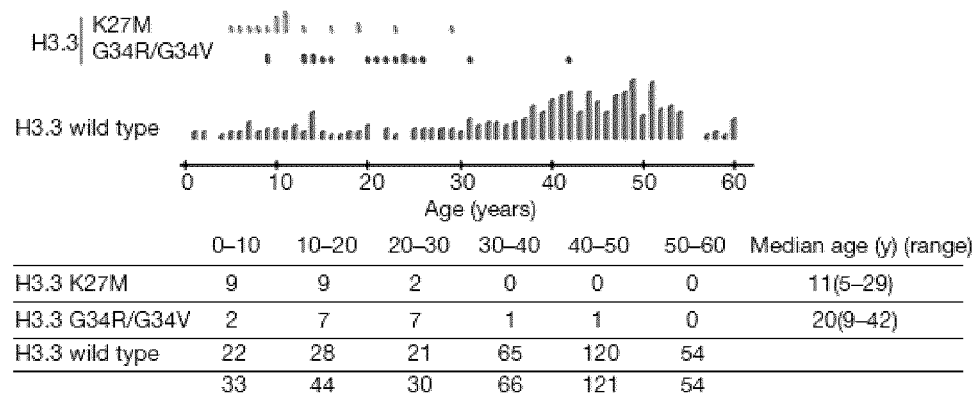
Figure 3C:
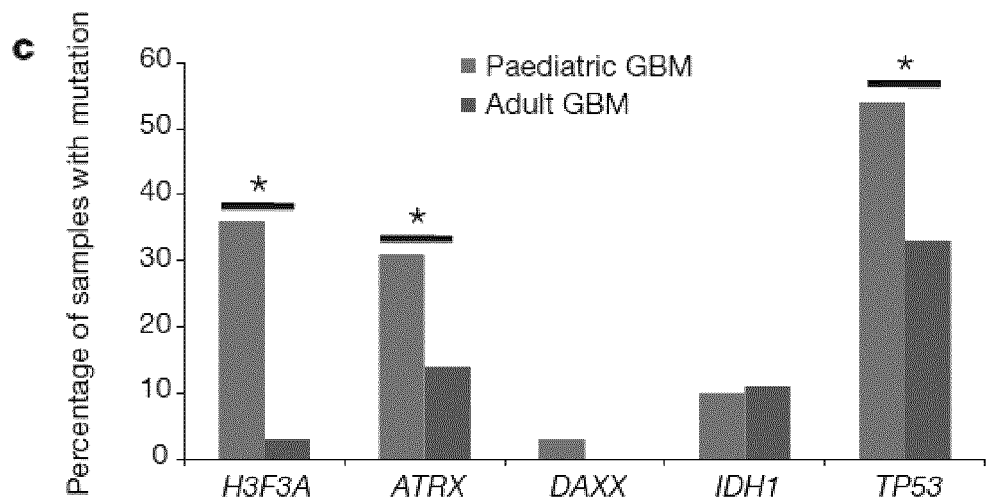
Figure 4B:
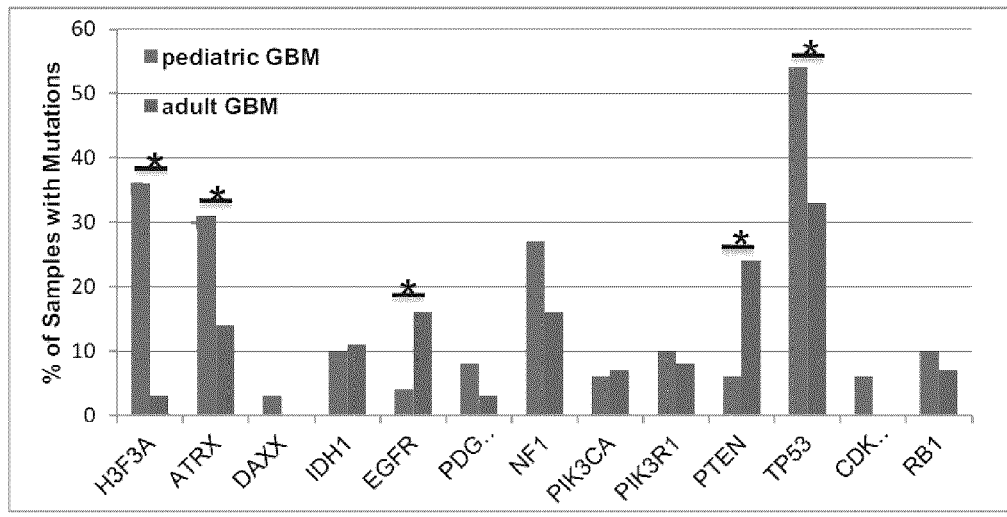

H3F3A. ATRX or DAXX were not part of the 600 genes sequenced by The Cancer Genome Atlas (TCGA) glioblastoma project, and no H3F3A mutations were identified in 22 adult GBM samples sequenced by Parsons et al. (An integrated genomic analysis of human glioblastoma multiforme. Science 321, 1807-1812, doi:1164382). To investigate whether H3F3A mutations are specific to GBM and/or pediatric disease, we sequenced this gene in 784 glioma samples from all grades and histological diagnoses across the entire age range (FIG. 3A). H3.3 mutations were highly specific to GBM and were much more prevalent in the pediatric setting (32/90, 36%), although they also occurred rarely in young adults with GBM (11/318, 3%) (FIG. 3B). K27M-H3.3 mutations occurred mainly in younger patients (median age 11 years, range 5-29) and thalamic GBM (Table 1), while G34R- or G34V-H3.3 mutations occurred in older patients (median age 20 years, range 9-42) and in tumors of the cerebral hemispheres (FIG. 3B). Further comparison of our dataset with adult GBM databases indicated limited overlap in frequently mutated genes between pediatric GBM and any of the four previously described adult GBM subtypes (FIG. 3C, FIG. 4. Table 6).

Figure 3D:
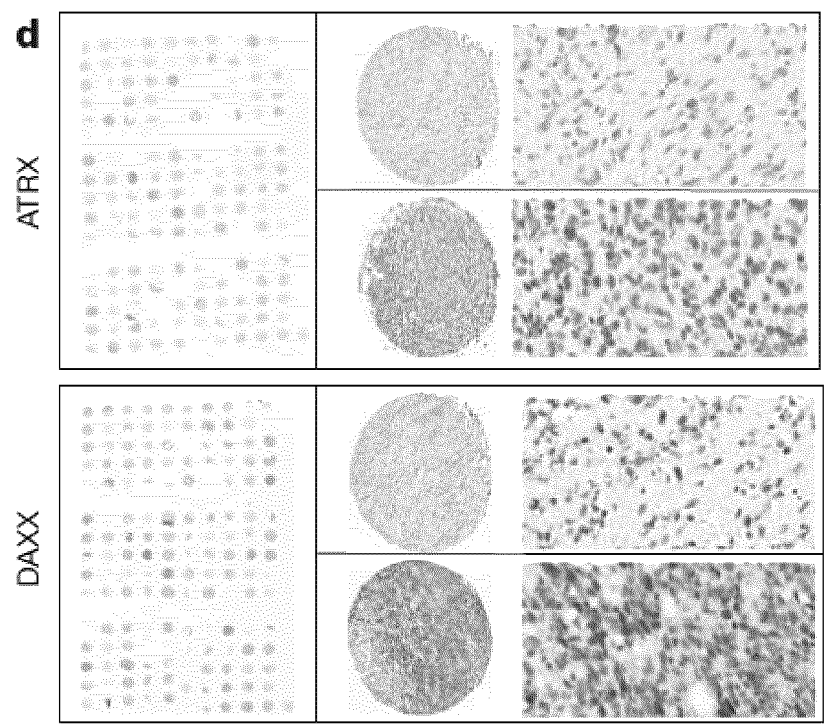

Somatic mutations in ATRX and DAXX have recently been reported in a large proportion (43%) of pancreatic neuroendocrine tumors (PanNETs), a rare form of pancreatic cancer with a 10-year overall survival of ~40%, and no reported association with TP53 or H3F3A mutations. A follow-up study found ATRX mutations in a series of cancers, including GBM, where ATRX (but not DAXX) mutations were identified in 3/21 pediatric GBMs (14%) and 8/122 adult GBMs (7%). To further evaluate the prevalence of ATRX and DAXX mutations in pediatric GBM, we performed immunostaining for these proteins on a well-characterized tissue microarray (TMA) with samples from 124 pediatric GBM patients. Lack of immunopositivity for ATRX was seen in 35% of cases (40/113 scored, 22 females and 18 males) and for DAXX in 6% (7/124 scored) (FIG. 3D, FIG. 2). Overall, 37% of samples had lost nuclear expression of either factor, corroborating our WES findings. Strikingly. ATRX-DAXX mutations (as assessed by direct sequencing or loss of protein expression) were found in 100% of G34-H3.3 mutant cases in the larger cohort of GBMs (13/13) where sufficient material was available ($p=1.4\times10^{-8}$, permutation test). The overlap of ATRX mutations with K27M-H3.3-mutated samples was not significant in either the exome data set (3/9 samples, p=0.58) or the full set of GBM screened (5/13, p=0.40) (FIG. 3E).

TABLE 6

Comparison of genes mutated in each of the 4 described adult GBM molecular subgroups (Verhaak et al. (Integrated genomic analysis identifies clinically relevant subtypes of glioblastoma characterized by abnormalities in PDGFRA, IDH1, EGFR, and NF1. Cancer Cell 17, 98-110) and in pediatric GBM shows that GBM in children has limited molecular overlap with adult GBM.

| | | Pediatric GBM | | adult GBM Gene-expression based molecular subtypes | | | | | | | | | | |
|---|---|---|---|---|---|---|---|---|---|---|---|---|---|---|
| | | | | Proneural | | | Neural | | | Classical | | | Mesenchymal | | |
| Pathway | Gene | No. of tumors | % | No. of tumors | % | p-value* | No. of tumors | % | p-value* | No. of tumors | % | p-value* | No. of tumors | % | p-value* |
| Chromatin Remodelling | H3F3A | 33/91 | 36 | NA | NA | NA | NA | NA | NA | NA | NA | NA | NA | NA | NA |
| | ATRX | 59/191 | 31 | NA | NA | NA | NA | NA | NA | NA | NA | NA | NA | NA | NA |
| | DAXX | 2/70 | 3 | NA | NA | NA | NA | NA | NA | NA | NA | NA | NA | NA | NA |
| | IDH1 | 8/84 | 10 | 11/37 | 30 | 0.0124 | 1/19 | 5 | 1 | 0/22 | 0 | 0.2006 | 0/38 | 0 | 0.0564 |
| Cell Signalling | EGFR | 2/49 | 4 | 6/37 | 16 | 0.0703 | 5/19 | 26 | 0.0155 | 7/22 | 32 | 0.0029 | 2/38 | 5 | 1 |
| | PDGFRA | 4/49 | 8 | 4/37 | 11 | 0.7208 | 0/19 | 0 | 0.5702 | 0/22 | 0 | 0.3033 | 0/38 | 0 | 0.1283 |
| | NF1 | 13/49 | 26 | 2/37 | 5 | 0.011 | 3/19 | 16 | 0.5261 | 1/22 | 5 | 0.0499 | 14/38 | 37 | 0.3542 |
| | PIK3CA | 3/49 | 6 | 3/37 | 8 | 1 | 1/19 | 5 | 1 | 1/22 | 5 | 1 | 1/38 | 3 | 0.6286 |
| | PIK3R1 | 5/49 | 10 | 7/37 | 19 | 0.3477 | 2/19 | 11 | 1 | 1/22 | 5 | 0.6583 | 0/38 | 0 | 0.0652 |
| | PTEN | 3/49 | 6 | 6/37 | 16 | 0.1646 | 4/19 | 21 | 0.0892 | 5/22 | 23 | 0.0971 | 12/38 | 32 | 0.0032 |
| Cell Cycle | TP53 | 27/49 | 55 | 20/37 | 54 | 1 | 4/19 | 21 | 0.0149 | 0/22 | 0 | <0.0001 | 12/38 | 32 | 0.0325 |
| | CDKN2A | 3/49 | 6 | NA | NA | NA | NA | NA | NA | NA | NA | NA | NA | NA | NA |
| | RB1 | 5/49 | 10 | 1/37 | 3 | 0.2302 | 1/19 | 5 | 1 | 0/22 | 0 | 0.3151 | 5/38 | 13 | 0.742 |

*Fisher's two tailed test to compare between pediatric GBM and different subtypes of adult GBM (Proneural, Neural, Classical, Mesenchymal). N/A = not available.

The histone code—post-translational modifications of specific histone residues—regulates virtually all processes that act on or depend on DNA, including replication and repair, regulation of gene expression, and maintenance of centromeres and telomeres. Accordingly, although recurrent histone mutations have not previously been reported in cancer, mutations in genes affecting histone post-translational modifications are increasingly described. H3.3 is a universal, replication-independent histone predominantly incorporated into transcription sites and telomeric regions, and associated with active and open chromatin. This role is conserved in the single histone H3 present in yeast, indicating its importance throughout evolution. It functions as a neutral replacement histone, but also participates in the epigenetic transmission of active chromatin states and is associated with chromatin assembly factors in large scale replication-independent chromatin remodeling events.

Figure 5A:
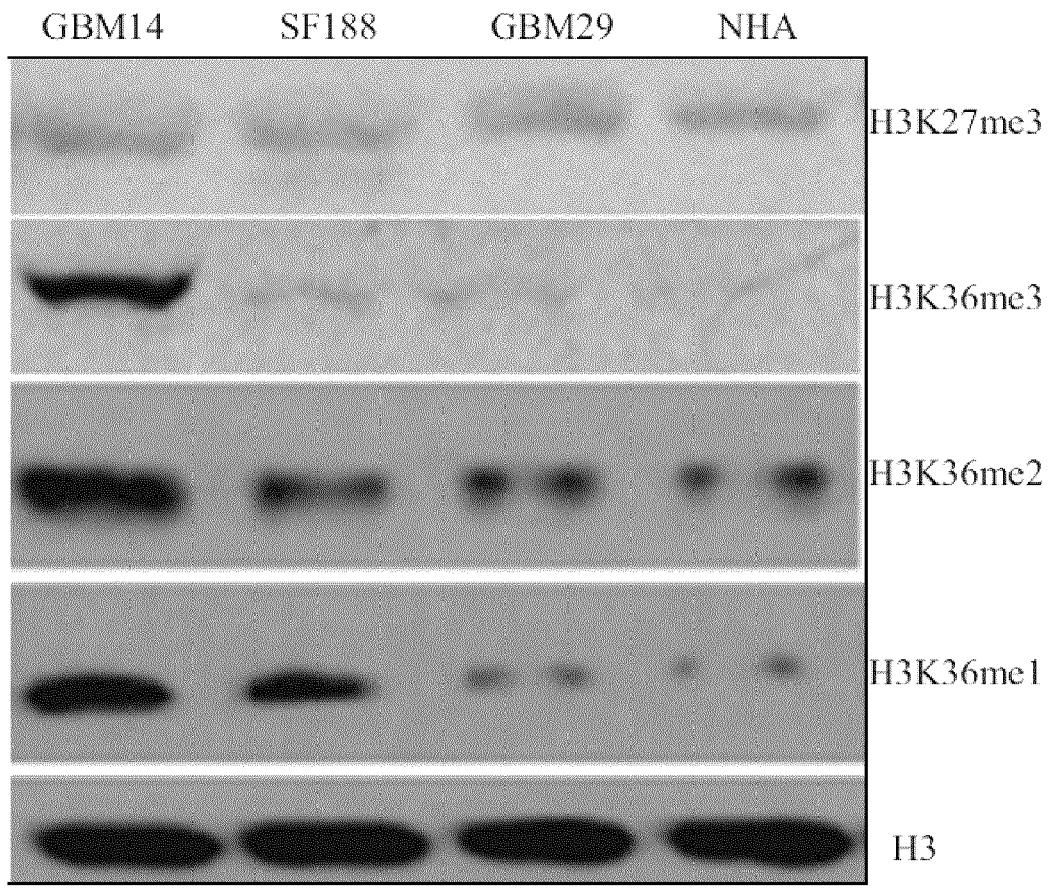
Figure 5B:
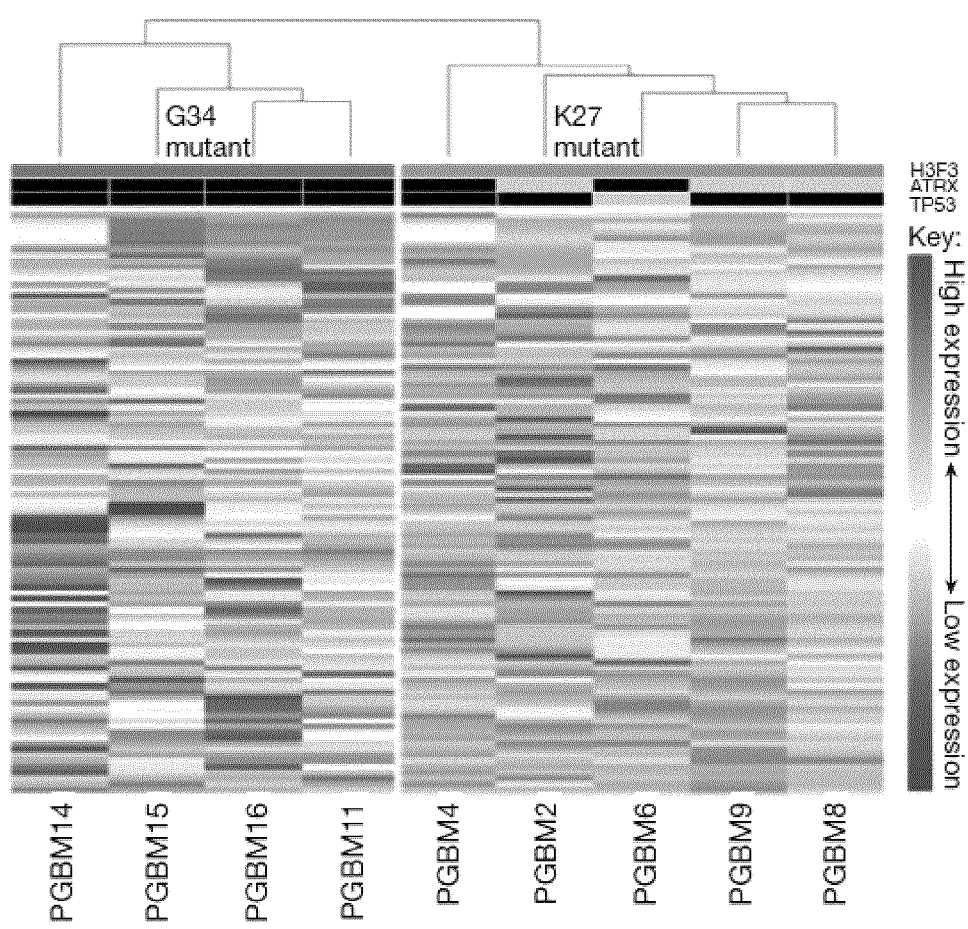
Figure 5C:
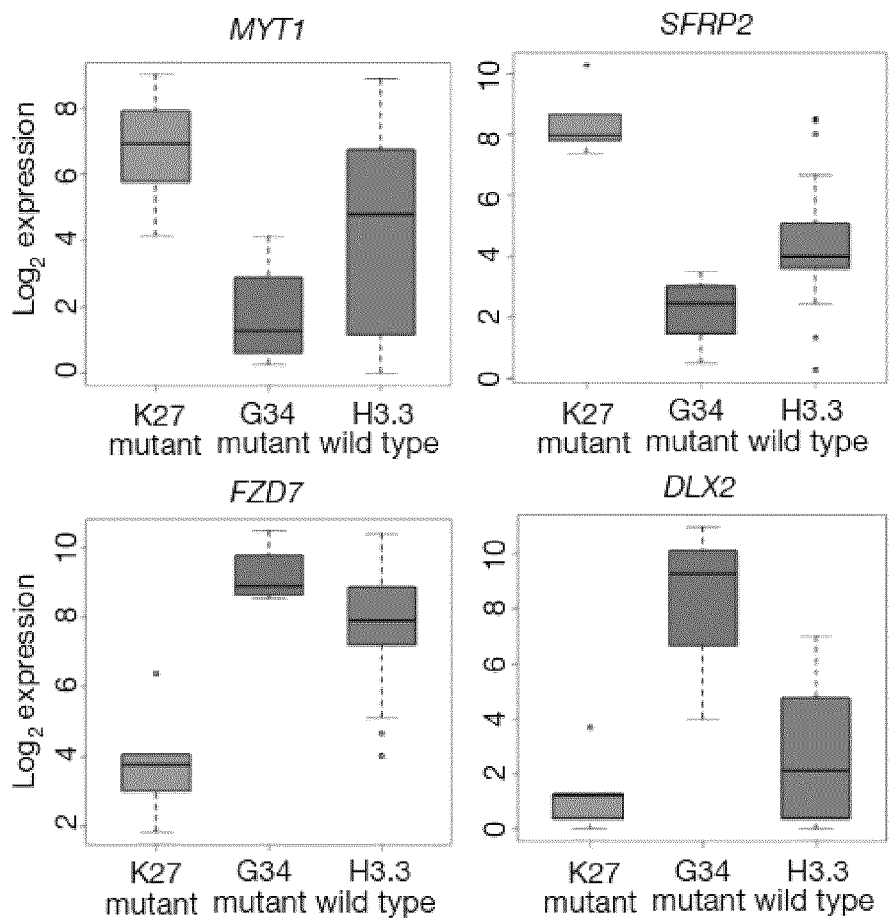

The non-random recurrence of the exact same mutation in different tumors, and the absence of truncating mutations, suggest that H3F3A mutations are most likely gain-of-function events. Lysine 27 is a critical residue of histone 3 and its variants, and methylation at this position (H3K27me) is commonly associated with transcriptional repression. In contrast, H3K36 methylation or acetylation typically promotes gene transcription. Without wishing to be bound to theory, the terminal $CH_3$ of methionine substituted at residue 27 likely mimics methylated H3K27, as the closest natural mimics to methylated lysine are leucine and methionine. Further, we also speculate that the positive charge and/or steric bulk of arginine or valine substituted for glycine 34 might prevent the recognition and subsequent removal of a lysine modification at K36. We identified increased levels of H3K36me3 in cells carrying the G34V-H3.3 mutation (PGBM14) compared to other cells, supporting this hypothesis (FIG. 5A). Thus, whilst their morphological phenotype is very similar (K27M and G34R/V mutant tumors are histologically indistinguishable), the two H3.3 variants are expected to act through a different set of genes. This indeed appears to be the case when looking at expression profiles of GBMs harbouring these two mutations. Unsupervised hierarchical clustering of gene expression from 27 of the WES cohort samples for which sufficient RNA was available revealed a clear separation in the expression of K27M versus G34R/V mutant samples (FIG. 6). Further analysis of just those samples harbouring an H3F3A mutation additionally showed a clear distinction in the expression pattern of these two variants (FIG. 5B, Table 7). Amongst these differentially expressed genes were several linked to brain development which showed a clear mutation-specific expression pattern when comparing both between K27 & G34 mutants and with H3.3 wild-type GBMs, including DLX2, SFRP2, FZD7 & MYT1 (FIG. 5C).

TABLE 7

Top 100 differentially expressed genes by standard deviation, used for
unsupervised hierarchical clustering, ordered as presented in FIG. 5B.

| | G34 Mutant | | | | K27 Mutant | | | | | | Mean(G34)- |
| | PGBM14 | PGBM15 | PGBM16 | PGBM11 | PGBM2 | PGBM4 | PGBM6 | PGBM8 | PGBM9 | SD | Mean(K27) |
|---|---|---|---|---|---|---|---|---|---|---|---|
| FOXG1 | 11.79 | 11.92 | 11.32 | 11.89 | 4.11 | 0.00 | 4.17 | 3.17 | 1.72 | 4.96 | 9.09 |
| SP8 | 5.47 | 9.88 | 7.95 | 9.13 | 0.00 | 0.68 | 0.00 | 2.07 | 0.00 | 4.20 | 7.56 |
| DLX6-AS1 | 2.72 | 10.83 | 10.20 | 9.38 | 0.00 | 2.70 | 2.29 | 0.00 | 0.00 | 4.58 | 7.28 |
| DLX2 | 4.03 | 10.96 | 9.26 | 9.25 | 1.26 | 3.69 | 1.20 | 0.38 | 0.00 | 4.28 | 7.07 |
| DLX1 | 5.07 | 11.45 | 10.02 | 9.88 | 2.74 | 4.87 | 0.68 | 2.51 | 0.93 | 4.12 | 6.76 |
| DLX6 | 3.74 | 10.05 | 9.02 | 7.35 | 1.32 | 1.58 | 2.23 | 0.85 | 0.00 | 3.80 | 6.35 |
| C14orf23 | 7.70 | 6.80 | 5.78 | 7.34 | 0.77 | 0.00 | 2.26 | 0.49 | 2.20 | 3.16 | 5.76 |
| DLX5 | 3.87 | 9.48 | 7.36 | 6.77 | 0.26 | 0.58 | 3.55 | 1.20 | 0.93 | 3.39 | 5.57 |
| FZD7 | 8.71 | 8.54 | 10.49 | 9.06 | 2.98 | 1.81 | 3.77 | 6.37 | 4.04 | 3.14 | 5.41 |
| PCK1 | 5.40 | 6.79 | 7.78 | 3.58 | 0.00 | 0.00 | 1.26 | 0.00 | 2.91 | 3.03 | 5.05 |
| NPY | 7.01 | 6.22 | 11.08 | 11.00 | 3.20 | 3.64 | 4.57 | 3.87 | 3.94 | 3.08 | 4.99 |
| MOXD1 | 5.62 | 6.93 | 10.28 | 10.20 | 6.64 | 3.36 | 1.26 | 4.53 | 4.49 | 2.98 | 4.20 |
| TRD@ | 8.31 | 4.15 | 6.92 | 10.72 | 1.38 | 4.89 | 1.89 | 5.04 | 3.83 | 2.99 | 4.12 |
| NEUROD1 | 3.32 | 8.05 | 3.05 | 9.67 | 0.00 | 3.49 | 1.26 | 3.41 | 4.91 | 3.05 | 3.41 |
| CES1 | 10.48 | 2.46 | 4.04 | 5.86 | 2.83 | 0.00 | 4.14 | 4.65 | 0.00 | 3.19 | 3.39 |
| LOC441179 | 1.38 | 8.96 | 5.35 | 8.56 | 3.04 | 0.26 | 3.79 | 2.32 | 4.41 | 2.99 | 3.30 |
| KIRREL3 | 0.85 | 5.77 | 7.36 | 8.79 | 0.68 | 3.68 | 1.26 | 2.56 | 4.69 | 2.93 | 3.12 |
| LOC100292909 | 4.04 | 7.45 | 9.93 | 5.33 | 0.00 | 4.17 | 1.38 | 6.41 | 6.58 | 3.05 | 2.98 |
| TFPI2 | 0.38 | 5.25 | 9.53 | 6.41 | 0.00 | 0.00 | 0.85 | 8.74 | 2.87 | 3.81 | 2.90 |
| LOC100192378 | 1.14 | 8.73 | 7.59 | 6.04 | 7.39 | 0.00 | 5.00 | 2.83 | 0.00 | 3.40 | 2.83 |
| HLA-DQA1 | 4.52 | 3.95 | 6.79 | 5.76 | 0.14 | 0.14 | 4.96 | 9.56 | 0.00 | 3.33 | 2.30 |
| HES5 | 2.89 | 9.44 | 8.08 | 6.58 | 1.07 | 8.77 | 2.00 | 5.55 | 5.86 | 3.02 | 2.09 |
| PLN | 0.58 | 10.65 | 4.64 | 7.78 | 4.03 | 0.00 | 3.83 | 6.28 | 5.30 | 3.32 | 2.03 |
| HLA-DQB1 | 0.93 | 3.98 | 5.51 | 5.79 | 0.58 | 0.26 | 0.93 | 8.58 | 0.26 | 3.07 | 1.93 |
| LOC100271840 | 3.83 | 6.14 | 2.94 | 8.37 | 1.96 | 1.14 | 0.68 | 5.57 | 8.06 | 2.88 | 1.84 |
| AQP9 | 9.75 | 1.54 | 0.58 | 3.96 | 1.58 | 2.07 | 3.02 | 6.13 | 1.68 | 2.91 | 1.06 |
| CXCL14 | 9.76 | 5.11 | 4.93 | 5.49 | 1.77 | 1.20 | 12.02 | 7.85 | 6.34 | 3.48 | 0.49 |
| OGDHL | 5.28 | 0.49 | 0.49 | 8.73 | 0.77 | 6.28 | 6.78 | 1.32 | 2.85 | 3.15 | 0.14 |
| SLC14A1 | 1.20 | 0.68 | 6.00 | 2.26 | 7.90 | 0.49 | 0.00 | 5.75 | 0.14 | 3.01 | −0.32 |
| CNGA3 | 0.00 | 1.43 | 6.83 | 5.15 | 8.57 | 0.00 | 1.14 | 3.35 | 6.10 | 3.17 | −0.48 |
| DDIT4L | 11.53 | 5.58 | 2.89 | 3.14 | 8.93 | 3.38 | 8.05 | 7.96 | 4.80 | 3.02 | −0.84 |
| COL6A2 | 4.22 | 4.24 | 4.43 | 0.00 | 0.26 | 0.58 | 8.39 | 6.61 | 5.35 | 2.95 | −1.02 |
| CHI3L1 | 13.30 | 4.92 | 7.45 | 9.87 | 8.21 | 8.10 | 13.68 | 12.75 | 7.74 | 3.05 | −1.21 |
| MET | 8.83 | 5.51 | 4.41 | 6.11 | 3.61 | 12.84 | 4.77 | 11.84 | 4.14 | 3.45 | −1.22 |
| ASCL1 | 1.20 | 11.78 | 10.24 | 9.84 | 11.13 | 9.68 | 7.69 | 8.75 | 10.35 | 3.15 | −1.25 |
| C8orf34 | 0.85 | 5.86 | 4.73 | 3.63 | 10.63 | 1.63 | 4.11 | 7.12 | 3.52 | 2.95 | −1.64 |
| SLC6A15 | 1.38 | 7.21 | 2.79 | 0.49 | 6.18 | 7.81 | 0.00 | 2.63 | 6.80 | 3.08 | −1.72 |
| CRABP1 | 0.85 | 4.82 | 0.49 | 1.20 | 0.00 | 4.46 | 1.07 | 4.93 | 8.57 | 2.89 | −1.97 |
| C1orf192 | 1.77 | 0.68 | 5.78 | 0.00 | 9.55 | 0.85 | 1.00 | 7.12 | 1.81 | 3.41 | −2.01 |
| IL8 | 6.79 | 5.48 | 5.28 | 4.15 | 2.63 | 3.29 | 10.42 | 11.62 | 9.20 | 3.21 | −2.01 |
| AKR1C1 | 12.64 | 3.91 | 4.78 | 4.50 | 9.00 | 9.68 | 5.31 | 9.40 | 9.05 | 3.03 | −2.03 |
| SLC39A12 | 0.93 | 2.96 | 3.83 | 4.12 | 8.75 | 0.38 | 6.07 | 7.77 | 2.20 | 2.91 | −2.07 |
| FSTL5 | 0.68 | 3.93 | 0.38 | 4.90 | 10.54 | 5.79 | 0.00 | 4.83 | 2.29 | 3.35 | −2.22 |
| LTF | 10.01 | 0.00 | 5.68 | 5.88 | 10.11 | 0.00 | 8.63 | 11.40 | 8.30 | 4.22 | −2.30 |
| NEFL | 4.12 | 5.89 | 0.58 | 1.72 | 3.91 | 10.69 | 1.63 | 7.85 | 2.89 | 3.27 | −2.31 |
| C2orf40 | 2.70 | 6.16 | 3.97 | 5.22 | 10.44 | 4.54 | 0.58 | 9.94 | 9.27 | 3.41 | −2.44 |
| CDH13 | 1.00 | 0.00 | 6.84 | 1.93 | 6.38 | 0.00 | 6.89 | 6.15 | 5.92 | 3.07 | −2.63 |
| C7orf57 | 2.74 | 0.00 | 3.00 | 0.00 | 9.32 | 1.43 | 0.00 | 6.90 | 2.98 | 3.25 | −2.69 |
| CCL20 | 6.00 | 0.77 | 1.49 | 0.00 | 1.81 | 0.77 | 7.35 | 8.71 | 5.38 | 3.28 | −2.74 |
| KCNA5 | 2.61 | 0.00 | 0.14 | 1.26 | 7.63 | 0.00 | 5.40 | 0.38 | 5.45 | 2.91 | −2.77 |
| GRIA2 | 7.99 | 1.72 | 9.15 | 10.53 | 10.14 | 11.82 | 10.06 | 9.04 | 9.80 | 2.90 | −2.82 |
| SERPINA3 | 11.80 | 1.00 | 9.61 | 9.56 | 12.19 | 7.09 | 13.37 | 11.61 | 9.99 | 3.71 | −2.86 |
| CDH19 | 0.00 | 1.96 | 5.28 | 7.79 | 9.32 | 5.22 | 7.31 | 5.76 | 5.66 | 2.87 | −2.90 |
| SLC44A5 | 0.00 | 9.04 | 5.74 | 8.13 | 8.92 | 8.93 | 7.99 | 7.96 | 9.93 | 3.01 | −3.02 |
| BCHE | 1.63 | 9.34 | 9.31 | 9.49 | 10.45 | 10.93 | 10.57 | 10.45 | 10.73 | 2.91 | −3.18 |
| LOC157503 | 0.00 | 4.22 | 0.00 | 6.86 | 8.43 | 7.50 | 3.52 | 4.99 | 5.51 | 3.01 | −3.22 |
| SCN7A | 0.00 | 3.07 | 2.87 | 7.23 | 8.69 | 2.41 | 8.44 | 6.54 | 6.71 | 3.07 | −3.27 |
| OTX2 | 0.00 | 5.19 | 2.49 | 0.00 | 8.92 | 0.00 | 8.56 | 6.81 | 1.68 | 3.70 | −3.27 |
| DPP10 | 3.10 | 10.40 | 2.74 | 2.23 | 8.04 | 8.03 | 7.10 | 7.95 | 8.36 | 2.95 | −3.28 |
| AKR1C2 | 12.37 | 1.20 | 2.29 | 2.04 | 8.07 | 9.35 | 3.64 | 9.28 | 8.41 | 4.03 | −3.28 |
| PAK7 | 0.00 | 6.65 | 3.05 | 2.26 | 7.67 | 8.49 | 3.12 | 5.31 | 6.94 | 2.86 | −3.31 |
| CALB1 | 7.79 | 0.00 | 1.14 | 2.61 | 3.32 | 7.24 | 6.17 | 7.92 | 6.57 | 3.02 | −3.36 |
| RALGAPA2 | 0.00 | 0.38 | 3.57 | 3.90 | 7.38 | 8.85 | 0.00 | 5.57 | 5.08 | 3.24 | −3.41 |
| STMN2 | 4.09 | 10.37 | 2.38 | 8.83 | 7.94 | 11.89 | 9.93 | 9.05 | 10.51 | 3.13 | −3.45 |
| DCC | 0.00 | 7.97 | 1.89 | 5.32 | 6.13 | 9.29 | 7.47 | 6.39 | 7.94 | 3.04 | −3.65 |
| GRIN2A | 2.89 | 0.77 | 2.41 | 0.68 | 9.86 | 1.54 | 4.00 | 5.29 | 6.17 | 2.99 | −3.69 |
| CTNNA2 | 1.26 | 9.33 | 6.22 | 4.86 | 11.04 | 8.95 | 8.03 | 8.75 | 8.92 | 2.94 | −3.72 |
| KLRC4 | 4.25 | 0.58 | 0.00 | 2.91 | 1.00 | 6.99 | 8.50 | 5.69 | 7.25 | 3.17 | −3.95 |
| PCDH7 | 2.00 | 7.03 | 2.32 | 10.51 | 10.94 | 8.51 | 8.87 | 9.09 | 9.70 | 3.32 | −3.96 |
| ALDH1A3 | 0.14 | 5.89 | 0.00 | 1.07 | 6.85 | 2.20 | 6.51 | 6.33 | 6.78 | 3.04 | −3.96 |
| RALYL | 0.93 | 5.21 | 3.90 | 2.32 | 8.76 | 8.21 | 2.77 | 7.45 | 8.43 | 2.99 | −4.04 |
| TTC9B | 0.68 | 2.85 | 0.68 | 0.85 | 1.07 | 7.62 | 6.68 | 4.89 | 6.42 | 2.89 | −4.07 |
| TMEFF2 | 0.85 | 8.22 | 3.58 | 5.65 | 8.61 | 9.90 | 7.58 | 7.85 | 9.37 | 2.96 | −4.08 |

TABLE 7-continued

Top 100 differentially expressed genes by standard deviation, used for unsupervised hierarchical clustering, ordered as presented in FIG. 5B.

| | G34 Mutant | | | | K27 Mutant | | | | | | Mean(G34)- |
|---|---|---|---|---|---|---|---|---|---|---|---|
| | PGBM14 | PGBM15 | PGBM16 | PGBM11 | PGBM2 | PGBM4 | PGBM6 | PGBM8 | PGBM9 | SD | Mean(K27) |
| INSM1 | 0.38 | 0.68 | 0.00 | 0.00 | 0.00 | 8.04 | 1.26 | 5.33 | 7.61 | 3.41 | −4.18 |
| UGT8 | 0.49 | 4.48 | 5.46 | 8.07 | 8.90 | 9.54 | 7.29 | 8.46 | 10.00 | 3.03 | −4.21 |
| RIT2 | 0.58 | 6.96 | 4.67 | 6.08 | 9.99 | 10.69 | 7.24 | 7.15 | 9.00 | 3.04 | −4.24 |
| OGN | 0.00 | 3.10 | 0.00 | 0.14 | 12.07 | 0.14 | 3.56 | 6.22 | 3.29 | 3.99 | −4.25 |
| H19 | 3.32 | 2.00 | 4.80 | 4.38 | 7.12 | 6.50 | 11.57 | 5.65 | 8.60 | 2.89 | −4.26 |
| NEGR1 | 0.00 | 8.91 | 1.81 | 7.28 | 10.16 | 9.38 | 7.69 | 8.15 | 8.46 | 3.52 | −4.27 |
| SHISA6 | 4.07 | 2.85 | 4.24 | 0.26 | 9.25 | 4.38 | 8.80 | 5.71 | 7.55 | 2.91 | −4.28 |
| KLRC3 | 4.94 | 0.14 | 2.70 | 4.41 | 4.55 | 8.46 | 7.81 | 7.09 | 8.83 | 2.89 | −4.30 |
| FAM19A5 | 0.00 | 2.54 | 7.12 | 4.71 | 8.87 | 8.64 | 8.25 | 6.31 | 9.57 | 3.23 | −4.74 |
| SLC7A2 | 5.08 | 0.14 | 1.93 | 0.38 | 7.67 | 5.77 | 5.45 | 7.69 | 6.82 | 2.98 | −4.80 |
| SUSD5 | 6.98 | 3.51 | 0.14 | 4.36 | 9.03 | 8.53 | 9.60 | 8.14 | 7.99 | 3.15 | −4.91 |
| ODZ2 | 2.58 | 6.04 | 1.20 | 4.12 | 8.22 | 7.21 | 10.37 | 7.23 | 9.07 | 3.05 | −4.93 |
| DLK1 | 6.85 | 5.16 | 0.00 | 2.43 | 6.68 | 3.92 | 11.63 | 9.52 | 11.05 | 3.93 | −4.95 |
| MYT1 | 1.63 | 4.14 | 0.93 | 0.26 | 4.15 | 9.02 | 6.90 | 5.78 | 7.93 | 3.14 | −5.02 |
| KCND2 | 2.72 | 5.26 | 2.20 | 6.52 | 9.36 | 9.93 | 8.35 | 8.46 | 9.99 | 2.99 | −5.04 |
| KCNJ9 | 0.77 | 3.70 | 0.93 | 0.00 | 8.38 | 7.11 | 7.67 | 2.83 | 6.00 | 3.23 | −5.05 |
| LHFPL3 | 6.18 | 4.49 | 3.49 | 7.94 | 11.34 | 10.58 | 10.26 | 9.37 | 11.40 | 2.99 | −5.07 |
| FAM5C | 5.73 | 2.35 | 0.26 | 5.26 | 8.02 | 9.32 | 8.23 | 8.06 | 9.05 | 3.16 | −5.14 |
| DBC1 | 1.63 | 2.10 | 1.96 | 3.29 | 9.49 | 7.00 | 10.00 | 6.35 | 6.28 | 3.23 | −5.57 |
| OPCML | 0.49 | 4.28 | 4.80 | 5.00 | 9.81 | 9.14 | 8.76 | 8.25 | 10.58 | 3.32 | −5.67 |
| CA10 | 3.51 | 2.20 | 2.14 | 2.04 | 6.50 | 8.97 | 8.03 | 8.05 | 9.60 | 3.18 | −5.76 |
| GPR17 | 1.07 | 2.93 | 0.00 | 0.00 | 6.49 | 5.31 | 5.19 | 8.68 | 8.63 | 3.43 | −5.86 |
| CADM2 | 1.43 | 4.88 | 0.26 | 5.59 | 9.30 | 9.03 | 9.14 | 8.26 | 9.30 | 3.54 | −5.97 |
| NXPH1 | 0.14 | 4.79 | 3.55 | 3.88 | 8.34 | 10.20 | 8.91 | 8.69 | 9.68 | 3.48 | −6.08 |
| SFRP2 | 3.49 | 2.51 | 2.38 | 0.49 | 10.24 | 7.76 | 7.35 | 7.95 | 8.62 | 3.44 | −6.17 |
| OLIG1 | 4.75 | 2.93 | 5.34 | 4.13 | 8.65 | 12.51 | 11.25 | 10.75 | 12.15 | 3.78 | −6.77 |
| MEGF11 | 0.00 | 0.85 | 1.43 | 2.49 | 8.21 | 7.80 | 8.33 | 7.09 | 10.24 | 3.91 | −7.14 |

Figure 5D:
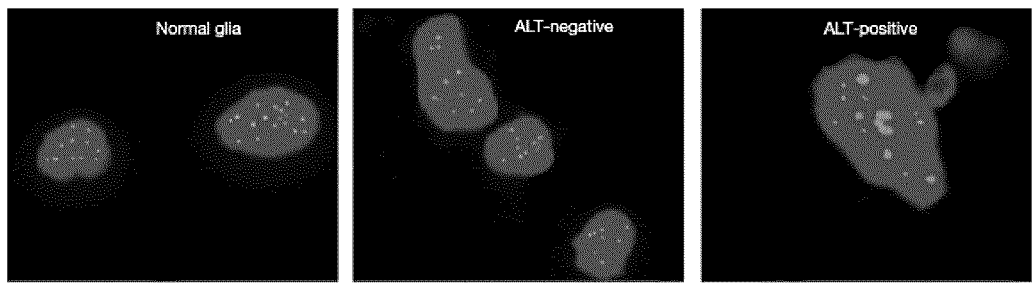
Figure 7A:
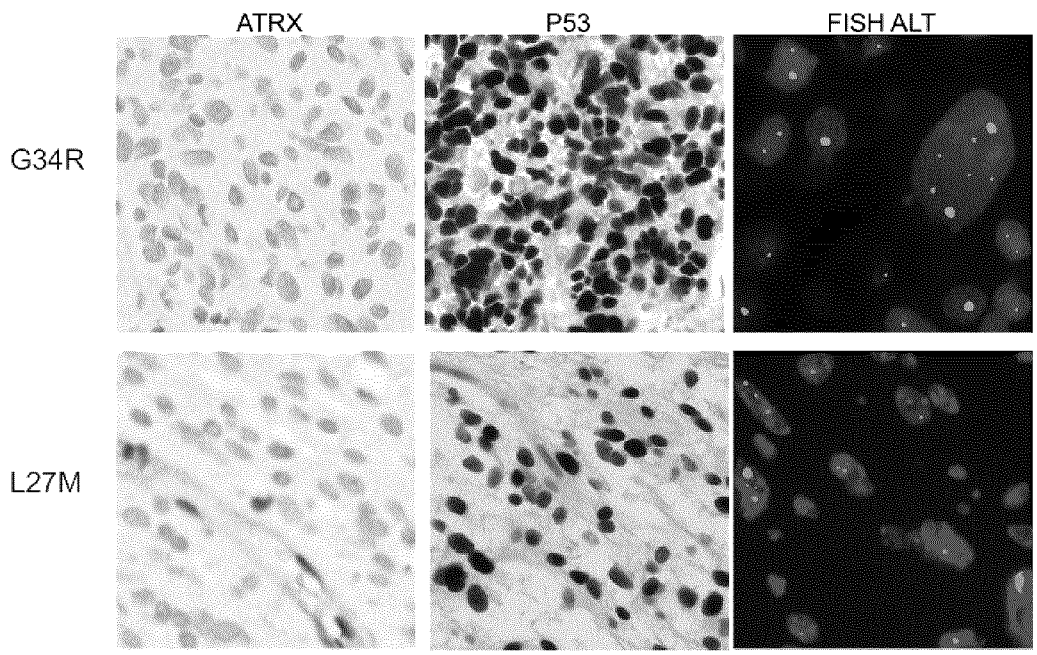
FIGS. 7A and 7B. (A) Overlap of TP53, ATRX and H3F3A mutations and ALT in tumor cells. Samples with H3F3A/ATRX/TP53 mutations determined by whole exome sequencing and for which fixed material was available were subjected to immunohistochemical staining for ATRX (left panels) and p53 (middle panels). Lack of ATRX expression was present across the vast majority of tumor cells. Aberrant p53 staining was present in more than 80% of cells lacking ATRX expression, both in K27M and G34R H3.3 mutant samples. This indicates that at least 30% of tumor cells have concomitant mutations in these three genes. Representative staining of two samples (GBM4 and GBM14) is shown. Telomere-specific fluorescence (left panels) in situ hybridization indicates the presence of ALT in tumors cells. (B) Overlap of absent DAXX and ATRX protein expression in tumor cells in a sample. Six samples showed concomitant lack of ATRX (right panels) and DAXX (left panels) expression following immunohistochemical staining of the pediatric GBM the tissue microarray (as well as FIG. 3D). These samples stained positively for other markers (GFAP) showing that lack of staining was not due to tissue processing (data not shown).
Figure 7B:
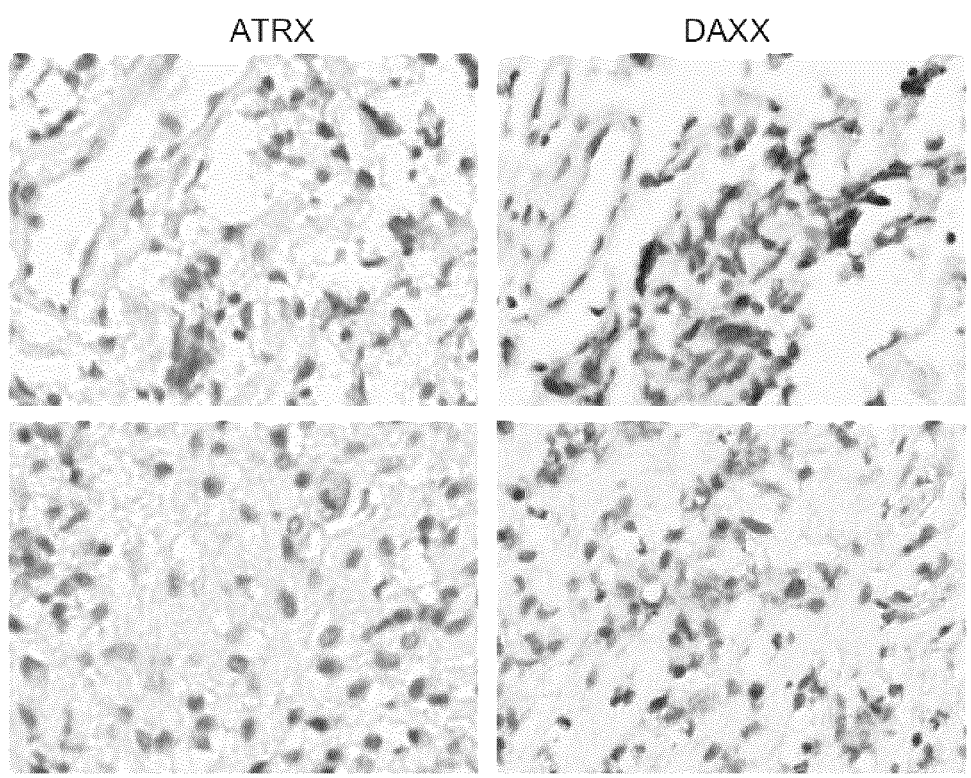
Figure 8:
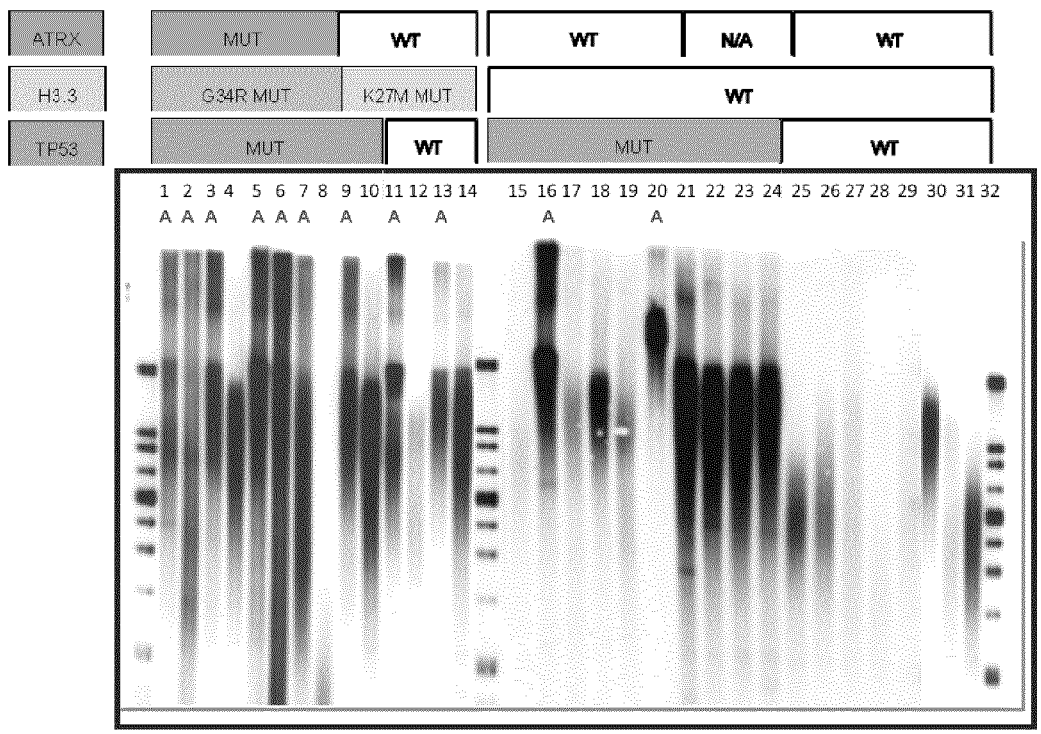
FIG. 8. Alternative Lengthening of Telomeres (ALT) is associated with ATRX/H3F3/TP53 mutations. Previous groups have shown measurement of telomerase expression or activity not to be reliable to assess ALT. We assessed ALT using two surrogate markers: telomere-specific fluorescence in situ hybridization (FIG. 5D and FIG. 7). In this figure, telomere-specific Southern blotting of high molecular weight genomic DNA is shown for various samples. Telomere Restriction Length (TRF) assay was used to assess the presence of ALT in 32 pediatric GBM. Tumors were blotted according to their TP53 mutations (green), H3F3A mutations (Yellow) and ATRX mutations (blue). Tumors demonstrating ALT are marked as A in red. ALT tumors demonstrate abnormally long telomeres (>21 kb in length) which are not seen in telomerase positive tumors or normal tissues. Most ALT tumors had concomitant TP53 mutations and there was significant enrichment for ALT among ATRX/H3F3 mutant tumors (p=0.003). Overall ALT tumors were strongly associated with ATRX/H3F3/TP53 mutations (p=0.0002. Fisher's exact test). These data suggest that TP53 mutations are typically necessary but require additional alterations in chromatin modulating genes for ALT formation.

ATRX loss, frequently observed in this study, has recently been shown to be associated with alternative lengthening of telomeres (ALT) in PanNETs and GBMs. We performed telomere-specific fluorescence in situ hybridization (FISH) on the samples with K27M or G34R/V mutations identified by WES for which we had slides available (FIG. 7) and on the pediatric GBM TMA (FIG. 5D). These experiments showed that ALT is strongly correlated with ATRX loss (37/47 samples with ALT showed ATRX loss, p<0.001). However, some samples with nuclear ATRX staining still showed ALT, indicating that additional defects may also account for elongated telomeres in GBM. Hence, we compared telomere length in 14 pediatric GBM samples carrying mutations in ATRX, and/or H3F3A with 18 samples having no mutations in these genes by telomere restriction fragment length (TRF) analysis (FIG. 5E, FIG. 8). The presence of ALT was best explained by the simultaneous presence of ATRX/H3F3A/TP53 mutations (p=0.0002. Fisher's exact test). Tumors without ATRX/H3F3A/TP53 mutations almost invariably showed shorter telomeres than are observed with ALT, as seen in telomerase-positive gliomas.

Figure 9:
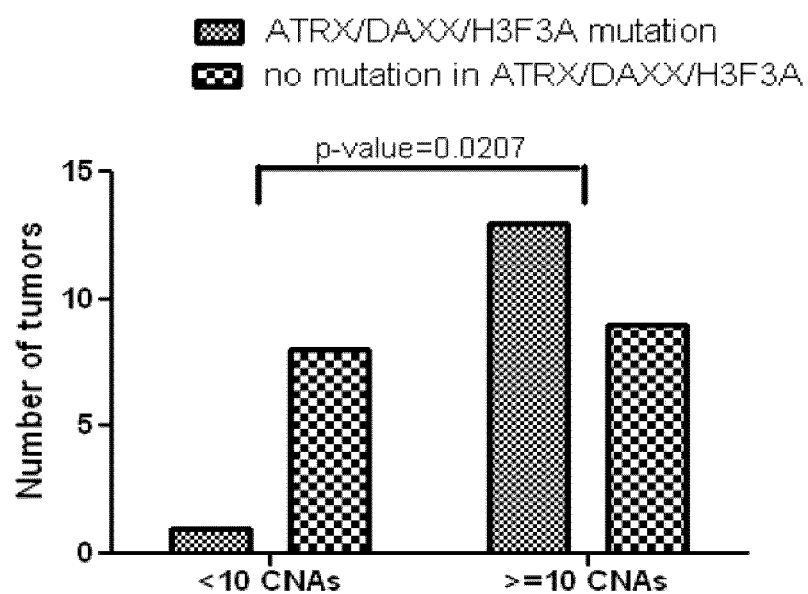
FIG. 9. Single nucleotide polymorphism (SNP) array profiling reveals differences in copy number aberrations (CNAs) in ATRX/DAXX/H3F3A-mutated pediatric glioblastoma. Focal losses or gains comprising genes relevant in pediatric GBM overlapped with previous reports. Samples were spilt into a group with relatively stable genomes (<10 CNAs) and a group with more unstable genomes (=10 CNAs). Results are shown as the number of tumors in function of genome stability and mutations at ATRX, DAXX and H3F3A. Samples with a mutation in at least one of ATRX, TP53 and H3F3A were significantly associated with an unstable genome (p=0.0207. Fisher's exact test).
Figures 10A, 10B:
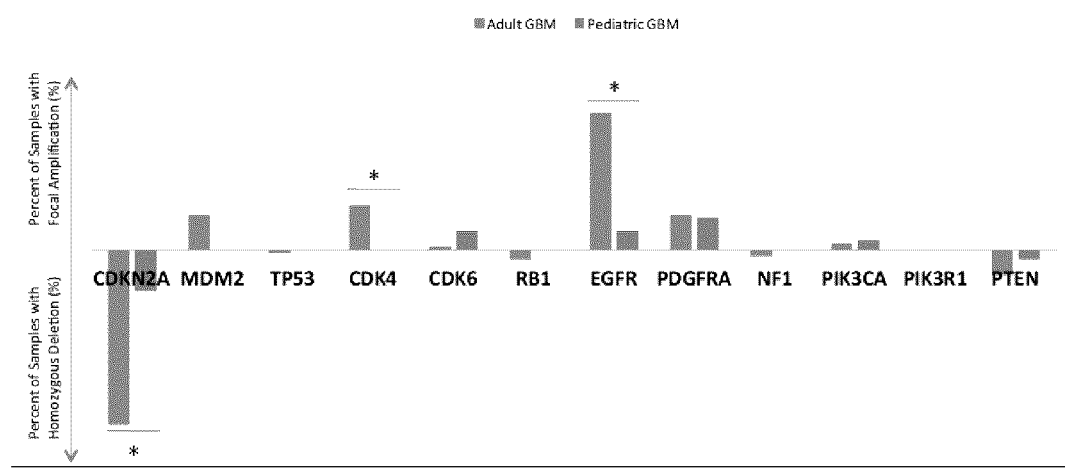
FIGS. 10A and 10B. Comparison of the most frequent focal amplification and deletion in genes involved in glioblastoma shows major differences between adult GBM and pediatric GBM. (A) Results are shown as percent of samples with focal amplification (upward arrow) or percent of samples with homozygous deletions (downward arrow) for the CDKN2A, MDM2, TP53, CDK4, CDK6, RB1, EGFR, PDGFRA, NF1, PIK3Ca, PIK3R1 or the PTEN genes for adult GBM samples (left bar) and pediatric GBM (right bar). * indicates statistical significance. (B) Table associated with FIG. 10A listing, for each gene, the type of mutation (DEL=deletion, AMP=amplification), the number of adult GBM samples bearing the mutation in function of the total number of samples of adult GBM (#aGBM/n), the percentage of adult GBM bearing the mutation (% aGBM), the number of pediatric GBM samples bearing the mutation in function of the total number of samples of pediatric GBM (#pGBM/n), the percentage of pediatric GBM bearing the mutation (% pGBM) and the p-value associated with the comparison between adult and pediatric GBM (p-value).

Genetic stability was also assessed through evaluating DNA copy number aberrations (CNAs) in 31 of the 48 tumors using Illumina SNP arrays containing ~2.5 million oligonucleotides (Table 1). We identified a total of 254 alterations, including 119 high-level focal amplifications and 22 homozygous deletions (Tables 8 and 9). Loss of heterozygosity (whole chromosome changes, broad and focal heterozygous deletions, Table 9) was common in pediatric GBM samples, as we have previously reported. The focal gains and losses we identified in our study, as wee as genes most frequently affected by these CNAs, showed a high degree of overlap with other published pediatric datasets. The number of CNAs per tumor was higher in samples with H3F3A/ATRX-DAXX/TP53 mutations (FIG. 9).

Tables 8 and 9 present the single nucleotide polymorphism (SNP) array profiling which reveals differences in copy number aberrations (CNAs) in ATRX/DAXX/H3F3A-mutated pediatric glioblastoma. Thirty one pediatric GBM DNA samples were analyzed using the Illumina HUMAN OMNI2.5™ SNP array and visualized with Illumina GENOMESTUDIO™ software. Copy number aberrations (CNAs) were quantified visually as previously described (Paugh, B. S. et al. Integrated molecular genetic profiling of pediatric high-grade gliomas reveals key differences with the adult disease. J Clin Oncol 28, 3061-3068; Maher. E. A. et al. Marked genomic differences characterize primary and secondary glioblastoma subtypes and identify two distinct molecular and clinical secondary glioblastoma entities. Cancer Res 66, 11502-11513 (2006); Iwase, S. et al. ATRX ADD domain links an a typical histone methylation recognition mechanism to human mental-retardation syndrome. Nat Struct Mol Biol 18, 769-776). CNAs were further subcategorized into whole chromosome, broad or focal areas of gain, homozygous deletion and loss of heterozygosity (LOH). The number of CNAs of all types was counted for each sample and associated with its H3F3A, ATRX, DAXX and TP53 mutation status. The average number of CNAs per sample was 24.5 (an average of 8.2 gains and 16.3 losses).

Recurrent point mutations in IDH1 (mainly R132H) are gain of function mutations commonly identified in secondary GBM and the lower-grade tumors from which they develop (86-98% of these astrocytomas), and typically occur in younger adults. Strikingly, IDH1 and H3F3A mutations were mutually exclusive in our sequencing cohort (p=1.6× $10^{-4}$). Neomorphic enzyme activity resulting from IDH1 mutation leads to the production of high quantities of the onco-metabolite 2-hydroxyglutarate (2-HG). Without wishing to be bound to theory, it is speculated that the increased 2-HG inhibits histone demethylase, specifically inducing increased methylation of both H3K27 and H3K36, the two residues affected directly (K27) or indirectly (K36) by the mutations in H3F3A uncovered in this study. Furthermore, overlap of H3F3A and TP53 mutations in children with GBM (all of the G34R/V and 82% of K27M mutants also harbour TP53 mutations) mirrors the large overlap of IDH1 mutations with TP53 mutations in the proneural adult GBM sub-group. Thus, mutations which directly (H3F3A), or indirectly (IDH1) affect the methylation of H3.3 K27 or H3.3 K36, in combination with TP53 mutations, characterize the pathogenesis of pediatric and young adult GBM.

Our data indicate a central role of H3.3/ATRX-DAXX perturbation in pediatric GBM. The main chaperone protein for loading of H3.3 at active and repressed genes and at transcription factor binding sites is HIRA44, while the ATRX-DAXX complex mediates H3.3 deposition at telomeres and near specific active genes. Assuming that HIRA-dependent recruitment of H3.3 is preserved (mutations in HIRA were not identified in our dataset), mutant H3.3 recruitment would occur at locations across the chromosome and induce specific patterns of chromatin remodelling to yield distinct gene expression profiles. Additional loss of ATRX may act to reduce H3.3 incorporation at a subset of genes important in oncogenesis, preventing mutant H3.3 from altering their transcription. ATRX loss will also impair H3.3 loading at telomeres and disrupt their heterochromatic state, which in turn will lead to telomere destabilization and increased homologous recombination, facilitating alternative lengthening of telomeres (ALT), aneuploidy, or chromosome mis-segregation. ALT allows escape from senescence and promotes survival of ATRX-DAXX mutant cells, while the added loss of p53 function, also a common finding in the present study, will prevent apoptosis (as ATRX or DAXX deficiency otherwise leads to p53-dependent apoptosis), and seems to further promote ALT as identified herein. We suggest that the combined effects of these mutations would thus have profound effects on chromatin remodeling.

TABLE 8

Numbers of CNAs of each type identified in each tumour sample analyzed.

| | GAINS | | | | DELETIONS | | | LOH | |
| ID | Whole Chr. | Broad | Focal | Total Gains | Whole Chr. | Broad | Focal | Total Deletions | Whole Chr. | Broad |
| --- | --- | --- | --- | --- | --- | --- | --- | --- | --- | --- |
| PGBM1 | 0 | 2 | 2 | 4 | 0 | 0 | 0 | 0 | 1 | 3 |
| PGBM2 | 3 | 1 | 2 | 6 | 0 | 0 | 0 | 0 | 4 | 10 |
| PGBM3 | 2 | 10 | 7 | 19 | 0 | 0 | 0 | 0 | 3 | 22 |
| PGBM4 | 0 | 15 | 9 | 24 | 0 | 0 | 0 | 0 | 4 | 17 |
| PGBM5 | 0 | 4 | 0 | 4 | 0 | 0 | 0 | 0 | 2 | 19 |
| PGBM6 | 0 | 3 | 1 | 4 | 0 | 0 | 0 | 0 | 0 | 5 |
| PGBM11 | 0 | 7 | 11 | 18 | 0 | 0 | 2 | 2 | 0 | 16 |
| PGBM12 | 1 | 2 | 0 | 3 | 0 | 0 | 3 | 3 | 1 | 22 |
| PGBM13 | 1 | 2 | 1 | 4 | 0 | 0 | 0 | 0 | 1 | 4 |
| PGBM14 | 0 | 3 | 1 | 4 | 0 | 0 | 0 | 0 | 11 | 10 |
| PGBM18 | 0 | 2 | 1 | 3 | 0 | 0 | 0 | 0 | 1 | 3 |
| PGBM19 | 1 | 0 | 0 | 1 | 0 | 0 | 0 | 0 | 17 | 3 |
| PGBM20 | 1 | 5 | 4 | 10 | 0 | 0 | 0 | 0 | 1 | 23 |
| PGBM21 | 0 | 4 | 3 | 7 | 0 | 0 | 0 | 0 | 13 | 7 |
| PGBM23 | 0 | 1 | 0 | 1 | 0 | 0 | 0 | 0 | 0 | 3 |
| PGBM24 | 0 | 10 | 1 | 11 | 0 | 0 | 2 | 2 | 8 | 15 |
| PGBM25 | 0 | 6 | 11 | 17 | 0 | 1 | 4 | 5 | 11 | 14 |
| PGBM26 | 2 | 4 | 11 | 17 | 0 | 0 | 0 | 0 | 8 | 5 |
| PGBM27 | 3 | 5 | 14 | 22 | 0 | 1 | 0 | 1 | 9 | 14 |
| PGBM31 | 0 | 7 | 5 | 12 | 0 | 0 | 0 | 0 | 1 | 3 |
| PGBM32 | 0 | 2 | 2 | 4 | 0 | 0 | 0 | 0 | 0 | 2 |
| PGBM34 | 3 | 11 | 8 | 22 | 0 | 1 | 1 | 2 | 4 | 18 |
| PGBM35 | 0 | 1 | 1 | 2 | 0 | 0 | 0 | 0 | 3 | 1 |
| PGBM36 | 0 | 0 | 2 | 2 | 0 | 0 | 0 | 0 | 0 | 1 |
| PGBM37 | 0 | 1 | 0 | 1 | 0 | 0 | 0 | 0 | 0 | 5 |
| PGBM39 | 3 | 1 | 0 | 4 | 0 | 0 | 3 | 3 | 3 | 2 |
| PGBM40 | 0 | 0 | 0 | 0 | 0 | 0 | 0 | 0 | 0 | 0 |
| PGBM41 | 0 | 0 | 0 | 0 | 0 | 0 | 0 | 0 | 0 | 0 |
| PGBM42 | 0 | 0 | 0 | 0 | 0 | 0 | 0 | 0 | 0 | 1 |
| PGBM43 | 0 | 5 | 16 | 21 | 0 | 0 | 4 | 4 | 5 | 18 |
| PGBM45 | 0 | 1 | 6 | 7 | 0 | 0 | 0 | 0 | 0 | 1 |
| Totals | 20 | 115 | 119 | 254 | 0 | 3 | 19 | 22 | 111 | 267 |
| Mean | 0.65 | 3.71 | 3.84 | 8.19 | 0.00 | 0.10 | 0.61 | 0.71 | 3.58 | 8.61 |

| | LOH | | | CNA Grouping | H3F3A | ATRX | DAXX |
| ID | Focal | Total LOH | Total Losses | Total CNAs | Group 1/2 | Mut Y/N | Mut Y/N | Mut Y/N |
| --- | --- | --- | --- | --- | --- | --- | --- | --- |
| PGBM1 | 2 | 6 | 6 | 10 | 2 | Y | Y | N |
| PGBM2 | 2 | 16 | 16 | 22 | 2 | Y | N | N |
| PGBM3 | 5 | 30 | 30 | 49 | 2 | Y | N | N |
| PGBM4 | 3 | 24 | 24 | 48 | 2 | Y | Y | N |
| PGBM5 | 4 | 25 | 25 | 29 | 2 | Y | N | N |
| PGBM6 | 6 | 11 | 11 | 15 | 2 | Y | Y | N |
| PGBM11 | 2 | 18 | 20 | 38 | 2 | Y | Y | N |

TABLE 8-continued

Numbers of CNAs of each type identified in each tumour sample analyzed.

| | | | | | | | | |
|---|---|---|---|---|---|---|---|---|
| PGBM12 | 8 | 31 | 34 | 37 | 2 | Y | Y | N |
| PGBM13 | 1 | 6 | 6 | 10 | 2 | Y | Y | N |
| PGBM14 | 1 | 22 | 22 | 26 | 2 | Y | Y | N |
| PGBM18 | 2 | 6 | 6 | 9 | 1 | N | Y | N |
| PGBM19 | 0 | 20 | 20 | 21 | 2 | N | Y | Y |
| PGBM20 | 17 | 41 | 41 | 51 | 2 | N | Y | N |
| PGBM21 | 1 | 21 | 21 | 28 | 2 | N | N | Y |
| PGBM23 | 0 | 3 | 3 | 4 | 1 | N | N | N |
| PGBM24 | 3 | 26 | 28 | 39 | 2 | N | N | N |
| PGBM25 | 3 | 28 | 33 | 50 | 2 | N | N | N |
| PGBM26 | 3 | 16 | 16 | 33 | 2 | N | N | N |
| PGBM27 | 5 | 28 | 29 | 51 | 2 | N | N | N |
| PGBM31 | 0 | 4 | 4 | 16 | 2 | N | N | N |
| PGBM32 | 3 | 5 | 5 | 9 | 1 | N | N | N |
| PGBM34 | 2 | 24 | 26 | 48 | 2 | N | N | N |
| PGBM35 | 0 | 4 | 4 | 6 | 1 | N | N | N |
| PGBM36 | 2 | 3 | 3 | 5 | 1 | N | N | N |
| PGBM37 | 2 | 7 | 7 | 8 | 1 | N | N | N |
| PGBM39 | 12 | 17 | 20 | 24 | 2 | N | N | N |
| PGBM40 | 0 | 0 | 0 | 0 | 1 | N | N | N |
| PGBM41 | 1 | 1 | 1 | 1 | 1 | N | N | N |
| PGBM42 | 0 | 1 | 1 | 1 | 1 | N | N | N |
| PGBM43 | 9 | 32 | 36 | 57 | 2 | N | N | N |
| PGBM45 | 6 | 7 | 7 | 14 | 2 | N | N | N |
| Totals | 105 | 483 | 505 | 759 | | | | |
| Mean | 3.39 | 15.58 | 16.29 | 24.48 | | | | |

TABLE 9

CNA regions identified in each tumour sample analyzed.

| Sample | GAINS Whole Chr | GAINS Broad | GAINS Focal | DELETIONS Whole Chr | DELETIONS Broad | DELETIONS Focal | LOH Broad | LOH Focal |
|---|---|---|---|---|---|---|---|---|
| PGBM1 | | 11q13.1-11q25<br>17p13.2-17p13.3 | 11q22.3<br>18q23 | 16 | 10q21.3-10q26.3<br>15q<br>Xp21.2-Xp22.33 | | | 11q14.1<br>15q26.3 |
| PGBM2 | 4<br>8<br>19 | 10q25.3-10q26.3 | 5p14.3-5p12<br>13q34 | 3<br>7<br>9<br>18 | 5q<br>5p15.2-5p14.3<br>10p<br>10q<br>12q24.31-12q24.33<br>13q14.11-13q34<br>14q<br>17p13.1-17p13.3<br>21q<br>22q | | | 5p15.31<br>5p15.33 |
| PGBM3 | 7<br>X | 1q<br>9p<br>14q11.2-14q24.2<br>14q24.3-14q31.3<br>16p<br>18p<br>20p12.3-20p13<br>21q<br>12q15-12p13.33<br>11p12-11p11.2 | 1q31.2-1q31.3<br>5q21.1<br>6p24.3<br>6p12.1-6p11.2<br>17q21.31<br>17q11.2<br>11p14.1-11p13 | 4<br>8<br>10 | 1p<br>2p14-2q37.3<br>3p<br>5q11.2-5q21.3<br>5q22.2-5q23.2<br>5q23.2-5q31.1<br>5q31.1-5q32<br>5q35.1-5q35.3<br>7q31.31-7q32.1<br>8q11.1-8q12.1<br>8q13.2-8q21.13<br>9q<br>11p14.1-11p15.5<br>11p11.2<br>12q15-12q24.33<br>12p13.31-12p12.3<br>12q12-12q13.13<br>13q<br>14q31.3-14q32.33<br>17q21.33-17p13.3<br>17q21.33-17q25.3<br>22q | | | 5q31.3<br>5q33.1-5q34<br>14q24.3<br>17q11.2<br>11q14.1 |
| PGBM4 | | 1p13.3-1q44<br>2p15-2p25.3<br>3q25.33-3q29<br>3q26.32-3q29<br>4q25-4q26<br>4q26-4q28.2<br>4q31.3-4q32.1<br>4q32.1-4q32.3<br>10q23.31-10q23.33<br>12q12-12q13.13 | 4q12<br>4q31.21<br>4q31.23<br>4q34.1<br>7q31.2<br>8q24.21<br>10q26.13<br>10q26.2<br>20p13 | 9<br>11<br>16<br>20 | 3q11.2-3q25.33<br>4q12-4q25<br>4q32.3-4q35.2<br>5q21.1-5q35.3<br>6q13-6q27<br>7p21.3-7p21.1<br>7p21.1-7p11.2<br>7q35.1-7q36.3<br>8p12-8p23.3<br>8q | | | 7p22.1-7p22.3<br>7q31.2-7q31.31<br>8p11.22-8p11.21 |

TABLE 9-continued

CNA regions identified in each tumour sample analyzed.

| Sample | GAINS Whole Chr | GAINS Broad | GAINS Focal | DELETIONS Whole Chr | DELETIONS Broad | DELETIONS Focal | LOH Whole Chr | LOH Broad | LOH Focal |
|---|---|---|---|---|---|---|---|---|---|
| | | 12q23.3-12q24.31<br>14q11.2<br>14q21.1-14q21.2<br>14q21.2-14q21.3<br>16q11.2-16q23.1 | | | 10q21.2-10q22.3<br>12p<br>12q<br>13q<br>14q<br>17p<br>22q | | | | |
| PGBM5 | | 15q11.2-15q14<br>15q25.1-15q26.3<br>17q21.32-17q25.3<br>19p13.11-19p12 | | 1<br>6 | 2p<br>2q11.2-2q12.3<br>2q31.1-2q34<br>2q34-2q37.3<br>3p21.31-3p26.3<br>5q<br>9p21.2-9p24.3<br>10p14-10p15.3<br>10p12.1-10q26.3<br>11p<br>12q13.11-12q24.33<br>14q23.3-14q32.33<br>15q15.1-15q22.2<br>16q<br>17p<br>17q11.2-17q21.32<br>19q<br>21q11.2-21q21.1<br>21q21.2-21q21.3 | | | | 13q31.1<br>13q31.3<br>13q32.1-13q32.2<br>17q11.2 |
| PGBM6 | | 1q<br>9p23-9p21.1<br>9q31.1-9q34.3 | 10q22.3 | | 1p31.1-1p11.2<br>9p23-9p24.3<br>9p21.1-9q31.1<br>10q23.31-10q25.1<br>19q | | | | 4q26-4q27<br>10q23.1<br>10q23.1<br>10q23.1<br>10q22.3 |
| PGBM11 | | 2p24.2-2p25.3<br>2q24.2-2q37.3<br>5p15.2-5p15.33<br>5q13.2-5q31.3<br>7p21.1-7p21.3<br>10p12.31-10p15.3<br>17q24.2-17q25.3 | 5q31.3<br>7p21.3<br>7p22.2<br>7p22.3<br>7p22.3<br>9p21.3<br>10q22.3<br>10p11.22-10p11.21<br>16q21-16q22.1<br>20p13<br>Xp11.22-Xp11.21 | | 1q31.1-1q44<br>1q24.2-1q21.1<br>9p22.1-9p24.3<br>9p21.3-9p21.2<br>10q23.31-10q26.3<br>10q21.1-10q23.1<br>11p<br>12q<br>13q<br>16p11.2-16q24.3<br>17p11.2-17p13.3<br>18q11.2-18q12.2<br>18q12.2-18q23<br>20p<br>20q | 10q23.31<br>Xp11.3 | | | 2q22.2-2q22.1<br>5q13.1 |

TABLE 9-continued

CNA regions identified in each tumour sample analyzed.

| Sample | GAINS | | | DELETIONS | | | LOH | | |
|---|---|---|---|---|---|---|---|---|---|
| | Whole Chr | Broad | Focal | Whole Chr | Broad | Focal | Whole Chr | Broad | Focal |
| PGBM12 | 7 | 3q26.31-3q29<br>22q13.2-22p13.33 | | 8 | 21q<br>1q23.2-1q43<br>2p<br>3q12.1-3q26.1<br>3q26.1-3q26.31<br>4q<br>8p21.1-8p12<br>8p11.22-8p11.21<br>9p24.1-9p24.3<br>9p24.1-9p13.1<br>9q31.1-9q21.11<br>9q31.1-9q33.2<br>9q33.2-9q34.3<br>10p<br>10q11.21-10q25.1<br>10q25.1-10q26.3<br>14q<br>14q31.3-14q32.31<br>15q<br>16p<br>18q21.2-18q23<br>19p13.11-19p13.3<br>19q13.32-19q13.43 | 4q31.23<br>10q22.1<br>17p13.3 | 8 | | 5q34<br>11q14.1<br>11q22.1<br>11q22.1<br>11q22.1-11q24.3<br>15q26.3<br>16q24.3<br>18q23 |
| PGBM13 | 20 | 1q<br>12p12.3-12p13.33 | 5q13.2-5q13.3 | | 3p12.1-3q26.1<br>4p15.31-4p16.3<br>4p15.31-4q35.2<br>11q24.3-11q25 | | 17 | | 6q12 |
| PGBM14 | | 4p15.33-4q13.1<br>4q26-4q35.2<br>17q12-17q25.3 | 4q32.1-4q32.3 | | 3q<br>4q13.1-4q26<br>9p<br>9q<br>13q<br>14q<br>15q<br>19q13.42-19q13.43<br>21q<br>22q | | 2<br>6<br>7<br>8<br>10<br>11<br>12<br>16<br>18<br>19<br>20 | | 18q23 |
| PGBM18 | | 1q<br>9q | 13q13.3 | | 3q27.2-3q29<br>9p<br>22q12.1-22q13.33 | | 10 | | |
| PGBM19 | X | | | | 13q<br>14q<br>15q | | 1<br>2<br>3<br>4<br>5<br>6 | | 8p23.2-8p23.3<br>12q24.33 |

TABLE 9-continued

CNA regions identified in each tumour sample analyzed.

| Sample | GAINS Whole Chr | GAINS Broad | GAINS Focal | DELETIONS Whole Chr | DELETIONS Broad | DELETIONS Focal | LOH Whole Chr | LOH Broad | LOH Focal |
|---|---|---|---|---|---|---|---|---|---|
| PGBM20 | 19 | 10p12.2-10p15.3<br>15q25.1-15q26.3<br>16p13.12-16p13.3<br>18p11.31-18p11.21<br>20p13-20q11.23 | 2p24.3-2p24.2<br>2q14.2<br>2q14.3<br>15q23 | 8<br>9<br>10<br>11<br>12<br>16<br>17<br>19<br>20<br>21<br>22 | | | 9 | 1p<br>3q11.2-3q28<br>5q31.1-5q34<br>5q35.2-5q35.3<br>6p22.3-6p21.32<br>6q12-6q13<br>6q13-6q14.1<br>6q23.3-6q24.2<br>8p23.1-8p23.3<br>10q25.3-10q26.3<br>11p12-11q25<br>11p13-11p12<br>11p14.1-11p15.5<br>12p12.1-12p13.33<br>14q11.2-14q23.3<br>14q23.3-14q31.3<br>16p13.12-16q24.3<br>17p<br>17q<br>18q11.2-18q12.1<br>18q11.1-18q12.3<br>18q12.3<br>22q | 5q23.2<br>6p24.3<br>6p22.3<br>6p21.2-6p21.1<br>6p21.1<br>6p12.1-6p11.2<br>6q15<br>6q22.31<br>6q24.3-6q25.1<br>6q25.3<br>6q25.3<br>6q26<br>6q27<br>6q27<br>11p14.111p13<br>18q12.3<br>18q21.1 |
| PGBM21 | | 2q11.2-2q21.2<br>6p21.1-6q27<br>17q24.2-17q24.3<br>20q12-20q13.33 | 20p12.1-20p11.23<br>22q11.23<br>Xp22.33 | 1<br>2<br>3<br>4<br>5<br>8<br>9<br>10<br>11<br>16<br>17<br>18<br>19 | | | | 6p21.1-6p25.3<br>13q<br>14q<br>15q<br>20p13-20q12<br>21q<br>22q | Xp22.32 |

TABLE 9-continued

CNA regions identified in each tumour sample analyzed.

| Sample | GAINS | | | DELETIONS | | | LOH | |
|---|---|---|---|---|---|---|---|---|
| | Whole Chr | Broad | Focal | Whole Chr | Broad | Focal | Whole Chr | Broad | Focal |

| Sample | Whole Chr (Gains) | Broad (Gains) | Focal (Gains) | Whole Chr (Del) | Broad (Del) | Focal (Del) | Whole Chr (LOH) | Broad (LOH) | Focal (LOH) |
|---|---|---|---|---|---|---|---|---|---|
| PGBM23 | | | | | | | 3 | 13q | 11p14.3 |
| | | | | | | | 4 | 17p13.1-17p13.3 | |
| | | | | | | | | 19q | |
| PGBM24 | | 7q | 12p13.2-12p13.1 | | | 9p21.3 | 5 | 3q28-3q29 | 11p14.2-11p14.1 |
| | | 2p24.1-2p25.3 | | | | 15q14 | 6 | 9p | 11p11.2 |
| | | 2q24.1-2q33.2 | | | | | 8 | 9q34.13-9q34.3 | |
| | | 2q33.2-2q35 | | | | | 12 | 10p15.3-10q26.12 | |
| | | 4q26-4q31.22 | | | | | 17 | 11p15.2-11p15.5 | |
| | | 7p14.1-7p11.2 | | | | | 18 | 11p15.2-11p15.1 | |
| | | 7q11.23-7q36.3 | | | | | | 11p14.1-11p13 | |
| | | 10q26.12-10q26.3 | | | | | | 11p13-11p12 | |
| | | 13q21.31-13q34 | | | | | | 13q12.11-13q21.31 | |
| | | 15q23-15q26.3 | | | | | | 14q12-14q32.33 | |
| | | 16p13.3 | | | | | | 15q11.2-15q23 | |
| | | | | | | | | 16p11.2-16p13.3 | |
| | | | | | | | | 16q12.1-16q24.3 | |
| | | | | | | | | 19q13.2-19q13.43 | |
| | | | | | | | | 22q | |
| PGBM25 | | 4q26-4q28.1 | 2q33.2-2q33.3 | | 9p21.3-9p21.2 | 2q22.1-2q22.2 | 1 | 4q32.3-4q35.2 | 4p14-4p13 |
| | | 7p | 3q13.32 | | | 3q13.2 | 2 | 5q15-5q35.3 | 4q28.2 |
| | | 8p | 3q26.33-3q27.1 | | | 9p23 | 3 | 6p-6q13 | 17p13.3 |
| | | 8q24.13-8q24.22 | 4q12 | | | Xp21.2 | 9 | 6p12.1-6p11.2 | |
| | | 10q26.3 | 8q11.21-8q11.23 | | | | 10 | 6q13-6q25.3 | |
| | | 15q25.1 | 8q24.22 | | | | 11 | 6q25.3-6q27 | |
| | | | 9p24.3-9p24.2 | | | | 16 | 8q12.1-8q23.3 | |
| | | | 10q21.1 | | | | 17 | 8q24.22-8q24.3 | |
| | | | 10q25.1 | | | | 18 | 12q | |
| | | | 10q25.3 | | | | 19 | 13q | |
| | | | 10q26.2-10q26.3 | | | | 20 | 14q | |
| | | | | | | | | 15q14-15q26.3 | |
| | | | | | | | | 21q | |
| | | | | | | | | 22q | |
| PGBM26 | 16 | 9q33.3-9q34.3 | 5p13.2 | | 10p15.1-10p15.3 | | 2 | 1q42.13-1q44 | 19p13.2 |
| | 20 | 12q24.31-12p13.33 | 7q21.2 | | | | 3 | 13q | 19p13.2 |
| | | 14q | 10p12.2 | | | | 4 | 15q | 19p12-19p11 |
| | | 21q | 13q14.3 | | | | 5 | 19p13.3 | |
| | | | 13q21.1 | | | | 6 | 22q | |
| | | | 13q31.1 | | | | 8 | | |
| | | | 13q33.1 | | | | 10 | | |
| | | | 13q33.2 | | | | 17 | | |
| | | | 13q34 | | | | | | |
| | | | 19p13.12 | | | | | | |
| | | | 19p13.11-19p13.12 | | | | | | |
| PGBM27 | 2 | 5q12.1-5p15.33 | 2p25.1 | | | | 3 | 1q42.2-1q43 | 5q22.3 |
| | 7 | 9q31.3-9q21.33 | 2p24.3-2p24.2 | | | | 4 | 2p24.1-2p24.2 | 5q12.2-5q12.3 |
| | 16 | 9q21.33-9q21.13 | 2p24.1 | | | | 6 | 2p21-2p22.3 | 17q21.32 |
| | | 12p | 5q23.1 | | | | 8 | 5q | 18q23 |

TABLE 9-continued

CNA regions identified in each tumour sample analyzed.

| Sample | GAINS Whole Chr | GAINS Broad | GAINS Focal | DELETIONS Whole Chr | DELETIONS Broad | DELETIONS Focal | LOH Whole Chr | LOH Broad | LOH Focal |
|---|---|---|---|---|---|---|---|---|---|
| | | 21q | 5q22.2<br>7p11.2<br>7q21.13<br>7q21.2<br>7q33<br>7q33<br>10p15.1<br>11q12.1-11q11<br>15q26.3<br>19q13.43 | 11<br>17<br>18<br>19<br>X | 5q14.2-5q22.2<br>5p13.3-5p13.2<br>7q34-7q11.21<br>9q33.3-9q32<br>9q21.13-9p24.3<br>10q25.1-10q26.2<br>11q13.2-11q23.1<br>11p15.4-11p15.5<br>15q<br>22q | | | | 18q23 |
| PGBM31 | | 3q28-3q29<br>8q21.13-8q24.12<br>9p21.3-9p24.3<br>9p21.2-9p13.3<br>9q<br>20q13.2-20q13.33<br>22q11.23-22q11.21 | 5p15.33<br>9p13.3<br>9q21.33<br>18q22.2-18q22.3<br>19p13.3 | 17 | 3p24.3-3p26.3<br>3p14.2-3q26.31<br>8p | | | | |
| PGBM32 | | 1q<br>6p12.3-6p25.3 | 6q14.1<br>22q11.23-22q12.1 | | 9p21.3-9p21.1 | 6q12 | | | 6q12<br>6q13<br>6q13 |
| PGBM34 | 3<br>4<br>7 | 1q32.1-1q21.2<br>1p36.21-1p33<br>8q21.13-8q24.3<br>9q21.11-9q31.3<br>19p13.2-19p12<br>20p13-20q11.21<br>20q11.22-20q13.12<br>21q<br>22q13.2-22q13.31<br>Xp21.3-Xq27.3<br>Xp21.3-Xp22.33 | 1p36.22-1p36.21<br>1p32.2-1p32.1<br>1p31.1<br>1p13.3<br>19p13.3<br>22q11.21-22q11.22<br>22q11.21<br>22q11.21 | 10<br>11<br>12<br>17 | 1p<br>2q14.3-2p23.1<br>2q34-2q37.3<br>3p25.3-3p26.3<br>4q28.1-4q23.1<br>5q23.1-5q35.3<br>6p<br>6q<br>8p12-8p23.3<br>9p<br>13q<br>14q<br>15q11.2-15q22.2<br>15q22.2-15q26.3<br>19p12-19q12<br>20q13.12-20q13.2<br>22q | | | | 19p13.3<br>19p13.2 |
| PGBM35 | | 17q21.32-17q25.3 | 10q11.22 | 9<br>16<br>18 | Xq27.3-Xq28<br>22q | | | | |
| PGBM36 | | | 14q32.33<br>18q23 | | 22q | | | | |
| PGBM37 | | 1q | | | 2q14.1-2q31.3<br>6q12-6q27<br>8q24.22-8q24.3<br>9p21.1-9p24.3 | | | | 7p22.1<br>7q22.1<br>9q34.3<br>20p12.1 |

TABLE 9-continued

CNA regions identified in each tumour sample analyzed.

| Sample | GAINS Whole Chr | GAINS Broad | GAINS Focal | DELETIONS Whole Chr | DELETIONS Broad | DELETIONS Focal | LOH Whole Chr | LOH Broad | LOH Focal |
|---|---|---|---|---|---|---|---|---|---|
| PGBM39 | 3<br>7<br>19 | 21q | | 10<br>12<br>18 | 16q22.1-16q24.3<br>12p13.31-12p13.33<br>12p12.3-12p11.23 | 9p21.3<br>9p21.3<br>9p21.3 | | | 5p15.32-5p15.33<br>5p15.2<br>5p15.1<br>5p14.3<br>9p23<br>9p23<br>9p22.3<br>9p22.3-9p22.2<br>9p21.2<br>9p21.2-9p13.2<br>12p13.31<br>12p12.3 |
| PGBM40 | ZERO ALTERATIONS | | | | | | | | |
| PGBM41 | | | | | | | | | |
| PGBM42 | | | | | | | | | |
| PGBM43 | | 5p14.3-5p13.3<br>6q15-6p25.3<br>9p13.3-9q34.3<br>9p24.1-9p24.3<br>10p12.1-10p13 | 4q12<br>4q12<br>4q12<br>5p15.33<br>5p15.33-5p15.32<br>5p15.2<br>5p15.1<br>5p12<br>7q31.2-7q31.31<br>9p13.3<br>9p21.1<br>10q23.33-10q24.1<br>10p11.21-10p11.1<br>10p11.22<br>13q13.3<br>19p13.3 | 1<br>4<br>7<br>11<br>18 | 22q11.23-22q13.33 (CN)<br>2p<br>3q13.33-3q29<br>5q11.2-5q21.3<br>9p22.1-9p21.2<br>10q<br>12q21.2-12q23.1<br>13q<br>14q<br>15q<br>16q<br>17p<br>17q11.2-17q23.2<br>19q<br>20p<br>20q<br>22q<br>Xp | 4q34.3<br>7p14.1<br>11q22.3-11q23.1<br>20q13.31 | | | 8p11.22<br>4p12<br>5p15.32-5p15.31<br>5q31.3-5q32<br>6q24.3<br>9p23-9p22.3<br>10p11.23<br>12q24.31-12q24.32<br>16q23.2-16q23.3<br>19p13.3 |
| PGBM45 | | 1q | 2p24.3<br>2p25.1<br>2p25.1<br>2p25.3<br>7p11.2<br>9p24.3 | | Xq11.2-Xq21.31<br>1p32.2-1p34.1 | | | | 2p23.3-2p24.1<br>3p12.3-3p12.1<br>6p25.2-6p25.3<br>9p23<br>10p15.1-10p14<br>12q21.1-12q21.2 |

Example III

Tools for the Identification Histone Protein-Associated Mutations

Figure 11:
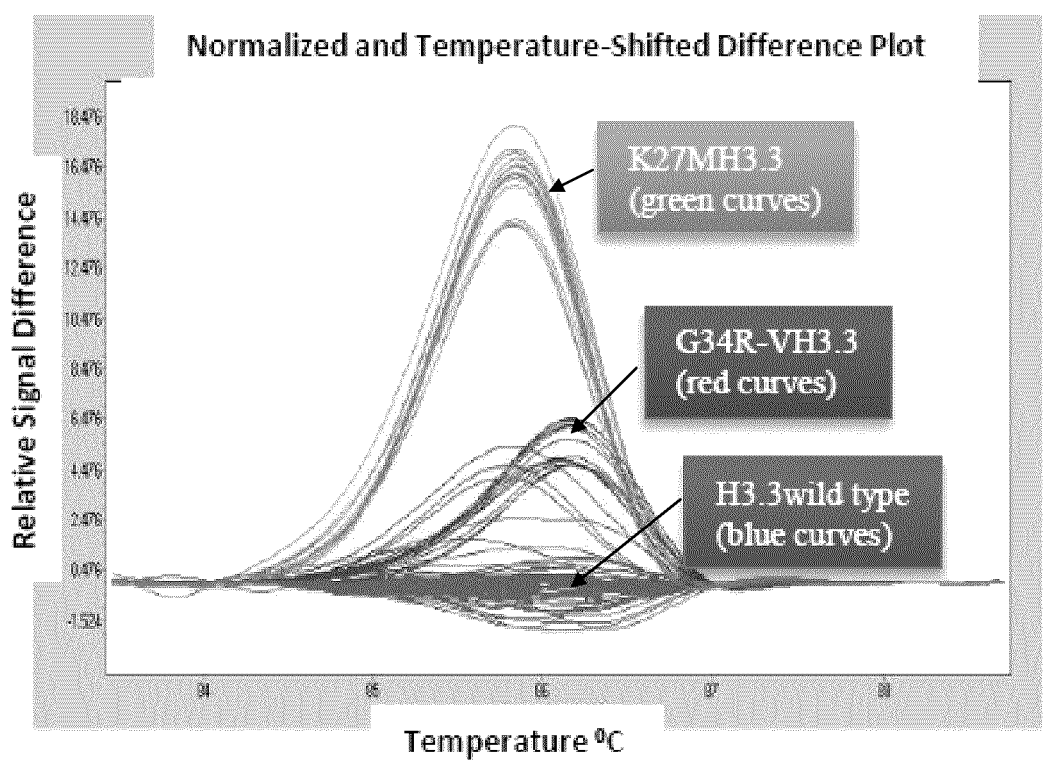
FIG. 11. Representative high-resolution melting curves for the identification of H3.3 mutants bearing a mutation at K27M or G34R. Results are shown as relative signal intensity in function of temperature.

We have developed several high resolution melting (HRM)-based and digital PCR protocols to analyse tumor and plasma DNA (and RNA). This technique allows detection of the variant nucleotide-based molecules (such as those derived from the H3.3 gene) with the resolution of 0.3%-0.001%, or with the sensitivity of up to 1 in 5 000 molecules (A. Narayan et al., Cancer Res 72, 3492 (Jul. 15, 2012)). Representative results from the HRM-based protocol is shown in FIG. 11. DNA was obtained from HGA tumour samples with a known H3.3 status (as assessed by whole exon sequencing or Sanger). A 100% correlation was obtained in 300 samples.

Figure 12:
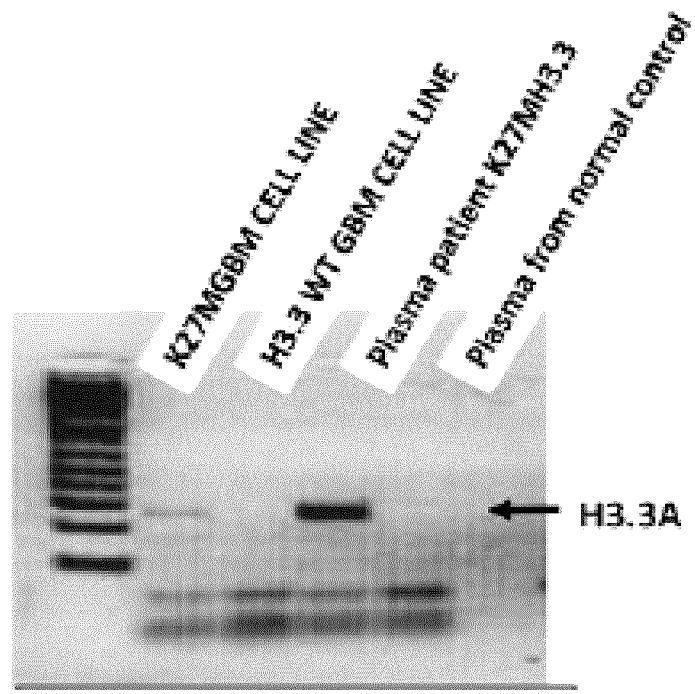
FIG. 12. Norton blot using a K27M H3.3 probe, of cell culture supernatant of cell lines (a mutated (K27MGBM cell line) or wild-type (H3.3 WT GBM cell line) and of plasma of patient (K27M plasma patient) or of a control individual (plasma from normal control).

We are able to detect circulating free DNA of the mutant forms of H3.3 in the plasma and in purified microvesicles from the plasma. H3.3 mRNA in conditioned media from a cell line (wild-type or bearing a mutation at H3.3. K27M) and from the plasma of a patient (bearing a mutation at H3.3 K27M) or a normal control (expressing wild-type H3.3) were extracted and probe for the presence of H3.3 mutant mRNA. As show on FIG. 12, mutant H3.3 mRNA was detected in the culture supernatant of cell lines bearing a K27M mutation and the plasma of the patient bearing the K27M mutation but not in the cell culture supernatant of the WT cell line or the control patient.

Figure 13:
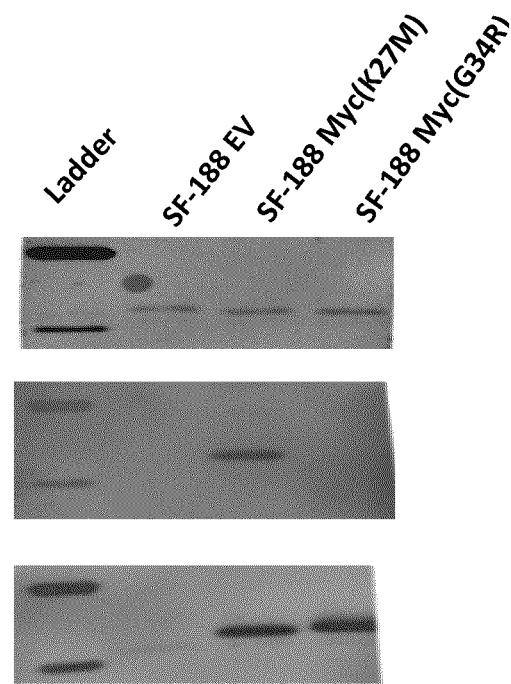
FIG. 13. Western blot of histone extracts of cells lines expressing wild type H3.3 (SF-188 EV), K27M H3.3 (SF-188 Myc(K27M)) or G34R H3.3 (SF-188 Myc(G34R)). Top panel shows results obtained with a monoclonal antibody recognizing the wild-type H3.3 polypeptide. Middle panel shows results obtained with a monoclonal antibody specific for the K27M H3.3 polypeptide. Lower panel shows results obtained with a monoclonal antibody specific for the Myc polypeptide.

We also were able to generate monoclonal antibodies derived in mouse hybridomas that recognize the mutant forms of H3.3. The mouse monoclonal antibodies were produced by Genescript usually the following peptides as antigens: KAARKSAPSTGGVKKC (SEQ ID NO: 10, wild-type H3.3 polypeptide), CATKAARMSAPST (SEQ ID NO: 11, K27M H3.3 polypeptide) or CSAPSTGRVKKPH (SEQ ID NO: 12, G24R H3.3 polypeptide). Histone extracts (1 μg/lane) obtained from cells expressing the wild-type H3.3 (SF-188 EV), the mutated K27M H3.3 (SF-188 Myc (K27M)) or the G34R H3.3 (SF-188 Myc(G34R)) were loaded on 12% PAGE-SDS gels. The gets were transferred, using TURBOBLOT™ transfer (Low MW program) on PVDF membranes. The membranes were incubated 1 h in a blocking solution (5% SM). The membranes were then washed 3 times for 5 min in a 0.1% TBST solution. The primary antibodies (a antiH3.3 wild type antibody, a rat anti-K27M H3.3 antibody or a rabbit anti-mouse Myc antibody) were added and the membranes were incubated overnight. The membranes were then washed 3 times for 5 min in a 0.1% TBST solution. The secondary antibodies were added and the membranes were incubated for 1 h. The membranes were then washed 3 times for 5 min in a 0.1% TBST solution. ECL as added and the membranes were incubates for 5 min before the STORM™ scanning. Results as shown on FIG. 13.

Figure 14:
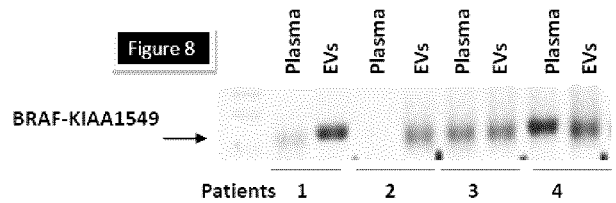
FIG. 14. Evidence that oncogenic transcripts can be extracted and enriched from minimal amounts of biological material containing tumour extravesicles (EVs/oncosomes). Detection of BRAF/KIAA in plasma of juvenile pilocytic astrocytoma patients by nested RT-PCR. The material was extracted from either unfractionated plasma or from the EV fraction of each sample. Starting material was 250 µL for all lanes.

Concentration of tumor-derived molecular cargo in EVs (oncosomes) offers a unique opportunity to increase the robustness of plasma-based DNA and mRNA testing. Such EVs may also contain oncogenic mRNA (and microRNA) species, and proteins, including H3.3. We have validated RT-PCR approaches and protein extraction protocols to detect oncogenic transcripts/protein in the cargo of oncosomes released from HGA. We show we can detect in oncosomes mutant transcripts/proteins for EGFRvIII. We also detect oncogenic transcripts (H3.3K27M) in the plasma containing oncosomes released from HGA in as little as 250 uL of plasma derived EVs. While in some instances it is possible to directly extract mRNA from plasma aliquots, the prior purification of the EV/exosome fraction affords greater reproducibility, several fold enrichment potential and combinatorial read out (mutant RNA and its transcriptional targets from the same cellular source). FIG. 14 illustrates the enrichment of signal in purified oncosomes versus plasma for the mutant KIAA1549-BRAF transcript in low grade gliomas.

Example IV

Additional Clinical Validation

Figure 15A:
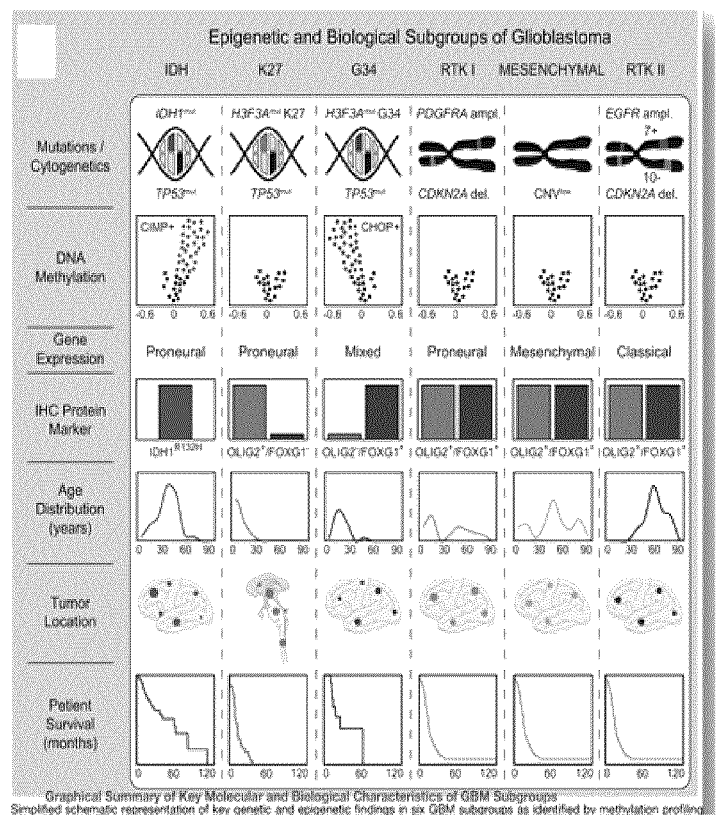
FIGS. 15A, 15B and 15C. (A) Graphical representation of Epigenetic and Biological Subgroups of glioblastoma reviewing, per mutated gene, the DNA methylation pattern, the gene expression, the IHC protein marker, the age distribution, the tumor location as well as the patient survival (in months). (B) Neuroatonomical and age specificity of IDH, H3.3-K27M and G34R in the brain GBM. K27M occurs mainly in the brainstem and the thalamus (70%-80% of all GBM in these locations). It is inconsistently associated with ATRX mutations. G34V-R occurs mainly in the cerebral hemispheres similar to IDH mutations that have a predilection for the frontal cortex. Both are strongly and significantly associated with ATRX mutations. SETD2 mutations are in the brain hemispheres and partly overlap with IDH mutations in a sample. The size of the shape illustrating each mutation is proportional to the % identified in our studies. (C) Cumulative survival (%) in function of overall survival (years) for patients expressing wilt-type H3.3 or K27M H3.3 polypeptide (p=0.027). Thalamic and pontine high grade gliomas carrying K27MH3.3 mutations have universal rapid poor outcome.
Figure 15B:
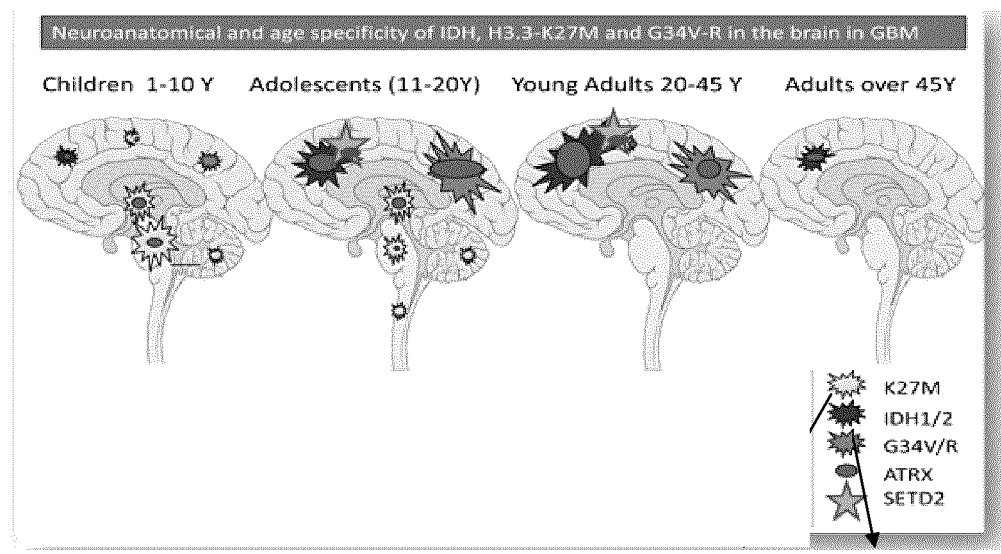
Figure 15C:
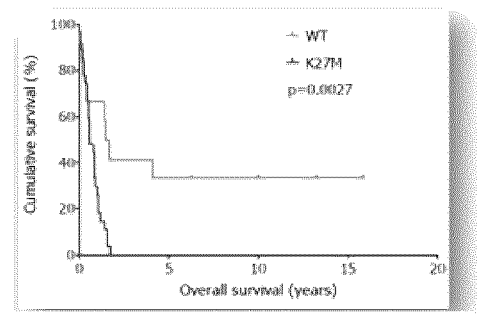

Using an independent cohort of ~790 gliomas across age, group and grade, we further showed H3.3 mutations to be specific to high-grade tumors, to be prevalent in children (incidence <3.4% in adult HGA), and to have neuroanatomical and age specificities (FIG. 15). Indeed, our findings indicate potentially a developmental origin of pediatric HGA. K27M mutations occur in younger children and target the brainstem and the thalamus (70-80% of all HGA cases in these regions, tumors of the midline). They overlap with TP53 mutations in 80% of cases and with ATRX mutations in only 50% of cases, mainly in older children. G34V-R mutations are mainly found in HGA within the cerebral hemispheres, occur in older children and young adults and almost always overlap with mutant TP53/ATRX. Also, important to this study, our results indicate universally worse prognosis and rapid death (within 18 months) for K27M tumors, which behave like DIPG whatever their localization within the brain (FIG. 15). We also showed that ATRX mutations characterize adult IDH-mutant gliomas of the astrocytic lineage arguing for the importance of an ATRX & IDH1/2 & TP53 mutant phenotype in their early development and progression. Collectively, these findings indicate that defects in chromatin remodeling are central and that age and brain-location specific defects in chromatin structure underlie the genesis of pediatric and young adult HGA.

We also investigated a subset of childhood HGAs (n=59) and a cohort of young adult cases (n=77) using the Illumina 450k INFINIUM™ Methylation Array. Adult samples were enriched for tumors carrying IDH1 or H3.3 mutations. Results are shown in FIG. 16. We also screened all samples with available DNA for mutations in H3F3A, IDH1 and TP53. Notably, 88% of IDH1-mutated tumors (23/26) were found in the cluster 1 extending the results previously described to a pediatric setting. Most strikingly, however, H3F3A K27 and G34 mutations were exclusively distributed to cluster 2 (18/18) and cluster 3 (18/18), respectively (FIG. 16). This data was obtained at low resolution (Illumina 450K assay measuring ~1% of CpG sites in the genome). We also compared low coverage (2-7× per strand) methylC-seq to Illumina 450K to interrogate inter-individual CpG-methylation variation and Its correlation to other functional genomic data (RNA-seq). Overall, more than 100 times greater inter-individual methylation variation was revealed by methylC-seq even at the lowest sequencing depth, while agreement between the two methods remained high (FIG. 17). Unbiased methylation seq observed substantially higher genome methylation as compared to estimates based on targeted 450K analyses. Furthermore, expression phenotypes correlate substantially better with methylC-seq than with Illumina 450K.

In a mouse model, the tumorigenicity potential of non-conservative H3.3 variants has been investigated. As show on FIG. 18, within 3 weeks pups injected with K27M-H3.3 (3/10) or G34R-H3.3 (2/7) alone generate tumors. We generated transgenic mice expressing H3.3 mutants under the control of an astrocytic lineage promoter (GFAP, mature astrocytes and nestin, neural stem cells).

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. An antibody specific for an isolated polypeptide consisting of the amino acid sequence of SEQ ID NO:6, SEQ ID NO:7, or SEQ ID NO:8.

2. The antibody of claim 1 being a polyclonal antibody.

3. The antibody of claim 1, wherein the isolated polypeptide consists of the amino acid sequence of SEQ ID NO:1, SEQ ID NO: 2, SEQ ID NO:3, or SEQ ID NO:4.

4. An antibody specific for an isolated polypeptide consisting of the amino acid sequence of SEQ ID NO: 11 or 12.

5. The antibody of claim 4 being monoclonal.

* * * * *

SEQUENCE LISTING

```
<160> NUMBER OF SEQ ID NOS: 17

<210> SEQ ID NO 1
<211> LENGTH: 135
<212> TYPE: PRT
<213> ORGANISM: Homo sapiens

<400> SEQUENCE: 1

Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Met Ser Ala Pro Ser Thr
            20                  25                  30

Gly Gly Val Lys Lys Pro His Arg Tyr Arg Pro Gly Thr Val Ala Leu
        35                  40                  45

Arg Glu Ile Arg Arg Tyr Gln Lys Ser Thr Glu Leu Leu Ile Arg Lys
    50                  55                  60

Leu Pro Phe Gln Arg Leu Val Arg Glu Ile Ala Gln Asp Phe Lys Thr
65                  70                  75                  80

Asp Leu Arg Phe Gln Ser Ala Ala Ile Gly Ala Leu Gln Glu Ala Ser
                85                  90                  95

Glu Ala Tyr Leu Val Gly Leu Phe Glu Asp Thr Asn Leu Cys Ala Ile
            100                 105                 110

His Ala Lys Arg Val Thr Ile Met Pro Lys Asp Ile Gln Leu Ala Arg
        115                 120                 125

Arg Ile Arg Gly Glu Arg Ala
    130                 135

<210> SEQ ID NO 2
<211> LENGTH: 135
<212> TYPE: PRT
<213> ORGANISM: Homo sapiens

<400> SEQUENCE: 2

Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Lys Ser Ala Pro Ser Thr
            20                  25                  30

Gly Arg Val Lys Lys Pro His Arg Tyr Arg Pro Gly Thr Val Ala Leu
        35                  40                  45

Arg Glu Ile Arg Arg Tyr Gln Lys Ser Thr Glu Leu Leu Ile Arg Lys
    50                  55                  60

Leu Pro Phe Gln Arg Leu Val Arg Glu Ile Ala Gln Asp Phe Lys Thr
65                  70                  75                  80

Asp Leu Arg Phe Gln Ser Ala Ala Ile Gly Ala Leu Gln Glu Ala Ser
                85                  90                  95

Glu Ala Tyr Leu Val Gly Leu Phe Glu Asp Thr Asn Leu Cys Ala Ile
            100                 105                 110

His Ala Lys Arg Val Thr Ile Met Pro Lys Asp Ile Gln Leu Ala Arg
        115                 120                 125

Arg Ile Arg Gly Glu Arg Ala
```

```
            130                 135

<210> SEQ ID NO 3
<211> LENGTH: 135
<212> TYPE: PRT
<213> ORGANISM: Homo sapiens

<400> SEQUENCE: 3

Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Lys Ser Ala Pro Ser Thr
            20                  25                  30

Gly Val Val Lys Lys Pro His Arg Tyr Arg Pro Gly Thr Val Ala Leu
        35                  40                  45

Arg Glu Ile Arg Arg Tyr Gln Lys Ser Thr Glu Leu Leu Ile Arg Lys
50                  55                  60

Leu Pro Phe Gln Arg Leu Val Arg Glu Ile Ala Gln Asp Phe Lys Thr
65                  70                  75                  80

Asp Leu Arg Phe Gln Ser Ala Ala Ile Gly Ala Leu Gln Glu Ala Ser
                85                  90                  95

Glu Ala Tyr Leu Val Gly Leu Phe Glu Asp Thr Asn Leu Cys Ala Ile
            100                 105                 110

His Ala Lys Arg Val Thr Ile Met Pro Lys Asp Ile Gln Leu Ala Arg
        115                 120                 125

Arg Ile Arg Gly Glu Arg Ala
    130                 135

<210> SEQ ID NO 4
<211> LENGTH: 135
<212> TYPE: PRT
<213> ORGANISM: Homo sapiens
<220> FEATURE:
<221> NAME/KEY: VARIANT
<222> LOCATION: (34)..(34)
<223> OTHER INFORMATION: /replace = Val

<400> SEQUENCE: 4

Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Met Ser Ala Pro Ser Thr
            20                  25                  30

Gly Arg Val Lys Lys Pro His Arg Tyr Arg Pro Gly Thr Val Ala Leu
        35                  40                  45

Arg Glu Ile Arg Arg Tyr Gln Lys Ser Thr Glu Leu Leu Ile Arg Lys
50                  55                  60

Leu Pro Phe Gln Arg Leu Val Arg Glu Ile Ala Gln Asp Phe Lys Thr
65                  70                  75                  80

Asp Leu Arg Phe Gln Ser Ala Ala Ile Gly Ala Leu Gln Glu Ala Ser
                85                  90                  95

Glu Ala Tyr Leu Val Gly Leu Phe Glu Asp Thr Asn Leu Cys Ala Ile
            100                 105                 110

His Ala Lys Arg Val Thr Ile Met Pro Lys Asp Ile Gln Leu Ala Arg
        115                 120                 125

Arg Ile Arg Gly Glu Arg Ala
    130                 135

<210> SEQ ID NO 5
<211> LENGTH: 135
```

```
<212> TYPE: PRT
<213> ORGANISM: Homo sapiens

<400> SEQUENCE: 5

Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Lys Ser Ala Pro Ser Thr
            20                  25                  30

Gly Gly Val Lys Lys Pro His Arg Tyr Arg Pro Gly Thr Val Ala Leu
        35                  40                  45

Arg Glu Ile Arg Arg Tyr Gln Lys Ser Thr Glu Leu Leu Ile Arg Lys
50                  55                  60

Leu Pro Phe Gln Arg Leu Val Arg Glu Ile Ala Gln Asp Phe Lys Thr
65                  70                  75                  80

Asp Leu Arg Phe Gln Ser Ala Ala Ile Gly Ala Leu Gln Glu Ala Ser
                85                  90                  95

Glu Ala Tyr Leu Val Gly Leu Phe Glu Asp Thr Asn Leu Cys Ala Ile
            100                 105                 110

His Ala Lys Arg Val Thr Ile Met Pro Lys Asp Ile Gln Leu Ala Arg
        115                 120                 125

Arg Ile Arg Gly Glu Arg Ala
    130                 135

<210> SEQ ID NO 6
<211> LENGTH: 135
<212> TYPE: PRT
<213> ORGANISM: Homo sapiens
<220> FEATURE:
<221> NAME/KEY: VARIANT
<222> LOCATION: (27)..(27)
<223> OTHER INFORMATION: Xaa is any naturally occuring amino acid except
      Lys

<400> SEQUENCE: 6

Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Xaa Ser Ala Pro Ser Thr
            20                  25                  30

Gly Gly Val Lys Lys Pro His Arg Tyr Arg Pro Gly Thr Val Ala Leu
        35                  40                  45

Arg Glu Ile Arg Arg Tyr Gln Lys Ser Thr Glu Leu Leu Ile Arg Lys
50                  55                  60

Leu Pro Phe Gln Arg Leu Val Arg Glu Ile Ala Gln Asp Phe Lys Thr
65                  70                  75                  80

Asp Leu Arg Phe Gln Ser Ala Ala Ile Gly Ala Leu Gln Glu Ala Ser
                85                  90                  95

Glu Ala Tyr Leu Val Gly Leu Phe Glu Asp Thr Asn Leu Cys Ala Ile
            100                 105                 110

His Ala Lys Arg Val Thr Ile Met Pro Lys Asp Ile Gln Leu Ala Arg
        115                 120                 125

Arg Ile Arg Gly Glu Arg Ala
    130                 135

<210> SEQ ID NO 7
<211> LENGTH: 135
<212> TYPE: PRT
<213> ORGANISM: Homo sapiens
<220> FEATURE:
<221> NAME/KEY: VARIANT
```

```
<222> LOCATION: (34)..(34)
<223> OTHER INFORMATION: Xaa is any naturally occuring amino acid except
      Gly

<400> SEQUENCE: 7

Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Leu Ser Ala Pro Ser Thr
            20                  25                  30

Gly Xaa Val Lys Lys Pro His Arg Tyr Arg Pro Gly Thr Val Ala Leu
        35                  40                  45

Arg Glu Ile Arg Arg Tyr Gln Lys Ser Thr Glu Leu Leu Ile Arg Lys
50                  55                  60

Leu Pro Phe Gln Arg Leu Val Arg Glu Ile Ala Gln Asp Phe Lys Thr
65                  70                  75                  80

Asp Leu Arg Phe Gln Ser Ala Ala Ile Gly Ala Leu Gln Glu Ala Ser
                85                  90                  95

Glu Ala Tyr Leu Val Gly Leu Phe Glu Asp Thr Asn Leu Cys Ala Ile
            100                 105                 110

His Ala Lys Arg Val Thr Ile Met Pro Lys Asp Ile Gln Leu Ala Arg
        115                 120                 125

Arg Ile Arg Gly Glu Arg Ala
    130                 135

<210> SEQ ID NO 8
<211> LENGTH: 135
<212> TYPE: PRT
<213> ORGANISM: Homo sapiens
<220> FEATURE:
<221> NAME/KEY: VARIANT
<222> LOCATION: (27)..(27)
<223> OTHER INFORMATION: Xaa is any naturally occuring amino acid except
      Lys
<220> FEATURE:
<221> NAME/KEY: VARIANT
<222> LOCATION: (34)..(34)
<223> OTHER INFORMATION: Xaa is any naturally occuring amino acid except
      Gly

<400> SEQUENCE: 8

Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Xaa Ser Ala Pro Ser Thr
            20                  25                  30

Gly Xaa Val Lys Lys Pro His Arg Tyr Arg Pro Gly Thr Val Ala Leu
        35                  40                  45

Arg Glu Ile Arg Arg Tyr Gln Lys Ser Thr Glu Leu Leu Ile Arg Lys
50                  55                  60

Leu Pro Phe Gln Arg Leu Val Arg Glu Ile Ala Gln Asp Phe Lys Thr
65                  70                  75                  80

Asp Leu Arg Phe Gln Ser Ala Ala Ile Gly Ala Leu Gln Glu Ala Ser
                85                  90                  95

Glu Ala Tyr Leu Val Gly Leu Phe Glu Asp Thr Asn Leu Cys Ala Ile
            100                 105                 110

His Ala Lys Arg Val Thr Ile Met Pro Lys Asp Ile Gln Leu Ala Arg
        115                 120                 125

Arg Ile Arg Gly Glu Arg Ala
    130                 135
```

```
<210> SEQ ID NO 9
<211> LENGTH: 21
<212> TYPE: DNA
<213> ORGANISM: Homo sapiens

<400> SEQUENCE: 9
gcccccacca tgagcgctgc t                                              21

<210> SEQ ID NO 10
<211> LENGTH: 16
<212> TYPE: PRT
<213> ORGANISM: Homo sapiens

<400> SEQUENCE: 10

Lys Ala Ala Arg Lys Ser Ala Pro Ser Thr Gly Gly Val Lys Lys Cys
1               5                   10                  15

<210> SEQ ID NO 11
<211> LENGTH: 13
<212> TYPE: PRT
<213> ORGANISM: Homo sapiens

<400> SEQUENCE: 11

Cys Ala Thr Lys Ala Ala Arg Met Ser Ala Pro Ser Thr
1               5                   10

<210> SEQ ID NO 12
<211> LENGTH: 13
<212> TYPE: PRT
<213> ORGANISM: Homo sapiens

<400> SEQUENCE: 12

Cys Ser Ala Pro Ser Thr Gly Arg Val Lys Lys Pro His
1               5                   10

<210> SEQ ID NO 13
<211> LENGTH: 18
<212> TYPE: DNA
<213> ORGANISM: Artificial Sequence
<220> FEATURE:
<223> OTHER INFORMATION: Telomere probe

<400> SEQUENCE: 13
ttagggttag ggttaggg                                                  18

<210> SEQ ID NO 14
<211> LENGTH: 50
<212> TYPE: PRT
<213> ORGANISM: Artificial Sequence
<220> FEATURE:
<223> OTHER INFORMATION: Fragment of H3.3 generic to H. sapiens, M.
      musculus and D. melanogaster

<400> SEQUENCE: 14

Ser Thr Gly Gly Lys Ala Pro Arg Lys Gln Leu Ala Thr Lys Ala Ala
1               5                   10                  15

Arg Lys Ser Ala Pro Ser Thr Gly Gly Val Lys Lys Pro His Arg Tyr
                20                  25                  30

Arg Pro Gly Thr Val Ala Leu Arg Glu Ile Arg Arg Tyr Gln Lys Ser
            35                  40                  45

Thr Glu
    50

<210> SEQ ID NO 15
```

```
<211> LENGTH: 50
<212> TYPE: PRT
<213> ORGANISM: Homo sapiens

<400> SEQUENCE: 15

Ser Thr Gly Gly Lys Ala Pro Arg Lys Gln Leu Ala Thr Lys Ala Ala
1               5                   10                  15

Arg Lys Ser Ala Pro Ala Thr Gly Gly Val Lys Lys Pro His Arg Tyr
            20                  25                  30

Arg Pro Gly Thr Val Ala Leu Arg Glu Ile Arg Arg Tyr Gln Lys Ser
        35                  40                  45

Thr Glu
    50

<210> SEQ ID NO 16
<211> LENGTH: 50
<212> TYPE: PRT
<213> ORGANISM: Schizosaccharomyces pombe

<400> SEQUENCE: 16

Ser Thr Gly Gly Lys Ala Pro Arg Lys Gln Leu Ala Ser Lys Ala Ala
1               5                   10                  15

Arg Lys Ala Ala Pro Ser Thr Gly Gly Val Lys Lys Pro His Arg Tyr
            20                  25                  30

Arg Pro Gly Thr Val Ala Leu Arg Glu Ile Arg Arg Tyr Gln Lys Ser
        35                  40                  45

Thr Glu
    50

<210> SEQ ID NO 17
<211> LENGTH: 50
<212> TYPE: PRT
<213> ORGANISM: Arabidopsis thaliana

<400> SEQUENCE: 17

Ser His Gly Gly Lys Ala Pro Thr Lys Gln Leu Ala Thr Lys Ala Ala
1               5                   10                  15

Arg Lys Ser Ala Pro Thr Thr Gly Gly Val Lys Lys Pro His Arg Phe
            20                  25                  30

Arg Pro Gly Thr Val Ala Leu Arg Glu Ile Arg Arg Tyr Gln Lys Ser
        35                  40                  45

Thr Glu
    50
```